(12) United States Patent
Ishii et al.

(10) Patent No.: US 10,177,530 B2
(45) Date of Patent: Jan. 8, 2019

(54) OPTICAL SENSOR, OPTICAL EXAMINATION DEVICE, AND OPTICAL PROPERTY DETECTION METHOD

(71) Applicants: Toshihiro Ishii, Miyagi (JP); Yoichiro Takahashi, Miyagi (JP); Sunao Chubachi, Miyagi (JP); Masayuki Fujiwara, Miyagi (JP); Toshihide Sasaki, Kanagawa (JP); Kazuhiko Adachi, Miyagi (JP)

(72) Inventors: Toshihiro Ishii, Miyagi (JP); Yoichiro Takahashi, Miyagi (JP); Sunao Chubachi, Miyagi (JP); Masayuki Fujiwara, Miyagi (JP); Toshihide Sasaki, Kanagawa (JP); Kazuhiko Adachi, Miyagi (JP)

(73) Assignee: RICOH COMPANY, LTD., Tokyo (JP)

( * ) Notice: Subject to any disclaimer, the term of this patent is extended or adjusted under 35 U.S.C. 154(b) by 0 days.

(21) Appl. No.: 15/379,856

(22) Filed: Dec. 15, 2016

(65) Prior Publication Data
US 2017/0179682 A1    Jun. 22, 2017

(30) Foreign Application Priority Data

Dec. 22, 2015    (JP) .................................. 2015-250241

(51) Int. Cl.
*H01S 5/026* (2006.01)
*A61B 5/00* (2006.01)
(Continued)

(52) U.S. Cl.
CPC .......... *H01S 5/0262* (2013.01); *A61B 5/0042* (2013.01); *A61B 5/0073* (2013.01);
(Continued)

(58) Field of Classification Search
CPC . A61B 2505/09; A61B 5/0042; A61B 5/0073; A61B 5/165; A61B 2562/0233;
(Continued)

(56) References Cited

U.S. PATENT DOCUMENTS

| 4,888,625 A | 12/1989 | Mueller |
| 6,488,704 B1 | 12/2002 | Connelly et al. |

(Continued)

FOREIGN PATENT DOCUMENTS

| JP | 2004-229920 | 8/2004 |
| JP | 2012-187376 | 10/2012 |

(Continued)

OTHER PUBLICATIONS

European search report dated May 19, 2017 in connection with corresponding European patent application No. 16203002.7.

*Primary Examiner* — Tri T Ton
(74) *Attorney, Agent, or Firm* — Cooper & Dunham LLP

(57) ABSTRACT

An optical sensor, an optical examination device, and a method of detecting optical properties. The optical sensor includes an irradiation system including light irradiator to irradiate a test object with light, and a detection system to detect the light that is emitted from the irradiation system to the test object and has propagated through the test object. The light irradiator includes a multilayered structure having an active layer, and the multilayered structure includes a surface-emitting laser element and a photo-sensing element optically connected to the surface-emitting laser element. The optical examination device includes the optical sensor, and a controller to calculate optical properties of the test object based on a detection result of the optical sensor. The method includes performing optical simulation to obtain a detection light quantity distribution for an optical model and performing inverse problem estimation.

15 Claims, 50 Drawing Sheets

(51) Int. Cl.
    A61B 5/16      (2006.01)
    G01J 1/02      (2006.01)
    G01N 21/47     (2006.01)
    H01L 31/0224   (2006.01)
    H01L 31/0232   (2014.01)
    H01L 31/103    (2006.01)
    H01L 31/167    (2006.01)
    H01S 5/183     (2006.01)
    A61B 5/026     (2006.01)
    A61B 5/055     (2006.01)
    A61B 5/1455    (2006.01)
    G01J 1/04      (2006.01)
    G01N 21/359    (2014.01)
    G01N 21/49     (2006.01)
    H01S 5/42      (2006.01)
    H01S 5/022     (2006.01)

(52) U.S. Cl.
    CPC ............ *A61B 5/0261* (2013.01); *A61B 5/055* (2013.01); *A61B 5/1455* (2013.01); *A61B 5/165* (2013.01); *A61B 5/4887* (2013.01); *G01J 1/0209* (2013.01); *G01J 1/0411* (2013.01); *G01N 21/359* (2013.01); *G01N 21/4785* (2013.01); *G01N 21/4795* (2013.01); *G01N 21/49* (2013.01); *H01L 31/02327* (2013.01); *H01L 31/022408* (2013.01); *H01L 31/103* (2013.01); *H01L 31/167* (2013.01); *H01S 5/0264* (2013.01); *H01S 5/02288* (2013.01); *H01S 5/18347* (2013.01); *H01S 5/18358* (2013.01); *A61B 2505/09* (2013.01); *A61B 2562/0233* (2013.01); *A61B 2562/146* (2013.01); *A61B 2562/16* (2013.01); *G01N 2201/0612* (2013.01); *H01S 5/02208* (2013.01); *H01S 5/423* (2013.01)

(58) Field of Classification Search
    CPC .......... A61B 2562/146; A61B 2562/16; A61B 5/0261; A61B 5/055; A61B 5/1455; G01J 1/0209; G01J 1/0411; G01N 21/4785; G01N 21/4795
    USPC .................................. 356/432–448, 213–236
    See application file for complete search history.

(56) References Cited

U.S. PATENT DOCUMENTS

| | | | |
|---|---|---|---|
| 2006/0050755 A1* | 3/2006 | Suzuki | H01S 5/423 372/50.121 |
| 2010/0016732 A1* | 1/2010 | Wells | A61B 5/0059 600/476 |
| 2010/0069727 A1 | 3/2010 | Kawano et al. | |
| 2013/0109975 A1 | 5/2013 | Giardini et al. | |
| 2016/0242647 A1 | 8/2016 | Ishii et al. | |

FOREIGN PATENT DOCUMENTS

| | | |
|---|---|---|
| JP | 2014-083069 | 5/2014 |
| JP | 2015-092151 | 5/2015 |
| WO | 2015/046624 A1 | 4/2015 |

* cited by examiner

| DEPTH (mm) | CONTROL SAMPLE | SECOND EXAMPLE |
|---|---|---|
| 2 | × | ○ |
| 4 | × | ○ |
| 6 | × | ○ |
| 8 | × | ○ |
| 10 | × | ○ |
| 12 | × | ○ |
| 14 | × | ○ |
| 16 | × | ○ |
| 17 | × | × |

OPTICAL SENSOR, OPTICAL EXAMINATION DEVICE, AND OPTICAL PROPERTY DETECTION METHOD

CROSS-REFERENCE TO RELATED APPLICATION

This patent application is based on and claims priority pursuant to 35 U.S.C. § 119(a) to Japanese Patent Application No. 2015-250241, filed on Dec. 22, 2015, in the Japan Patent Office, the entire disclosure of which is hereby incorporated by reference herein.

BACKGROUND

Technical Field

Embodiments of the present invention relate to an optical sensor, an optical examination device incorporating the optical sensor, and an optical property detection method using the optical sensor.

Background Art

Conventionally, an optical live subject measuring device that irradiates a test object (for example, a live subject) with light to detect the light that has propagated inside the test object, for measuring and obtaining the internal information of the test object, is known.

However, the optical live subject measuring device has room for improvement in the measurement accuracy of the internal information of the test object.

SUMMARY

Embodiments of the present invention described herein provide an optical sensor, an optical examination device, and a method of detecting optical properties. The optical sensor includes an irradiation system including at least one light irradiator to irradiate a test object with light, and a detection system to detect the light that is emitted from the irradiation system to the test object and has propagated through the test object. The light irradiator includes a multilayered structure having an active layer, and the multilayered structure includes at least one surface-emitting laser element and a photo-sensing element optically connected to the at least one surface-emitting laser element. The optical examination device includes the optical sensor, and a controller to calculate optical properties of the test object based on a detection result of the optical sensor. The method of detecting optical properties includes performing optical simulation to obtain a detection light quantity distribution for an optical model that simulates a test object and performing inverse problem estimation using a result of the optical simulation.

BRIEF DESCRIPTION OF THE DRAWINGS

A more complete appreciation of exemplary embodiments and the many attendant advantages thereof will be readily obtained as the same becomes better understood by reference to the following detailed description when considered in connection with the accompanying drawings.

Figure 1:
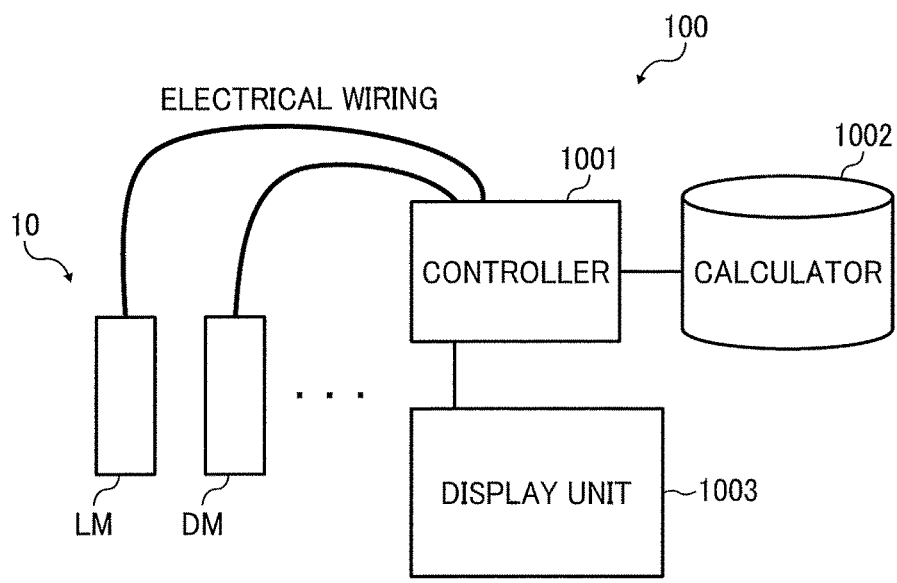
FIG. 1 is a diagram illustrating a general configuration of an optical examination device according to a first embodiment of the present invention.

The accompanying drawings are intended to depict exemplary embodiments of the present disclosure and should not be interpreted to limit the scope thereof. The accompanying drawings are not to be considered as drawn to scale unless explicitly noted.

DETAILED DESCRIPTION

The terminology used herein is for the purpose of describing particular embodiments only and is not intended to be limiting of the present invention. As used herein, the singular forms "a", "an" and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing example embodiments shown in the drawings, specific terminology is employed for the sake of clarity. However, the present disclosure is not intended to be limited to the specific terminology so selected and it is to be understood that each specific element includes all technical equivalents that have the same structure, operate in a similar manner, and achieve a similar result.

[First Embodiment]

In the following description, a first embodiment of the present invention is described with reference to FIG. 1 to FIG. 36.

FIG. 1 illustrates a general configuration of an optical examination device 100 according to the first embodiment of the present invention.

For example, the optical examination device 100 is used for diffuse optical tomography (DOT), a technique in which a test object (scatterer) such as a live subject is irradiated with light and the light that has propagated inside the test object is detected to gauge the internal optical properties of the test object. In particular, applications to aids for differential diagnosis of depression, and application to ancillary equipment of rehabilitation, by detecting the bloodstream inside a brain, are expected. In DOT, an improvement in resolution leads to a better understanding of the functions of the brain. For this reason, active studies are set out in many research institutions to improve the resolution.

As illustrated in FIG. 1, the optical examination device 100 includes, for example, a controller 1001, a calculator 1002, a display unit 1003, and an optical sensor 10 incorporating a detection module DM and a light source module LM including a plurality of light-emitting units.

Figure 42:
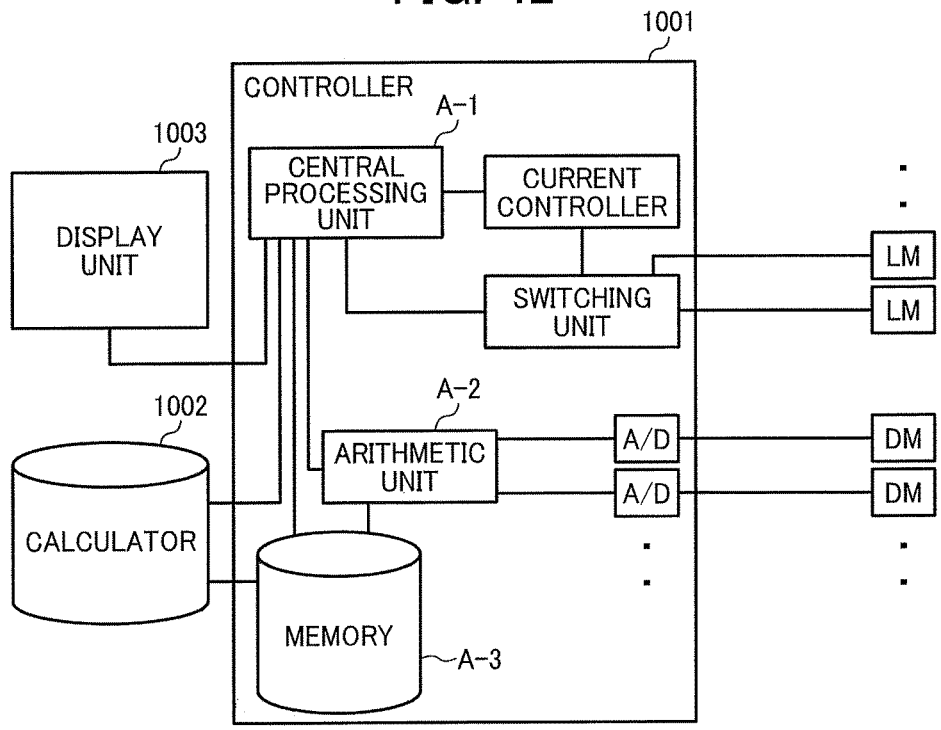
FIG. 42 is a block diagram illustrating a configuration of a controller according to an embodiment of the present invention.

FIG. 42 is a block diagram illustrating a configuration of a controller 1001 according to an embodiment of the present invention.

The controller 1001 is configured as illustrated in the block diagram of FIG. 42. In the following description, the light source module LM and the detection module DM may be referred to simply as "LM" and "DM", respectively.

Each of the light source modules LM is connected to the controller 1001 through two wires. One wire connects the light source module LM to a central processing unit A-1, and the other wire connects the light source module LM to a switching unit. Each of the light source modules LM sends a digital signal indicating a value of light quantity measured by a light-emitting unit to the central processing unit A-1. The central processing unit A-1 monitors the digital signal (measured value) sent from the light source modules LM, and calculates a desired current value. Then, the central processing unit A-1 sends the calculated current value to a current controller. Moreover, the central processing unit A-1 controls the switching unit to select the light source modules LM that are to emit light. In so doing, the current that is supplied to the light source module LM through the switching unit is controlled by the current controller to have a desired value. Note that the monitoring of the light quantity at a light-emitting unit will be described later in detail.

The detection result (data) of the detection module DM is analog-to-digital (A/D) converted, and operation such as averaging is performed at an arithmetic unit A-2. The results of the operation performed at the arithmetic unit A-2 are sequentially stored in a memory A-3.

In the following description, the light source module LM and the detection module DM may be referred to as a probe when it is not necessary to distinguish between these two elements. In the following description, terms such as a pseudo live subject, a live subject, and a test object are used where appropriate. It is to be noted that a pseudo live subject and a live subject are examples of the test object.

The optical sensor 10 can generally be used as a sensor that detects a light absorber in the test object, but the test object with the highest utility value is a live subject. However, as known in the art, it is not always easy to detect the position of the bloodstream (light absorber) of a live subject by using an optical sensor. In other words, it is difficult to check the effectiveness (accuracy of detection) of the optical sensor 10 when the test object is a live subject.

In order to handle such a situation and achieve versatility, in the present embodiment, a pseudo live subject, i.e., whitish liquid in a watertank, is adopted as a test object in which the accuracy of detection can easily be checked. In the following description, such a pseudo live subject may be referred to as a phantom.

Next, a first variation of the present embodiment is described below.

[First Variation]

In the first variation, the light beams emitted from a plurality of light-emitting units are deflected by a prism to vary the incident angle to the test object for each of the light beams.

Figure 2:
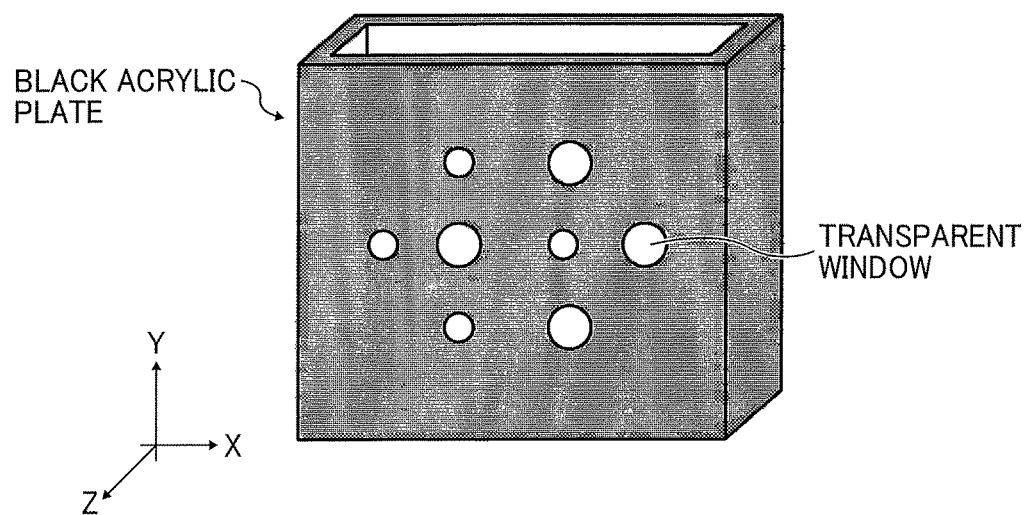
FIG. 2 is a diagram illustrating a watertank for a phantom, according to the first embodiment of the present invention.

FIG. 2 is a diagram illustrating a watertank for a phantom, according to the first embodiment of the present invention.

In the present example, as illustrated in FIG. 2, transparent windows are formed at eight positions on a side wall of a watertank whose walls are made of black acrylic plate. These transparent windows are made of clear acrylic plate. The watertank is filled with an intralipid aqueous solution (ten-times diluted intralipid aqueous solution at a 10 percent concentration). In other words, the pseudo live subject used in the first variation is intralipid aqueous solution.

More specifically, black ink is dripped into the intralipid aqueous solution filling the watertank to the degree of about 20 parts per million (ppm). Accordingly, an absorption coefficient and scattering coefficient that are almost equivalent to those of a live subject can be achieved. Then, a black light absorber simulating the bloodstream is sunk into the whitish intralipid aqueous solution. In the present example, the light absorber is black polyacetal, and has an approximately 5 millimeters (mm) spherical body in diameter. In order to control the position of such a spherical body, the spherical body is attached to a thin 1 mm metallic rod in diameter, and the rod is connected to an automatic positioning stage. A probe is precisely aligned to each of the transparent windows of the watertank, and is attached thereto.

In the present example, the volume of the watertank is 140 mm×140 mm×60 mm. The thickness of the black acrylic plate is 4 mm. The eight transparent windows are composed of circular transparent windows A and B with varying two sizes (see FIG. 3). There are four transparent windows A and four transparent windows B. The diameter of the transparent window A is 9 mm, and the diameter of the transparent window A is 12 mm. The thickness of both the transparent windows A and B is 1.5 mm.

Figure 3:
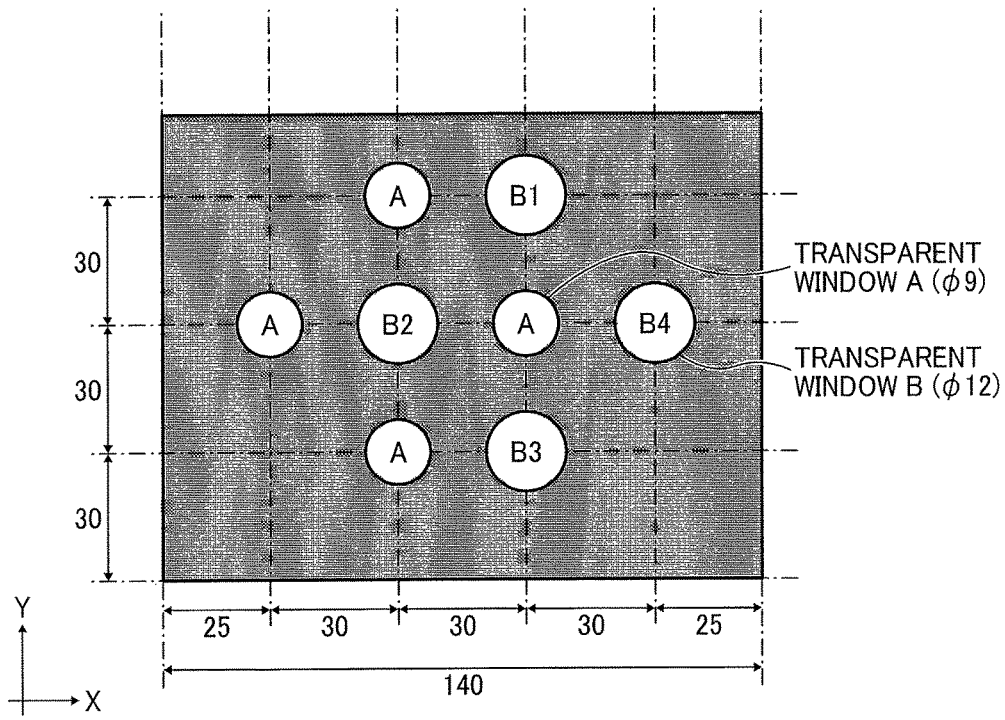
FIG. 3 is a diagram illustrating the layout of a transparent window according to the first embodiment of the present invention.

FIG. 3 illustrates the layout of the eight transparent windows according to the present embodiment.

The eight transparent windows are arranged at even intervals in the X-axis direction and the Y-axis direction like a grid such that the transparent windows A and the transparent windows B are next to each other in an alternating manner. In the present example, the detection module DM is attached to each of the transparent windows A, and the light source module LM is attached to each of the transparent windows B (B1 to B4). The distance between the centers of the two neighboring transparent windows is 30 mm.

Figure 4:
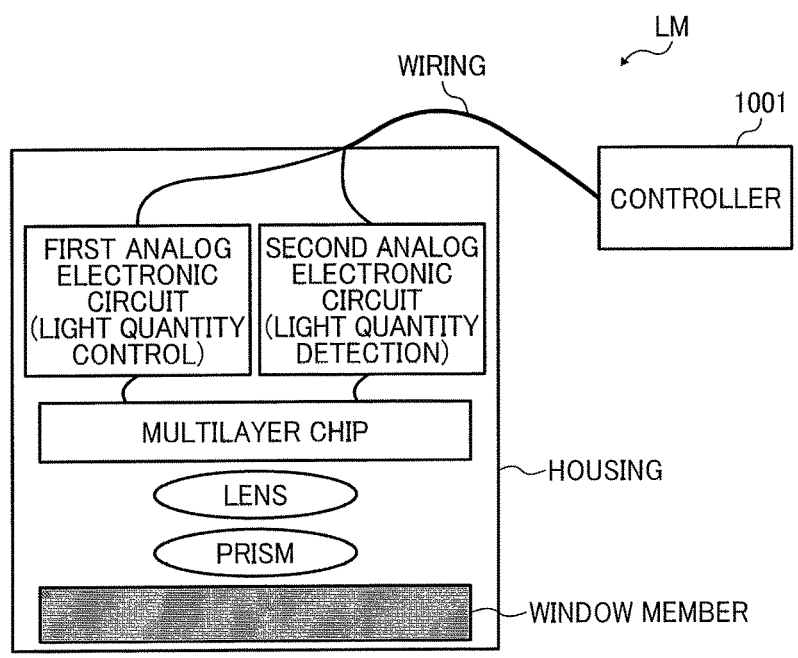
FIG. 4 is a first diagram illustrating a general configuration of a light source module according to a first variation of the first embodiment of the present invention.

As illustrated in FIG. 4, the light source module LM includes, for example, a ceramic package for which a lens, a prism, and a multilayer chip including a surface-emitting laser element and a photo-sensing element are provided, a flexible circuit board on which the ceramic package and first and second analog electronic circuits are mounted, a wiring connected to the flexible circuit board, a connector, a housing accommodating these elements, a window member consisting of transparent resin that contacts the test object. Note that the surface-emitting laser element and the photo-sensing element are optically coupled to the multilayer chip.

The second analog electronic circuit is used to detect light quantity, and includes an amplifier circuit. The second analog electronic circuit is coupled to the photo-sensing element, and performs analog-digital conversion on the quantity of light escaping from the surface-emitting laser element. Here, the quantity of light is detected by the photo-sensing element. Accordingly, the light quantity value of a turned-on surface-emitting laser element can be detected. The second analog electronic circuit sends the detected light quantity value to the controller 1001 through the wire. The controller 1001 calculates an optimal light quantity value, and sends through the wire a current value that corresponds to the calculated optimal light quantity value to the first analog electronic circuit that functions to control the light quantity. Due to the first analog electronic circuit, the surface-emitting laser element can emit a desired quantity of light.

Figure 44:
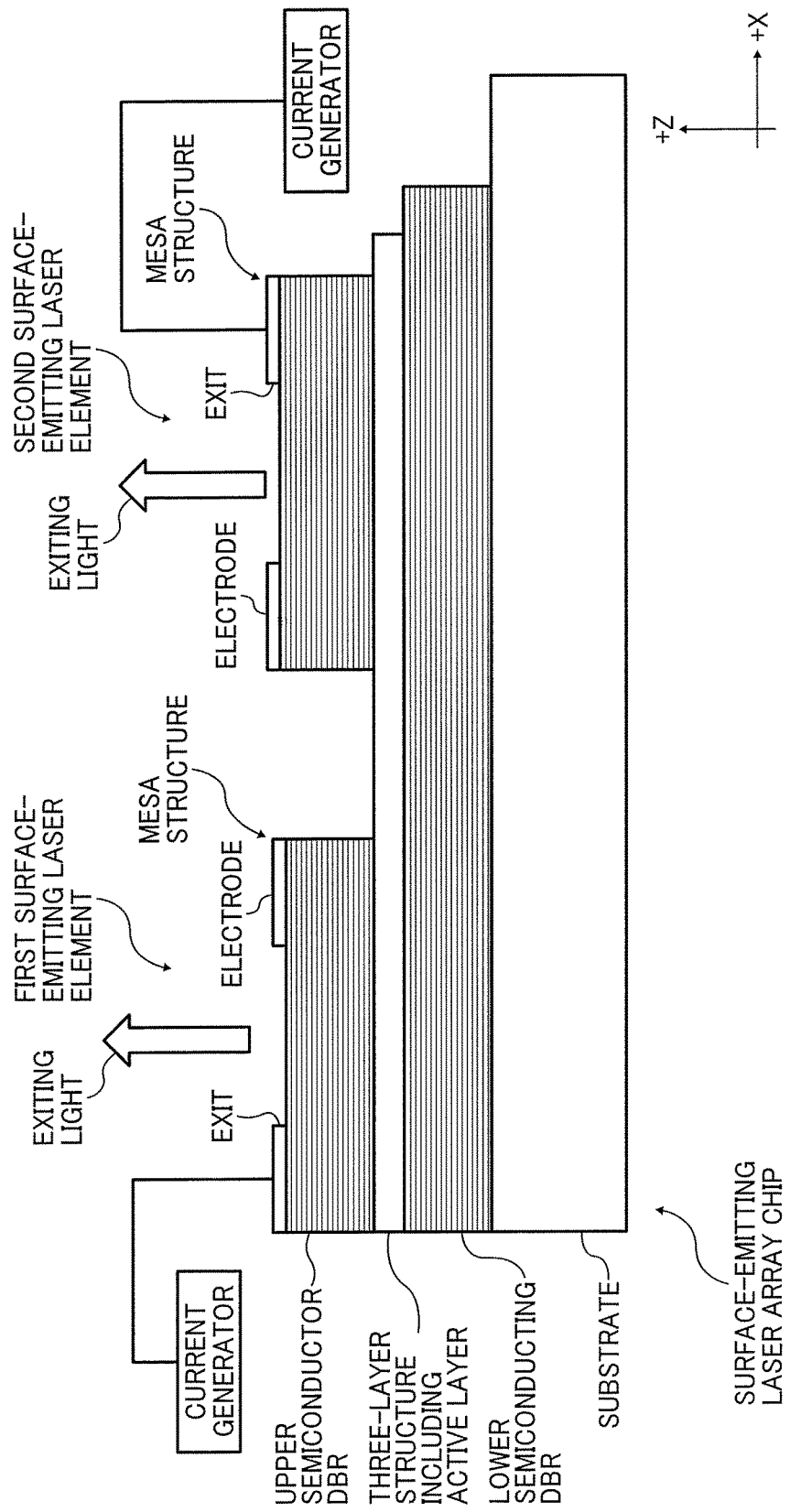
FIG. 44 is a diagram illustrating the sectional view of a surface-emitting laser array chip according to a control sample.

FIG. 44 is a diagram illustrating the sectional view of a surface-emitting laser array chip according to a control sample.

As illustrated in FIG. 44, the surface-emitting laser array chip according to the present control sample has a multi-layered structure including a first surface-emitting laser element and a second surface-emitting laser element. Each of the first surface-emitting laser element and the second surface-emitting laser element has a mesa structure. Such a mesa structure of the first and second surface-emitting laser elements is formed by etching a layered product that includes, for example, a substrate, a lower semiconducting distributed Bragg reflector (DBR), a three-layer structure, an upper semiconductor DBR, and an electrode. Note that the three-layer structure includes a lower spacer layer, an active layer, and an upper spacer layer. The layered product is etched from the upper semiconductor DBR side, and such etching of the layered product reaches, at least, the lower spacer layer. In the following description, it is assumed that the surface-emitting laser elements emit light in the +Z direction.

The substrate according to the present control sample is an n-GaAs single-crystal substrate with polished specular surface where the normal-line direction of the polished specular surface is inclined towards a crystal orientation [111] A by 15 degrees ($\theta$=15 degrees) with reference to a crystal orientation [100]. In the present control sample, the substrate is arranged such that the crystal orientations [0-11] and [01-1] are the +X direction and the −X direction, respectively.

The lower semiconducting DBR includes 37.5 pairs of a low refractive index layer that is composed of n-$Al_{0.9}Ga_{0.1}As$ and is stacked on the surface of the substrate through a buffer layer and a high refractive index layer composed of n-$Al_{0.3}Ga_{0.7}As$.

Between two layers of varying refractive indexes, a gradient-composition layer with the thickness of 20 nm where the composition gradually changes from one side of the composition to the other side of the composition is provided in order to reduce the electrical resistance. Each of the layers of varying refractive indexes is designed to include one-half of the adjacent gradient-composition layer and have the optical thickness of $\lambda/4$ when it is assumed that the oscillation wavelength is $\lambda$. Note also that the optical thickness and the actual thickness of the layer has the following relations. When the optical thickness is $\lambda/4$, the actual thickness of the layer is D=$\lambda/4N$ (where N denotes the refractive index of the medium of that layer). Between two layers of varying refractive indexes, a gradient-composition layer where the composition gradually changes from one side of the composition to the other side of the composition is provided in order to reduce the electrical resistance.

The lower spacer layer is stacked on the lower semiconducting DBR on the +Z side, and is composed of non-doped $Al_{0.6}Ga_{0.4}As$. Alternatively, the lower spacer layer may be composed of, for example, InGaAsP.

The active layer is stacked on the lower spacer layer on the +Z side, and has three quantum well layers and four barrier layers. The quantum well layers are composed of $Al_{0.12}Ga_{0.88}As$, and the barrier layers are composed of $Al_{0.3}Ga_{0.7}As$. Alternatively, the active layer may be composed of a GaInAsP material.

The upper spacer layer is stacked on the active layer on the +Z side, and is composed of non-doped $Al_{0.6}Ga_{0.4}As$. The portion consisting of the lower spacer layer, the active layer, and the upper spacer layer is referred to as a resonator structure, and is designed to have the optical thickness of one wavelength. The active layer is disposed in the center of the resonator structure so as to achieve a high stimulated-emission rate. Note that the center of the resonator structure corresponds to a belly of the standing-wave distribution of the electric field.

The upper semiconductor DBR is stacked on the upper spacer layer on the +Z side, and includes twenty-four pairs of a low refractive index layer composed of p-$Al_{0.9}Ga_{0.1}As$ and a high refractive index layer composed of p-$Al_{0.3}Ga_{0.7}As$. Between two layers of varying refractive indexes, a gradient-composition layer where the composition gradually changes from one side of the composition to the other side of the composition is provided in order to reduce the electrical resistance. Each of the layers of varying refractive indexes is designed to include one-half of the adjacent gradient-composition layer and have the optical thickness of $\lambda/4$ when it is assumed that the oscillation wavelength is $\lambda$. At a position that is optically $\lambda/4$ away from the resonator structure of the upper semiconductor DBR, a to-be-selected oxidized layer composed of p-AlAs is disposed.

On the top surface of the upper semiconductor DBR, a metal electrode with slot or an alloy electrode with slot is formed.

In the surface-emitting laser array chip according to the present control sample, the two sections with mesa structure that are disposed on the same substrate are the first surface-emitting laser element and the second surface-emitting laser element, and an electrode of each of the first surface-emitting laser element and the second surface-emitting laser element is connected to a different current generator and the hole of the electrode serves as an exit.

Figure 45:
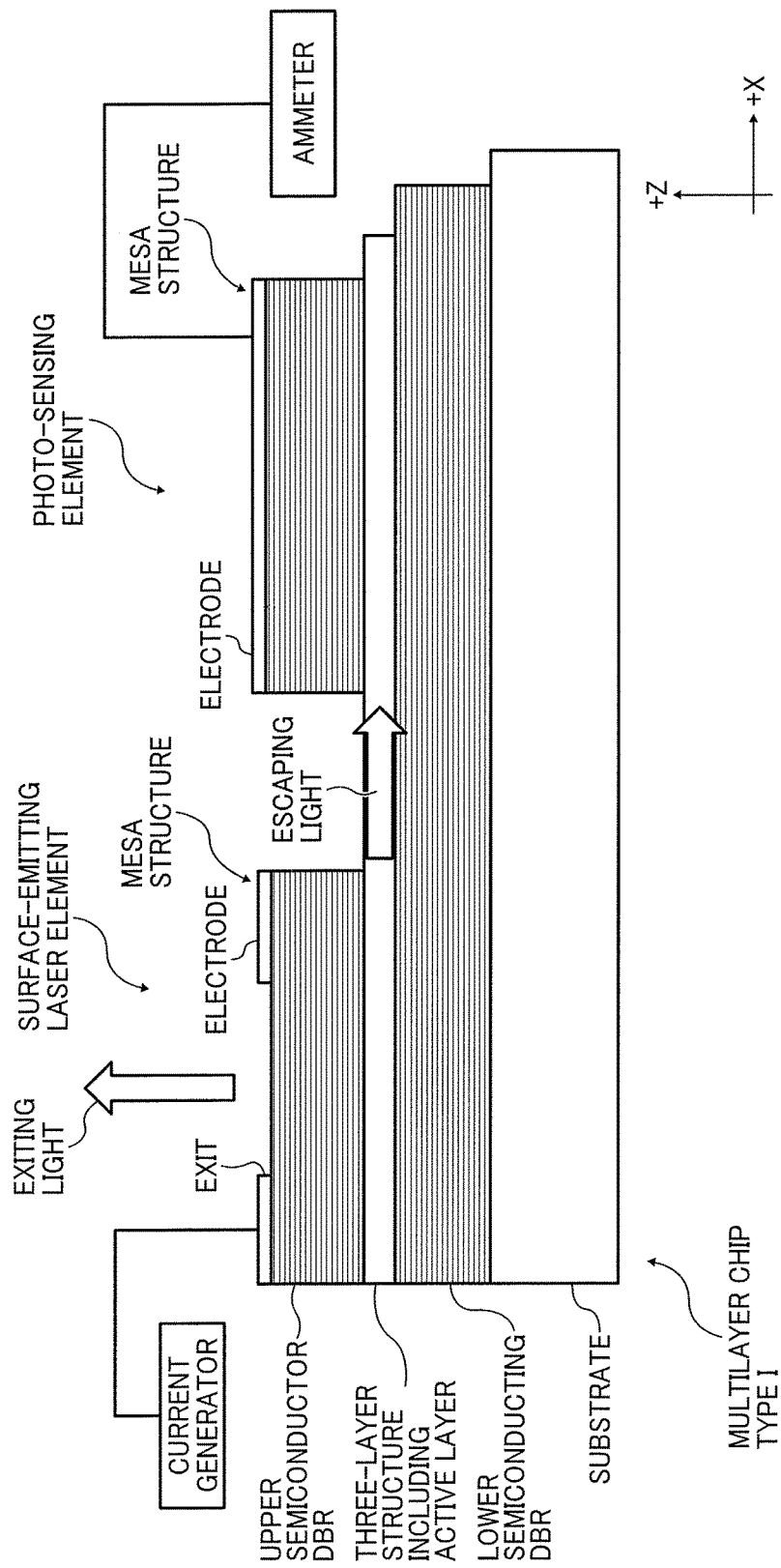
FIG. 45 a sectional view of a multilayer chip (type I) according to the first variation of the first embodiment.

FIG. 45 a sectional view of a multilayer chip (type I) according to the first variation of the first embodiment.

By contrast, as illustrated in FIG. 45, the multilayer chip (type I) according to the first variation of the first embodiment has a layer structure similar to the surface-emitting laser array chip of the above control sample, and also has two sections with mesa structure that are disposed on the same substrate. One of the two sections serves as a surface-emitting laser element where an electrode is connected to a current generator and the hole of the electrode serves as an exit, and the other section serves as a photo-sensing element that detects the light escaping from the surface-emitting laser element. In the photo-sensing element, an electrode is not connected to a current generator but is connected to an ammeter.

In such a configuration, the light that has propagated from the active layer of the surface-emitting laser element (escaping light) is converted into electrons (photoelectric conversion) by the photo-sensing element, and the converted electrons flow through the ammeter and are detected as a current value.

Figure 46:
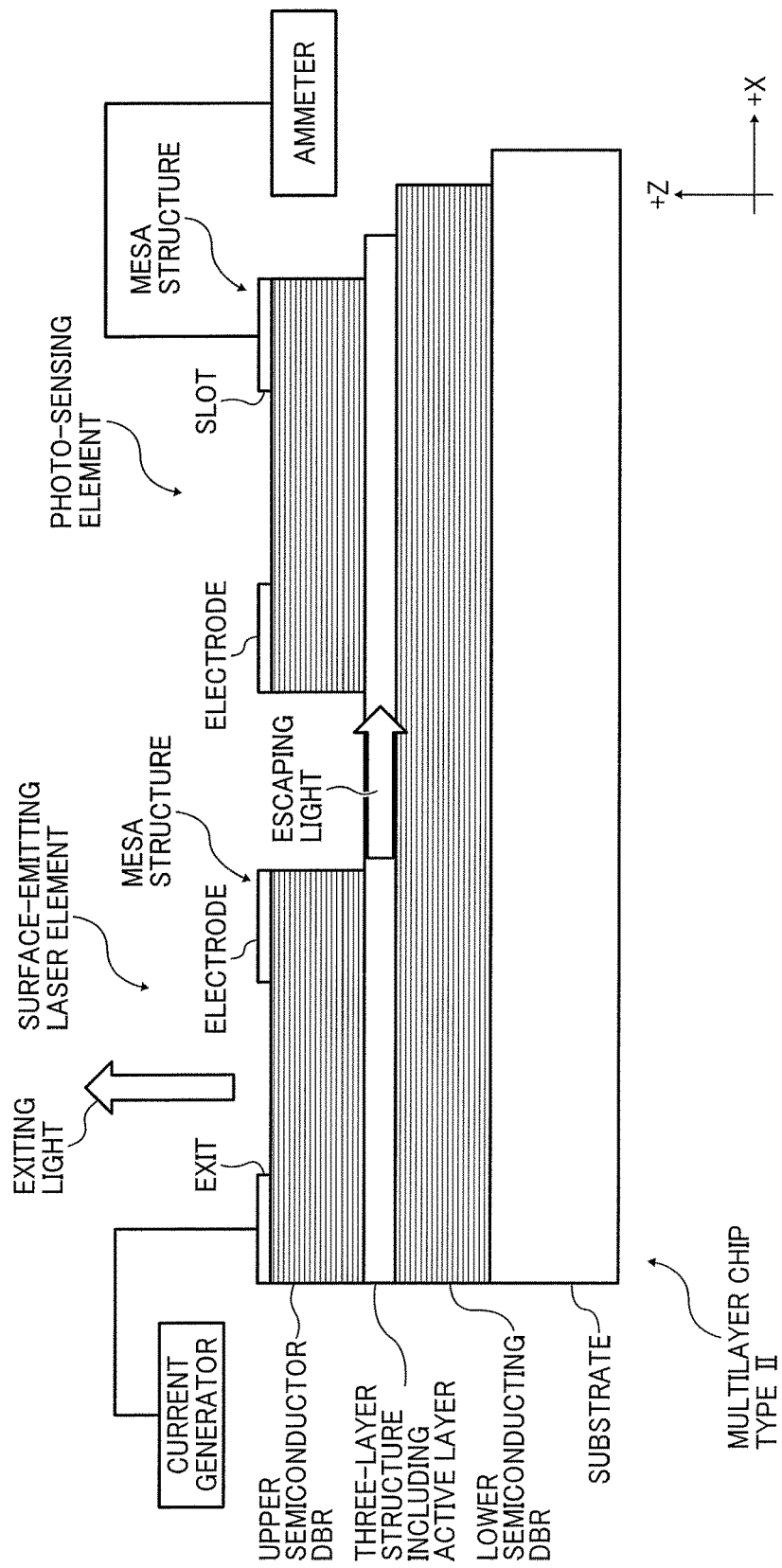
FIG. 46 a sectional view of a multilayer chip (type II) according to the second variation of the first embodiment.

FIG. 46 a sectional view of a multilayer chip (type II) according to the second variation of the first embodiment.

As in the multilayer chip (type II) of FIG. 46 according to the second variation of the first embodiment, it is desired that a slot be formed on an electrode of the photo-sensing element. If such a slot is formed on an electrode, the light that enters the photo-sensing element from above can be detected.

Due to this configuration, in addition to the monitoring of the light quantity escaping from the adjacent surface-emitting laser element, the photo-sensing element may be used to monitor, for example, a contact state between the light source module LM and a test object.

Figure 47:
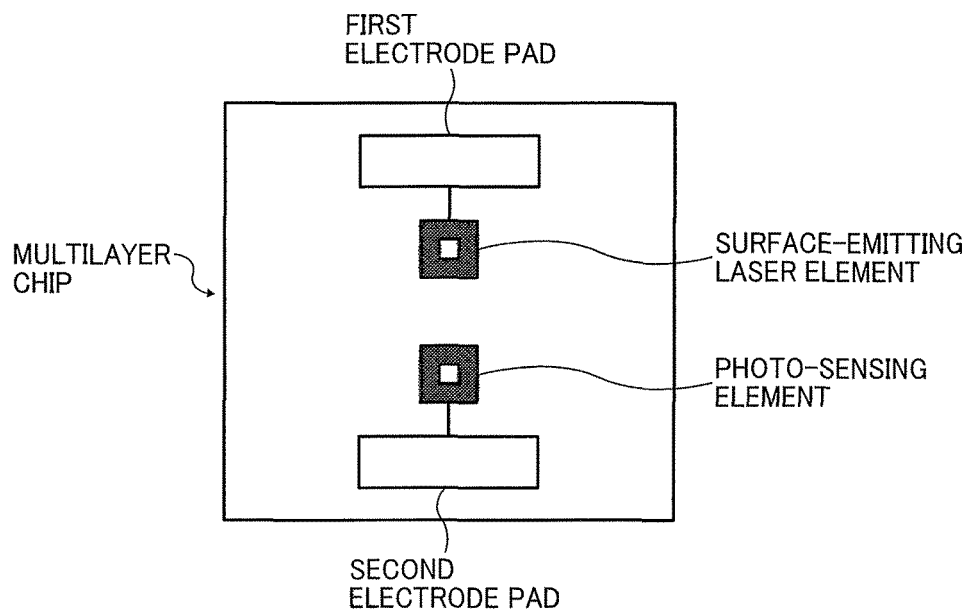
FIG. 47 is a top view of the multilayer chip (type II) of FIG. 46.

FIG. 47 is a top view of the multilayer chip (type II) of FIG. 46.

As illustrated in FIG. 46, the surface-emitting laser element and the photo-sensing element are arranged in parallel. Moreover, an electrode pad is formed on each of the surface-emitting laser element and the photo-sensing element, and the electrode pads are connected to a printed wiring board or the like by wire bonding.

Figure 48:
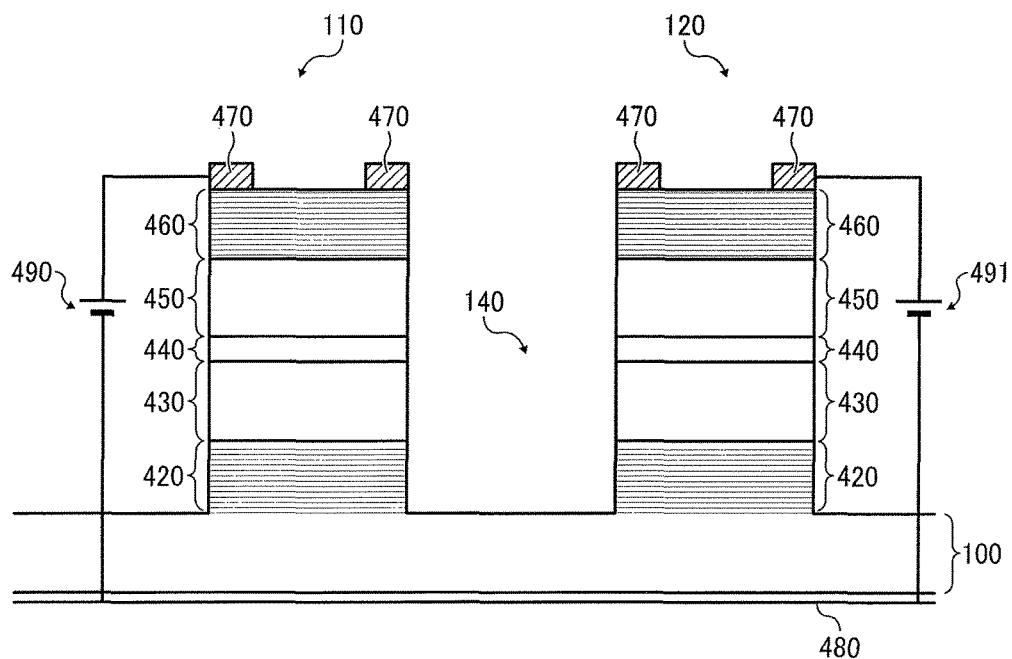
FIG. 48 is a diagram illustrating a first related art device.
Figure 49:
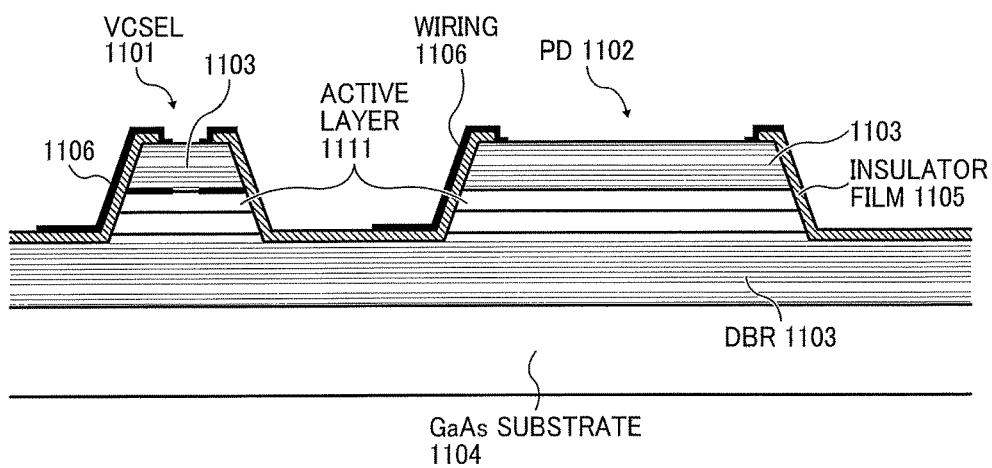
FIG. 49 is a diagram illustrating a second related art device.

FIG. 48 and FIG. 49 are diagrams illustrating the first and second related art examples of a light-quantity monitoring method using a surface-emitting laser element, where an element adjacent to the surface-emitting laser element is used as a light-quantity monitoring element.

In a first related art device illustrated in FIG. 48, etching is done from the top to the lower reflecting mirror, and the light that escapes from the active layer of the surface-emitting laser element enters the active layer of the adjacent element via the airspace.

In a second related art device illustrated in FIG. 49, a slot is formed on the top side of the photodiode, and the incident light from above is absorbed in the photodiode.

Figure 50:
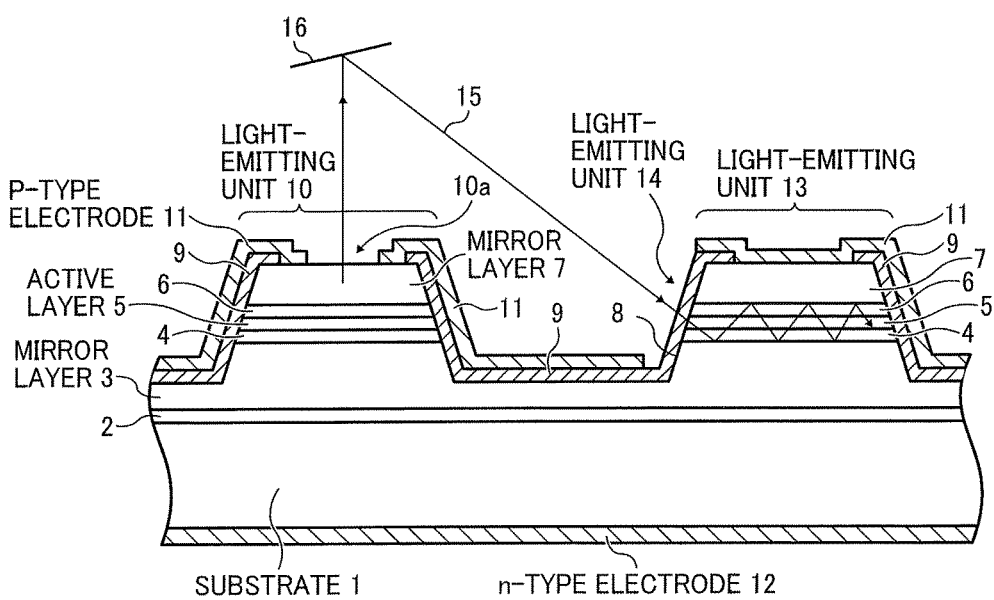
FIG. 50 is a diagram illustrating a third related art device.

FIG. 50 is a diagram illustrating a third related art device.

In the third related art device (see JP-H09-083084-A) illustrated in FIG. 50A, some of the light exiting from the surface-emitting laser element is reflected towards an edge of the mesa structure of an adjacent element, and the reflected light is absorbed in the adjacent element.

In any of the first to third related art, the surface-emitting laser element is not optically connected to an adjacent element, and thus the quantity of light that propagates from the surface-emitting laser element to the adjacent element decreases and the accuracy of monitoring deteriorates.

By contrast, as illustrated in FIG. 45 and FIG. 46, in the multilayer chip (type I) and the multilayer chip (type II) according to the first variation of the first embodiment, the surface-emitting laser element is connected to the photo-sensing element (adjacent element) via, at least, the lower spacer layer. In other words, the surface-emitting laser element is optically connected to the photo-sensing element. In this configuration, the quantity of light that propagates from the surface-emitting laser element to the photo-sensing element increases, and the accuracy of the monitoring improves.

Figure 51:
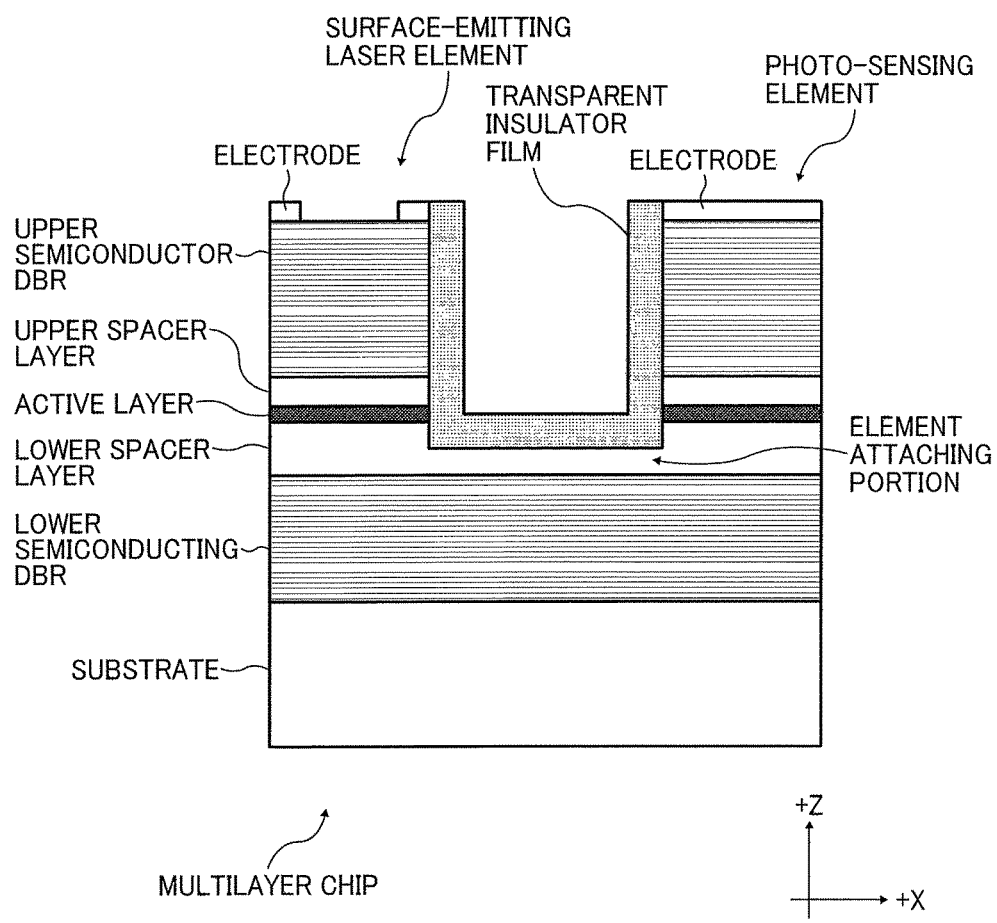
FIG. 51 is a detailed sectional view of a multilayer chip according to the first variation of the first embodiment.

FIG. 51 is a detailed sectional view of the multilayer chip according to the first variation of the first embodiment.

In FIG. 51, the lower spacer layer and the upper spacer layer that sandwich the active layer are illustrated. The mesa structure of the surface-emitting laser element and the mesa structure of the photo-sensing element are formed by etching the above-described layered product from its top surface to inside the lower spacer layer.

In such a configuration, the light that escapes from the surface-emitting laser element propagates to the photo-sensing element through the lower spacer layer that connects surface-emitting laser element to the photo-sensing element. Hereinafter, a portion of the lower spacer layer that connects the surface-emitting laser element to the photo-sensing element is referred to as an element attaching portion.

On the top surface of the element attaching portion and the sides of the surface-emitting laser element and the photo-sensing element that face each other, a transparent insulator film is formed. Such a transparent insulator film is formed by performing chemical-vapor deposition (CVD) or sputtering on, for example, silicon dioxide ($SiO_2$) or silicon mononitride (SiN). The optical thickness of the transparent insulator film is about several hundred nanometer (nm).

Figure 52:
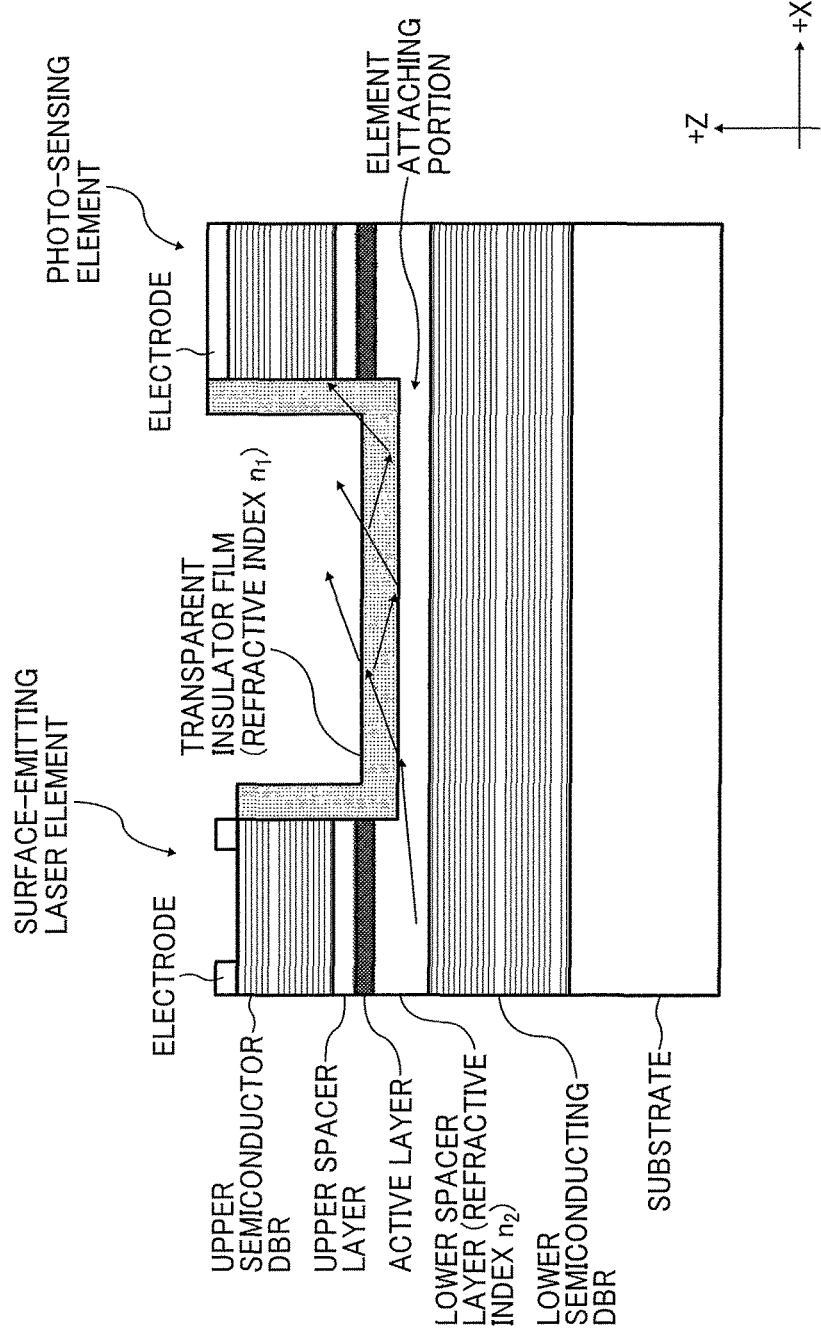
FIG. 52 is a diagram illustrating an example where the light escaping from a surface-emitting laser element disperses, according to the first variation of the first embodiment.

FIG. 52 is a diagram illustrating an example where the light escaping from the surface-emitting laser element disperses, according to the first variation of the first embodiment.

Here, it is assumed that the refractive index of the transparent insulator film formed by SiN or $SiO_2$ is, for example, $n_1$ and the refractive index of the lower spacer layer formed by InGaAsP is, for example, $n_2$. When $n_1 \geq n_2$ and the optical thickness of the transparent insulator film is thinner than oscillation wavelength $\lambda$, as illustrated in FIG. 52, the light that escapes from the surface-emitting laser element enters the transparent insulator film whose refractive index is relatively high, and then some of the light propagates through the transparent insulator film. However, the remaining light is not trapped within the transparent insulator film but escapes to the outside.

Figure 53:
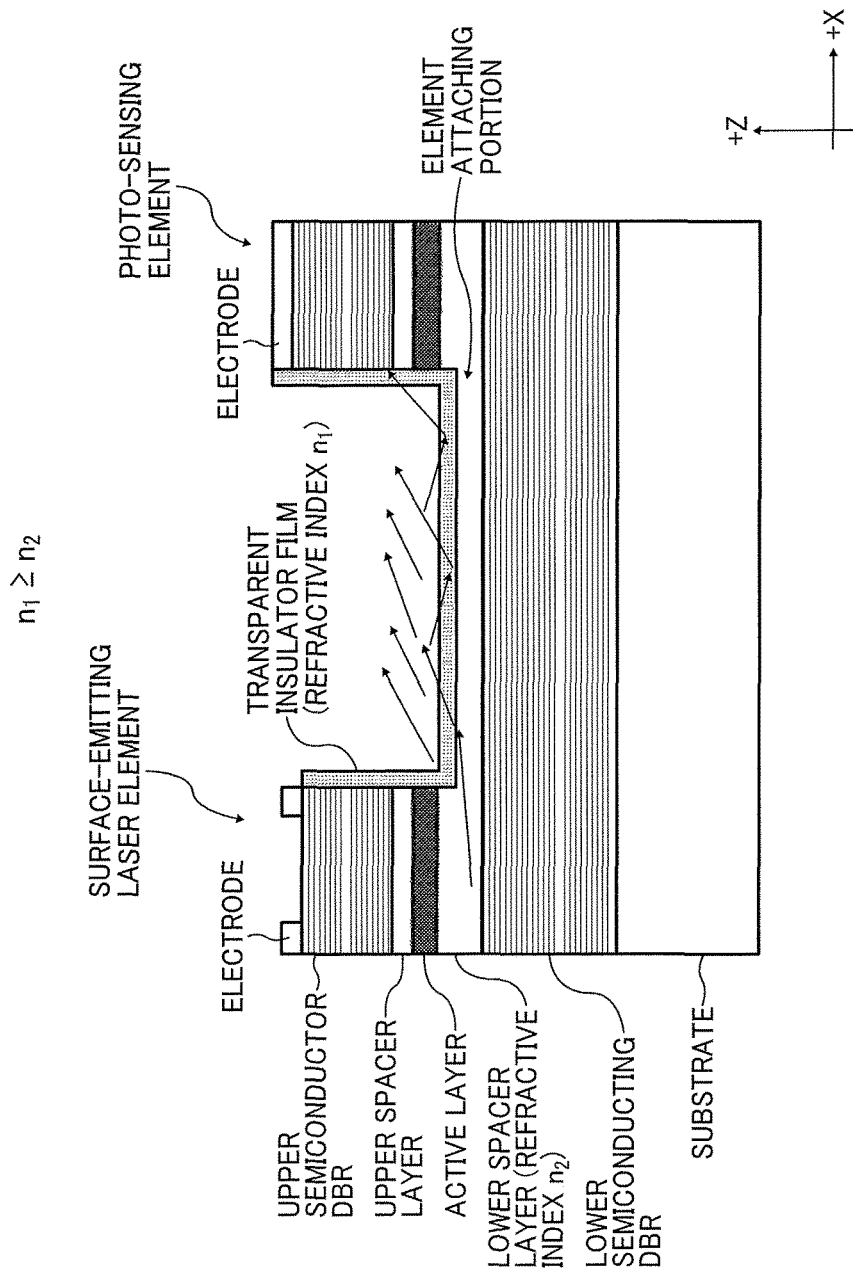
FIG. 53 is a diagram illustrating another example where the light escaping from a surface-emitting laser element disperses, according to the first variation of the first embodiment.

FIG. 53 is a diagram illustrating another example where the light escaping from the surface-emitting laser element disperses, according to the first variation of the first embodiment.

Figure 54:
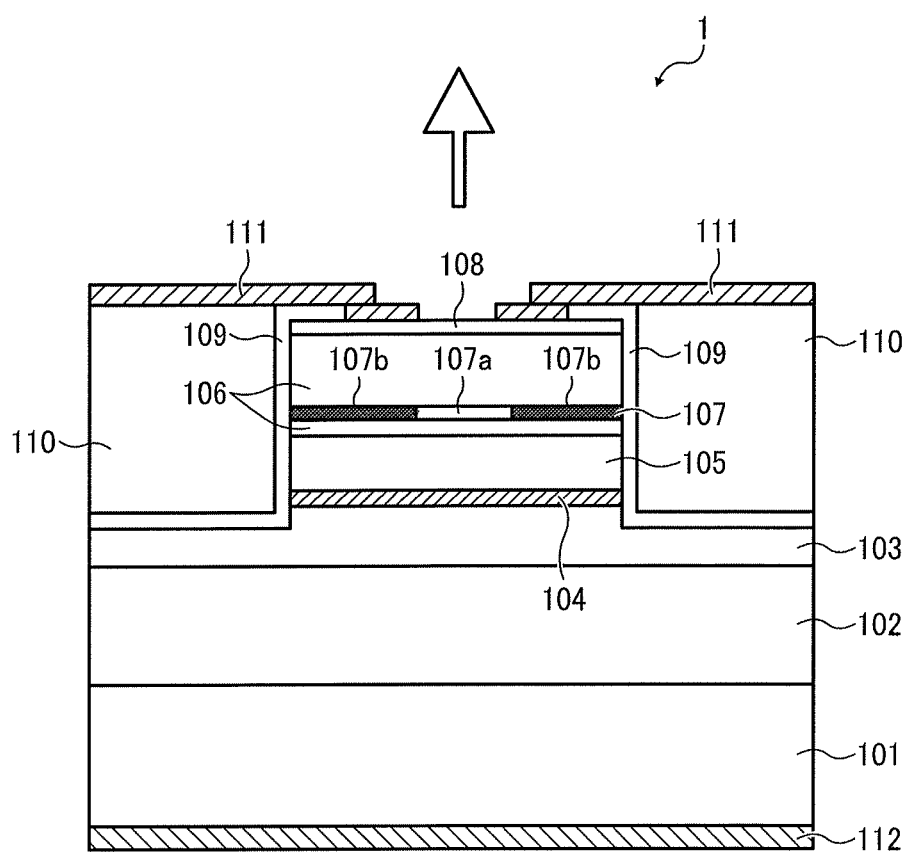
FIG. 54 is a diagram illustrating a fourth related art device.

FIG. 54 is a diagram illustrating a fourth related art device.

The example FIG. 53 is similar to the fourth related art device illustrated in FIG. 54, and $n_1 \geq n_2$ and the optical thickness of the transparent insulator film is far thinner than oscillation wavelength $\lambda$. Accordingly, most of the light that has entered the transparent insulator film is dispersed.

Figure 55:
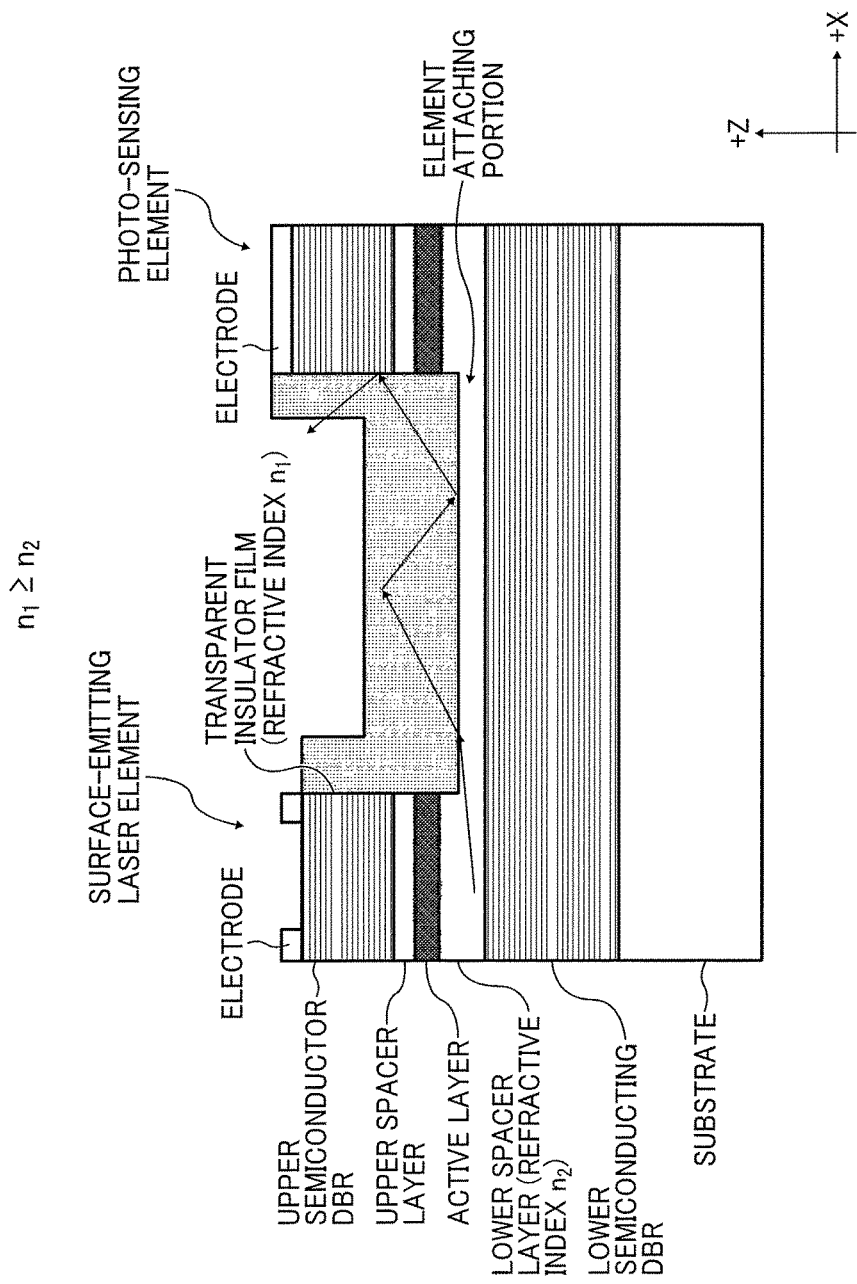
FIG. 55 is a diagram illustrating an example where the light escaping from a surface-emitting laser element is reflected by a photo-sensing element and exits from a multilayer chip, according to the first variation of the first embodiment.

FIG. 55 is a diagram illustrating an example where the light escaping from the surface-emitting laser element is reflected by the photo-sensing element and exits from the multilayer chip, according to the first variation of the first embodiment.

As illustrated in FIG. 55, when $n_1 \geq n_2$ and the optical thickness of the transparent insulator film is thicker than the oscillation wavelength $\lambda$, the propagating light is reflected by the edge (side) of the photo-sensing element and exits from the multilayer chip.

In view of the above circumstances, when $n_1 \geq n_2$, it is desired that the optical thickness of the transparent insulator film be equivalent to the oscillation wavelength $\lambda$.

Figure 56:
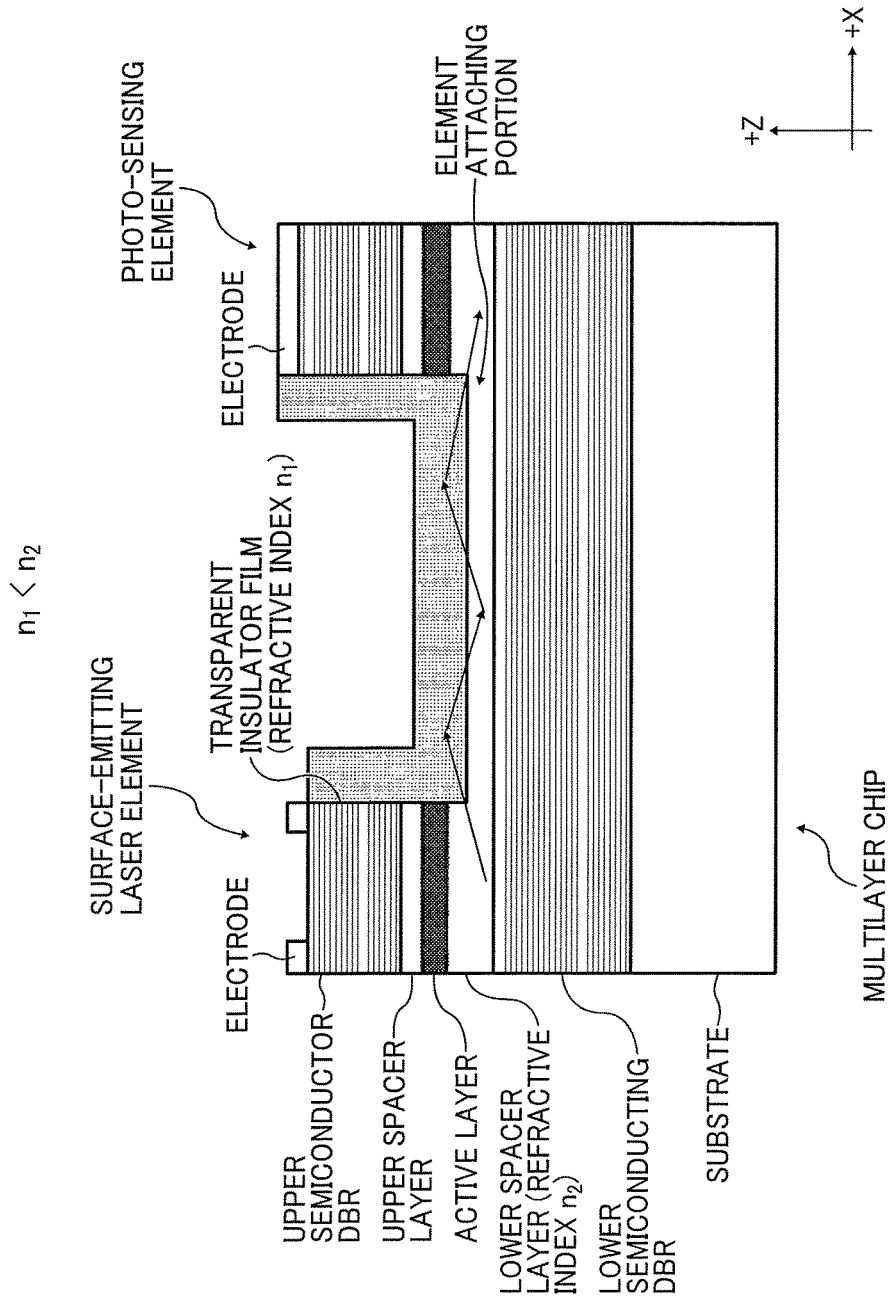
FIG. 56 is a first diagram illustrating an effect of a multilayer chip according to the first variation of the first embodiment.

FIG. 56 is a first diagram illustrating an effect of the multilayer chip according to the first variation of the first embodiment.

By contrast, when $n_1 < n_2$ as illustrated in FIG. 56, the light that escapes from the surface-emitting laser element mainly propagates through the lower spacer layer whose refractive index is relatively high. However, when the optical thickness of the element attaching portion is thinner than oscillation wavelength $\lambda$, the light escapes to the transparent insulator film while propagating through the lower spacer layer.

In view of the above circumstances, when $n_1 < n_2$ and the optical thickness of the element attaching portion $<\lambda$, it is desired that the optical thickness of the element attaching portion and the transparent insulator film in total be equivalent to the oscillation wavelength $\lambda$.

On the other hand, when $n_1 \geq n_2$ and the optical thickness of the element attaching portion $\geq \lambda$, most of the light that propagates through the lower spacer layer is not escaping to the transparent insulator film. For this reason, it is desired that the optical thickness of the element attaching portion be equivalent to the oscillation wavelength $\lambda$.

In view of the above circumstances, it is desired that the optical thickness of a light-propagating region between the surface-emitting laser element and the photo-sensing element be equivalent to the oscillation wavelength $\lambda$.

In such a configuration, regardless of whether $n_1 \geq n_2$ or $n_1 < n_2$, the light that escapes from the surface-emitting laser element can efficiently be propagated to the photo-sensing element, and the quantity of escaping light can be monitored with a high degree of precision.

Accordingly, the quantity of light exiting from the surface-emitting laser element (i.e., the quantity of irradiation light towards a test object) can be controlled with a high degree of precision, and the accuracy of the measurement of the internal information of the test object improves. Accordingly, light absorbers (for example, cerebral blood flow) can be detected with precision.

Figure 57:
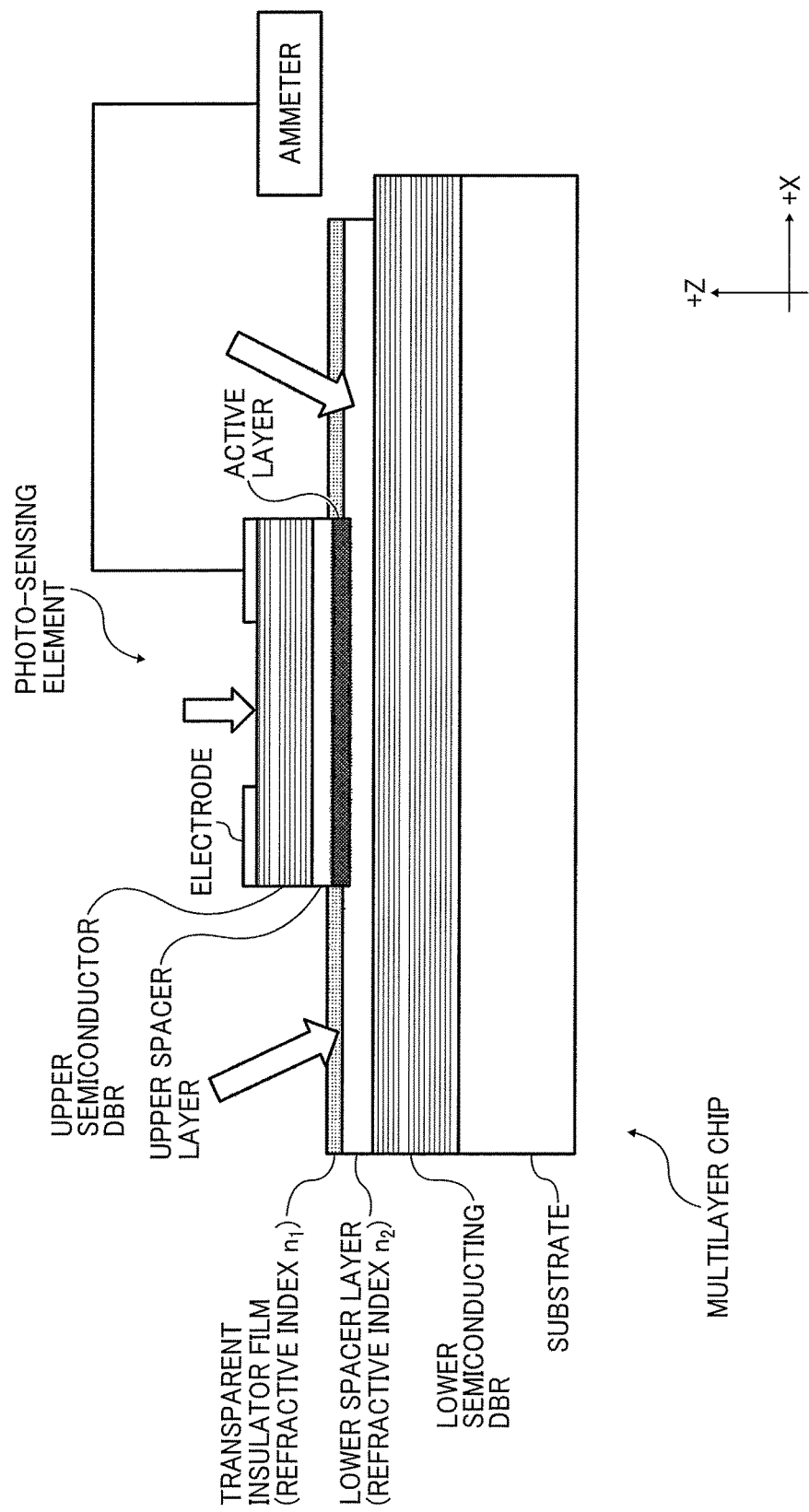
FIG. 57 is a second diagram illustrating an effect of a multilayer chip according to the first variation of the first embodiment.

FIG. 57 is a second diagram illustrating an effect of the multilayer chip according to the first variation of the first embodiment.

In contrast to the example illustrated in FIG. 45, a slot is formed on an electrode of the photo-sensing element in the example illustrated in FIG. 57. Through the slot, the light from above can be taken in the photo-sensing element.

In the example of FIG. 57, light from obliquely upward enters the photo-sensing element through the transparent insulator film. In a similar manner to the above, the transparent insulator film cannot efficiently propagate the light if the transparent insulator film is not as thick as the oscillation wavelength $\lambda$.

Figure 58:
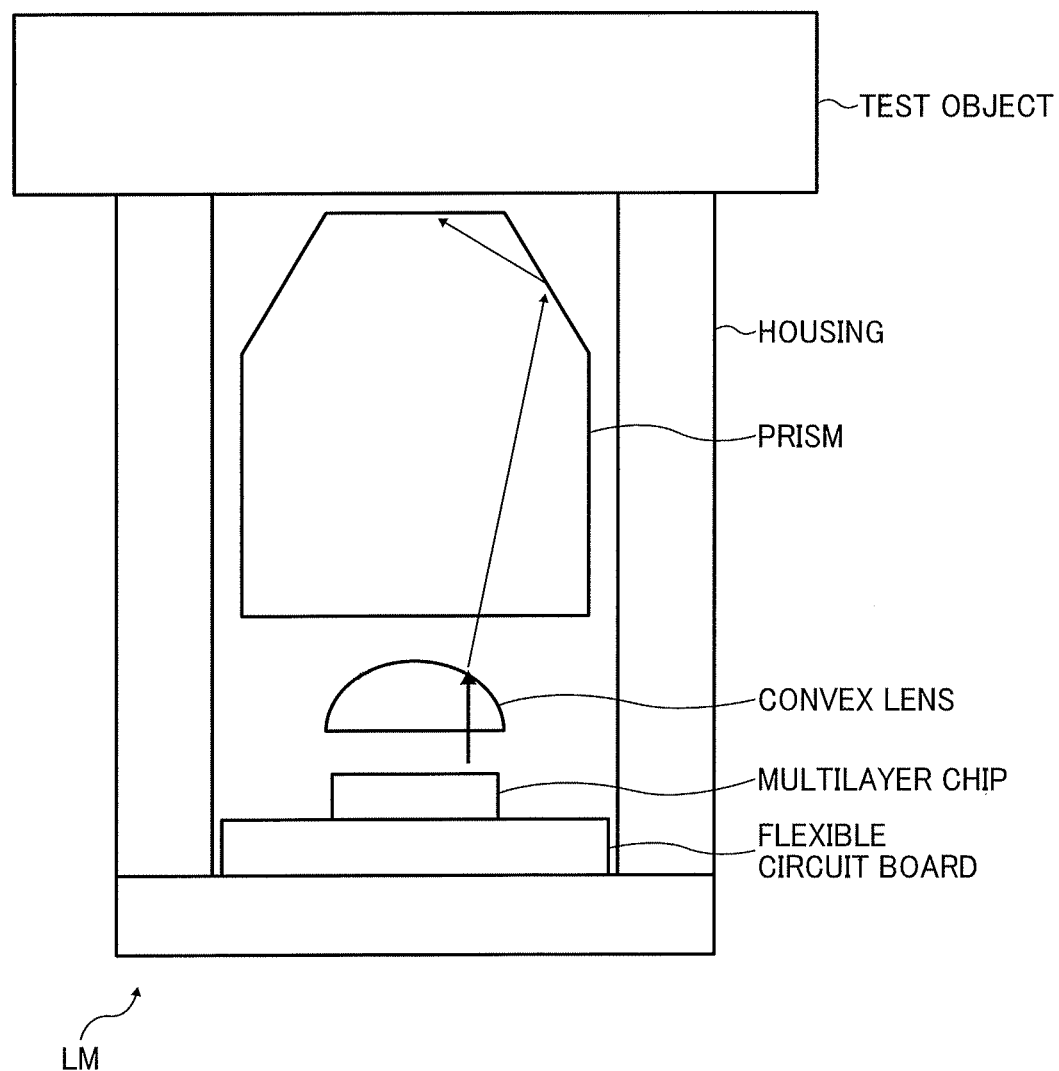
FIG. 58 is a diagram illustrating an optical path of the light emitted from a surface-emitting laser element, according to the first embodiment.

FIG. 58 is a diagram illustrating an optical path of the light emitted from the surface-emitting laser element, according to the present embodiment.

When optical elements such as a lens or prism are arranged above the multilayer chip in the light source module LM as illustrated in FIG. 58, light from obliquely upward heads for the photo-sensing element as in the example of FIG. 57. In such a configuration, the directions of travel of the light emitted from the surface-emitting laser element of the multilayer chip are changed by the lens and the prism before the light enters the test object. How the light that returns to the multilayer chip (return light) significantly differs between a configuration in which the light source module LM is not attached to a test object (see FIG. 59) and a configuration in which the light source module LM is attached to a test object (see FIG. 60).

Figure 59:
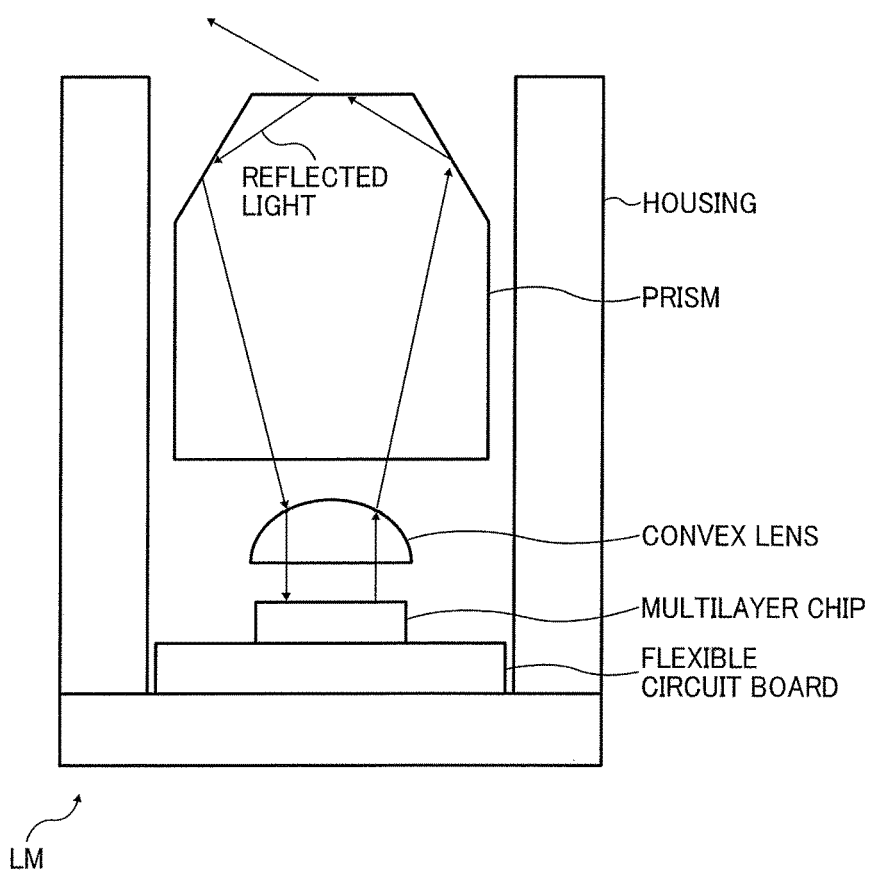
FIG. 59 is a diagram illustrating an optical path of the light emitted from a surface-emitting laser element, and an optical path of the light reflected at the exit end of a prism, according to the first embodiment.

FIG. 59 is a diagram illustrating an optical path of the light emitted from the surface-emitting laser element, and an optical path of the light reflected at the exit end of the prism, according to the present embodiment.

When the light source module LM is not attached to a test object as illustrated in FIG. 59, only a small quantity of reflection light returns to a certain point of the multilayer chip through the prism or the lens.

Figure 60:
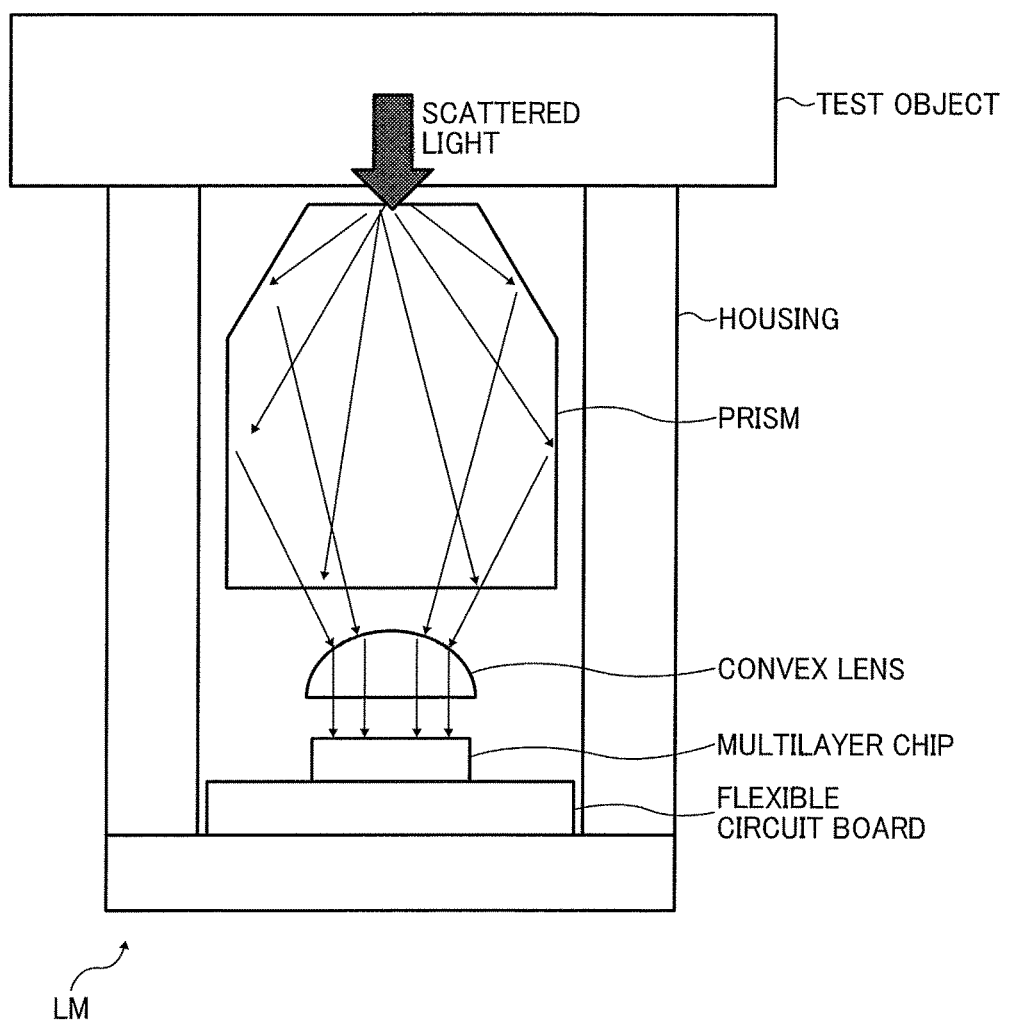
FIG. 60 is a diagram illustrating optical paths of the light that is scattered from a test object and heads for a multilayer chip.

FIG. 60 is a diagram illustrating optical paths of the light that is scattered from a test object and heads for the multilayer chip.

By contrast, when the light source module LM is attached to a test object as illustrated in FIG. 60, in addition to the above-described reflection light, light rays that are scattered in various directions (scattered light) return to the multilayer chip. In order to handle such a situation, the return light is detected by the photo-sensing element as illustrated in FIG. 57, and a difference between the reflection light as illustrated in FIG. 59 and the scattered light as illustrated in FIG. 60 is identified. By performing such an identification function, the information about a state of contact between the light source module LM and a live subject can be obtained. More specifically, the detected scattered light and the detected reflection light are compared with each other to obtain information about a state of contact between the light source module LM and a live subject. Then, the state of attachment between the light source module LM and the live subject can be improved based on the obtained information about the state of contact. Further, the internal information of a test object (for example, the position information of a light absorber) can be obtained with a high degree of precision. For example, when the reflection light is dominant, it is determined that the state of attachment is bad, and when the scattered light is dominant, it is determined that the state of attachment is good.

Figure 61:
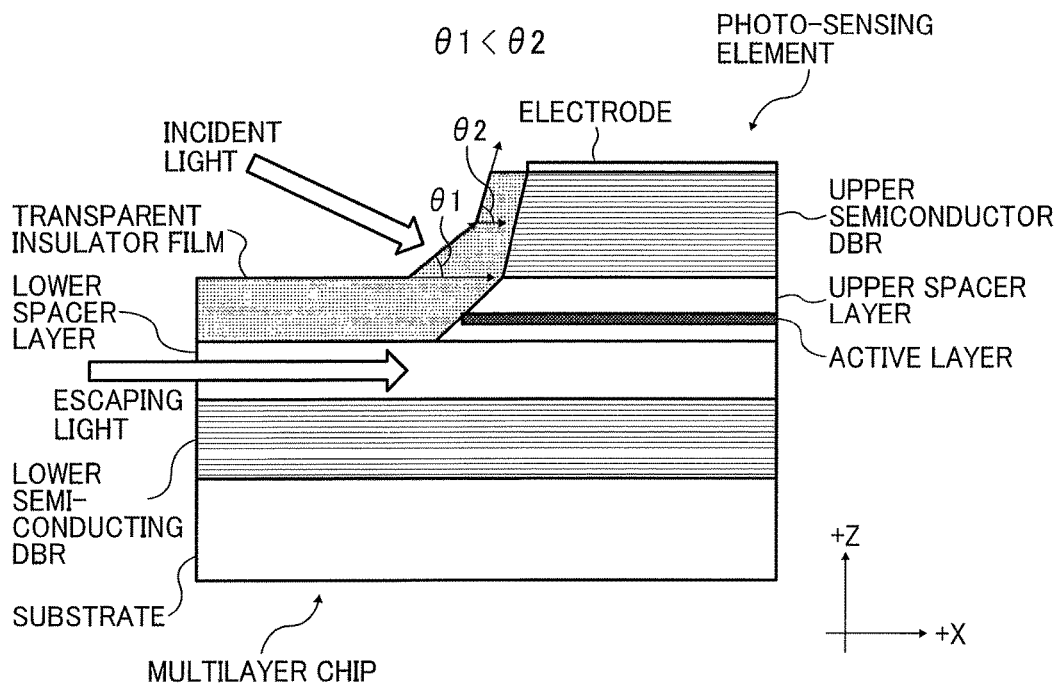
FIG. 61 is a diagram illustrating the tilt angle of a side of the mesa structure of a photo-sensing element, according to the first embodiment.

FIG. 61 is a diagram illustrating the tilt angle of a side of the mesa structure of the photo-sensing element, according to the present embodiment.

In the example illustrated in FIG. 61, a side of the mesa structure of the photo-sensing element is not vertical but is inclined. In a similar manner, a side of the mesa structure of the surface-emitting laser element is also inclined.

In the mesa structure, the tilt angle θ1 of the side of the upper spacer layer, the active layer, and the lower spacer layer is different from the tilt angle θ2 of the side of the upper semiconductor DBR.

Such a differentiation is made to take in the light that obliquely enters the photo-sensing element in an efficient manner compared with the mesa structure where the side is vertical. The type of gas for dry etching is selected to control the selection ratio of, for example, GaInAsP of the active layer to, for example, AlGaAs of the upper semiconductor DBR. Accordingly, the tilt angle θ1 and the tilt angle θ2 can be controlled to have desired sizes.

In the present embodiment, θ1 and θ2 have, for example, angles of about 45 degrees. Note also that θ1<θ2.

Due to this configuration, a larger amount of light from above with a deep angle can be taken in. In other words, more light that is reflected from a lens or prism can be taken in, and more light that is scattered from a live subject can be taken in.

Figure 62:
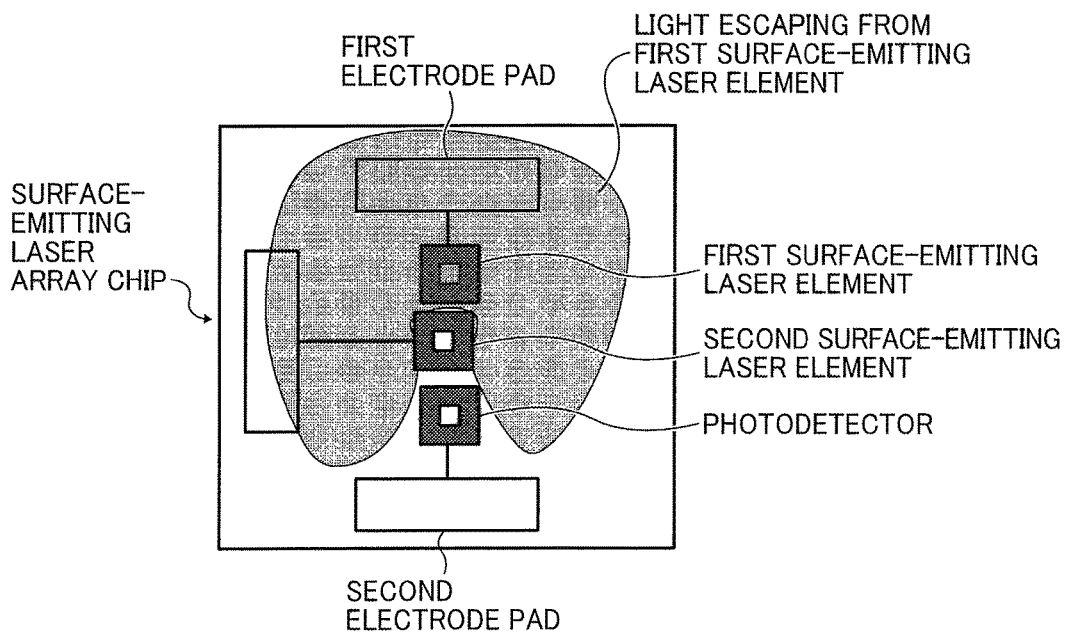
FIG. 62 is a diagram illustrating how escaping light propagates in a surface-emitting laser array chip, according to a fifth related art device.

FIG. 62 is a diagram illustrating how escaping light behaves in a surface-emitting laser array chip that includes a photodetector with mesa structure, according to a fifth related art device.

In the fifth related art device of FIG. 62, the bottom of the mesa structure is placed within the lower semiconducting DBR, in a similar manner to the first related art device illustrated in FIG. 48 or the third related art device illustrated in FIG. 50. In this configuration, the light escaping from the surface-emitting laser element (the first surface-emitting laser element) firstly propagates through the air. If there is another surface-emitting laser element (i.e., the second surface-emitting laser element) with mesa structure of same height in the propagation path of the escaping light as illustrated in FIG. 62, the escaping light is blocked and cannot reach the photodetector.

By contrast, in the first variation, the light that escapes from the surface-emitting laser element propagates through the lower spacer layer or the transparent insulator film. Due to this structure, even if there is another surface-emitting laser element with mesa structure between the mesa structure of the surface-emitting laser element and the mesa structure of the photo-sensing element, the escaping light is not blocked.

In view of the above circumstances, it is not always necessary to dispose the mesa structure of the surface-emitting laser element and the mesa structure of the photo-sensing element in close proximity. Even if a plurality of surface-emitting laser elements are provided for the multi-layer chip, the quantity of light that escapes from the surface-emitting laser element can be detected by the photo-sensing element regardless of how the elements are arranged. In short, the first variation of the first embodiment offers a high degree of flexibility in element arrangement.

In the fourth related art device illustrated in FIG. 54 (see JP-5442940-B1), the bottom of the mesa structure is placed within the lower spacer layer 103. On the top surface of the lower spacer layer 103, the oxidized layer 109 that serves as an insulator film is formed. In the example illustrated in FIG. 54, the use of an element adjacent to the surface-emitting laser element as a photo-sensing element is not at all taken into consideration. By contrast, in the example illustrated in FIG. 54, elements are designed to reduce the escaping light that reaches an adjacent surface emitting laser as much as possible. For this reason, the oxidized layer 109 is made as thin as possible. In view of the illustration of FIG. 54, the thickness of the oxidized layer 109 appears to be one fifth of the thickness of the element attaching portion of the lower spacer layer. If the thickness of the element attaching portion of the lower spacer layer is equivalent to the oscillation wavelength (for example, 780 nanometer (nm)), the thickness of the oxidized layer 109 is considered to be about 156 nm.

By contrast, in one concrete example of the first variation of the first embodiment, the optical thickness of the transparent insulator film is made as thick as one-half the oscillation wavelength λ such that the escaping light can propagate. For example, the thickness of the oscillation wavelength λ is 780 nm, and the thickness of the transparent insulator film is 390 nm in such a concrete example. Further, the optical thickness of the element attaching portion of the lower spacer layer is about λ/2, and the thickness of a region through which the escaping light propagates is approximately equivalent to the oscillation wavelength λ in total.

Moreover, the surface of the transparent insulator film is flattened as much as possible. A film formation method such as chemical-vapor deposition (CVD) is selected to perform flattening, and optimal processing conditions for flattening are selected. The level of flatness that is equivalent to the level of wavelength is satisfactory. Due to the selection of film formation method as described above, flatness is achieved to a level of one-tenths of the oscillation wavelength λ. Unless the processing is performed intentionally as above, for example, a foreign substance, roughness due to processing such as etching, or the like appears on the surface.

Figure 63:
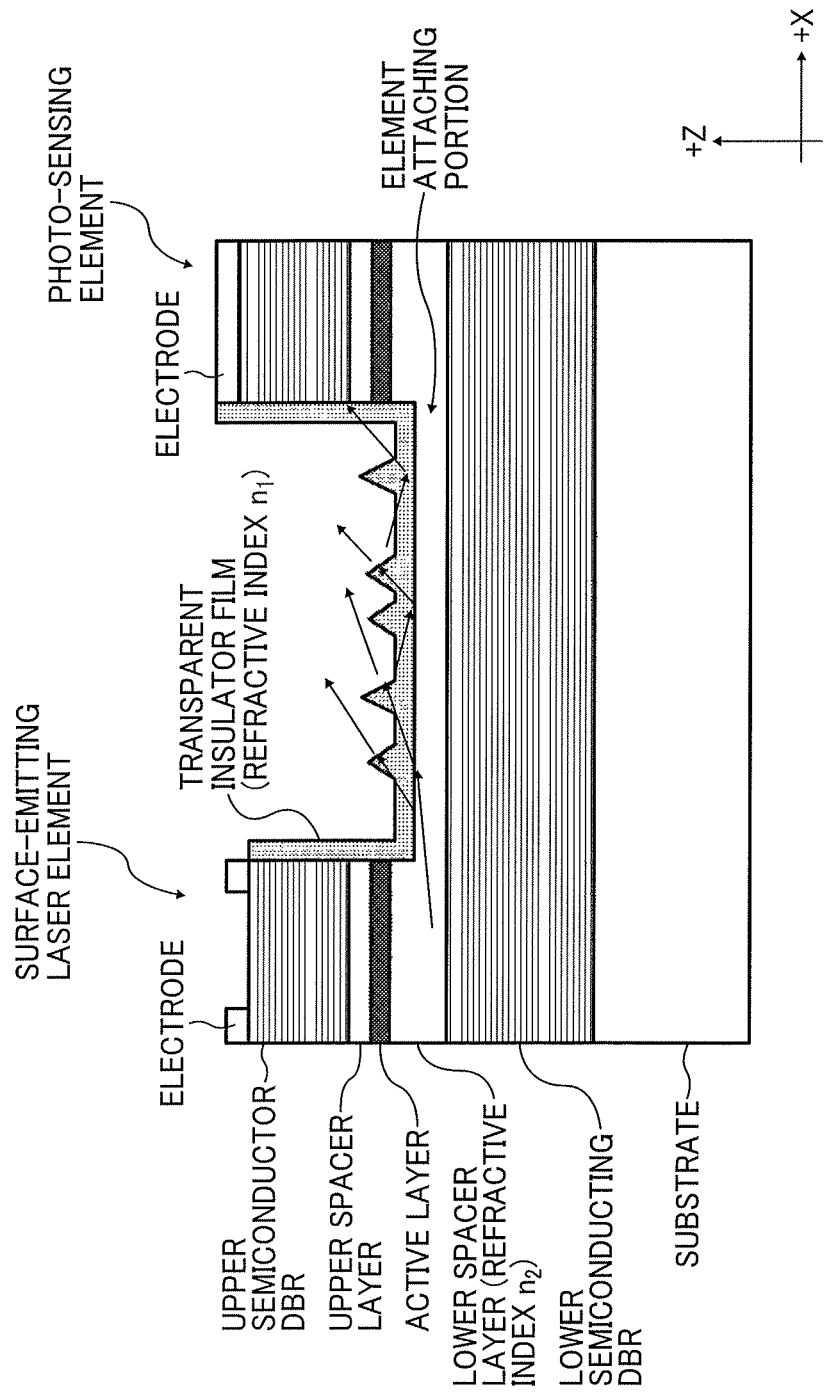
FIG. 63 is a diagram illustrating how the escaping light propagates and disperses when the surface of a transparent insulator film is rough.

FIG. 63 is a diagram illustrating how the escaping light propagates and disperses when the surface of a transparent insulator film is rough.

When the surface of the transparent insulator film is rough, as illustrated in FIG. 63, the light escapes from the surface, and the quantity of light to be detected by the photo-sensing element decreases.

The light source module LM can maintain the amount of light emitted from the light-emitting units at a constant light quantity as the controller 1001 controls the current value to be supplied to the channels to have an appropriate value. The light source module LM is attached to each of the transparent windows B such that a window member contacts the test object (transparent window B) from the +Z side.

Figure 5:
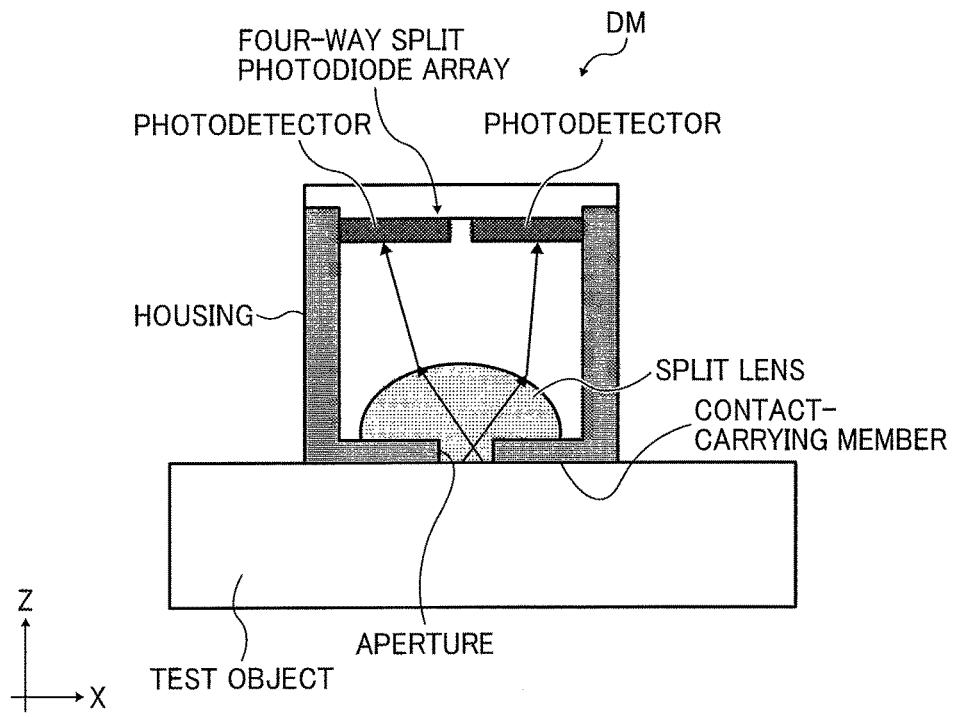
FIG. 5 is a diagram illustrating a general configuration of a detection module according to the first variation of the first embodiment.

FIG. 5 is a diagram illustrating a general configuration of a detection module according to the first variation of the first embodiment.

As illustrated in FIG. 5, the detection module DM includes a black-resin housing, a contact-carrying member consisting of an elastic body attached to a front end of the housing (i.e., the end on the −Z side), a 3.0 millimeters (mm) hemispheric lens (split lens) in diameter, and a four-way split photodiode array (an array of four photodiodes). The housing has apertures at the front end of the housing and at the other end of the housing in contact with the contact-carrying member. The detection module DM is attached to each of the transparent windows A such that the contact-carrying member contacts the test object (transparent window A) from the +Z side. Note that in FIG. 5, only two of the four photodiodes (photoreceptors) are illustrated.

The split lens is arranged in the proximity of the aperture on the +Z side. Due to this configuration, the light that is emitted from the light source module LM to the test object and then propagates inside the test object enters the split lens through the aperture, and is refracted and exited according to the position at which the light enters the split lens and the direction in which the light enters (see FIG. 5).

The four-way split photodiode array is arranged on the +Z-side of the split lens. Then, the light that has passed through the split lens enters one of the four photoreceptors (photodiodes) of the four-way split photodiode array according to the direction of travel (i.e., the exit direction from the split lens). As described above, the detection module DM can classify the incident angles at which the light exiting from the test object enters the detection module DM into four ranges of angle.

The controller 1001 detects the amount of light received by the four photodiodes (photoreceptor) of the detection module DM attached to each of the transparent windows A (the amount of light received by sixteen photodiodes in total), and converts the detected amount of light into voltage using an operational amplifier. Then, the controller 1001 stores the obtained value of voltage in the memory. The data is obtained at the sampling rate of 1 millisecond (msec), and the values obtained in the measurement in 20 seconds (sec) are averaged. In one-time measurement, the data of the sixteen photodiodes is obtained.

Next, the light source module LM is described in detail. As the light source of the light source module LM, a surface-emitting laser array including a plurality of surface-emitting laser elements, which are two-dimensionally disposed in the multilayer chip, is used.

Figure 6:
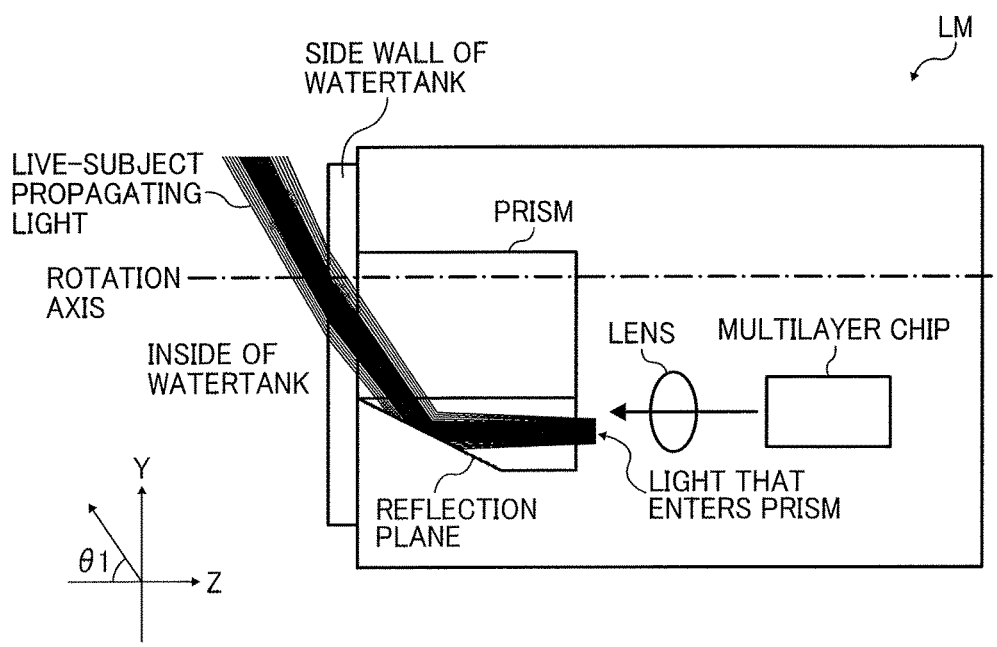
FIG. 6 is a second diagram illustrating a general configuration of the light source module according to the first variation of the first embodiment.
Figure 7A:
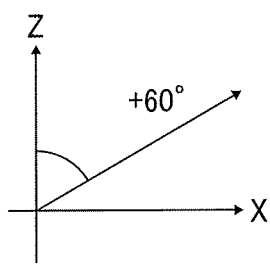
FIG. 7A to FIG. 7D illustrate the propagation angle inside the live subject according to the first embodiment of the present invention.
Figure 7B:
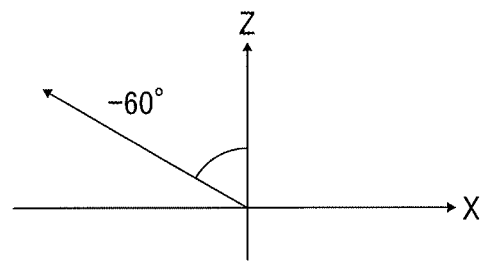
Figure 7C:
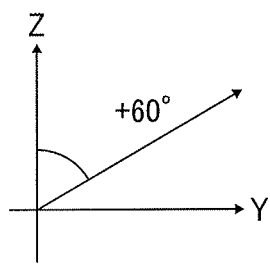
Figure 7D:
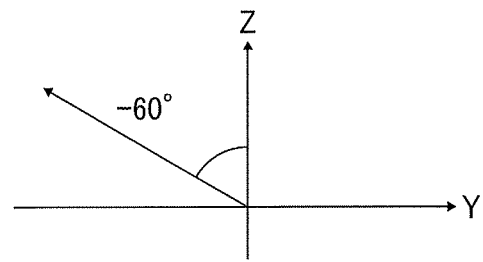

FIG. 6 is a second diagram illustrating a general configuration of the light source module according to the first variation of the first embodiment.

In the optical path of the multiple light rays emitted from the surface-emitting laser array, a 3 mm lens in diameter that approximately collimates the light rays is arranged (see FIG. 6). The distance between the exit plane (light-emitting surface) of the surface-emitting laser array and the principal point (optical center of the lens) is designed to be equal to the focal length f (for example, 9 mm) of the lens. In other words, the surface-emitting laser array is arranged such that the exit plane is disposed at the focal point of the lens. Note that "the focal length of the lens" indicates the distance between the principal point and the focal point of the lens.

In the present example, a plurality of surface-emitting laser elements are switched on at the same time, and the total output is about 50 milliwatts (mW). As illustrated in FIG. 6, the multiple parallel light rays emitted from the surface-emitting laser array are deflected by the prism.

As the prism, an acrylic prism whose refractive index is equivalent to that of the acrylic watertank as described above is adopted. The reflection plane of the prism is designed in accordance with the diameter of the prism, and the angle of the reflection plane is arranged such that the light that has passed through the lens enters the above-described acrylic watertank at the incident angle of about 50 degrees.

The difference in refractive index between the phantom (intralipid aqueous solution) and the acrylic plate of the watertank and the prism is designed such that the propagation angle in the phantom becomes about 60 degree ($\theta 1$ in FIG. 6) according to the Snell law (the law of reflection). The multilayer chip, the lens, and the prism together configure an integrated optical unit, and the integrated optical unit is attached to a rotatable stage disposed on the inner wall of the watertank. The rotatable stage rotates around the rotation axis that extends in the Z-axis direction.

As the rotatable stage and optical unit rotate together, the incident angle and direction of the light that enters the test object can be changed. For example, when a prism that is axisymmetric with reference to the rotation axis of the rotatable stage is used, only the multilayer chip and the lens may be unitized and rotated together with the rotatable stage with reference to the fixed prism.

FIG. 7A to FIG. 7D illustrate the propagation angle inside the live subject according to the first embodiment of the present invention.

In the present example, as illustrated in FIG. 7A to FIG. 7D, the measurement is sequentially performed in the four directions including the +X, −Y, +Y, and −Y directions. Accordingly, the measurement is performed for the four positions of the four light source modules LM (B1 to B4) and for the four directions. As a result, the measurement is performed sixteen times in total. In between the prism and the watertank, gel-like resin with the refractive index equivalent to that of the prism and the watertank is filled. Accordingly, the refraction or reflection between the prism and the watertank can be prevented.

Figure 8:
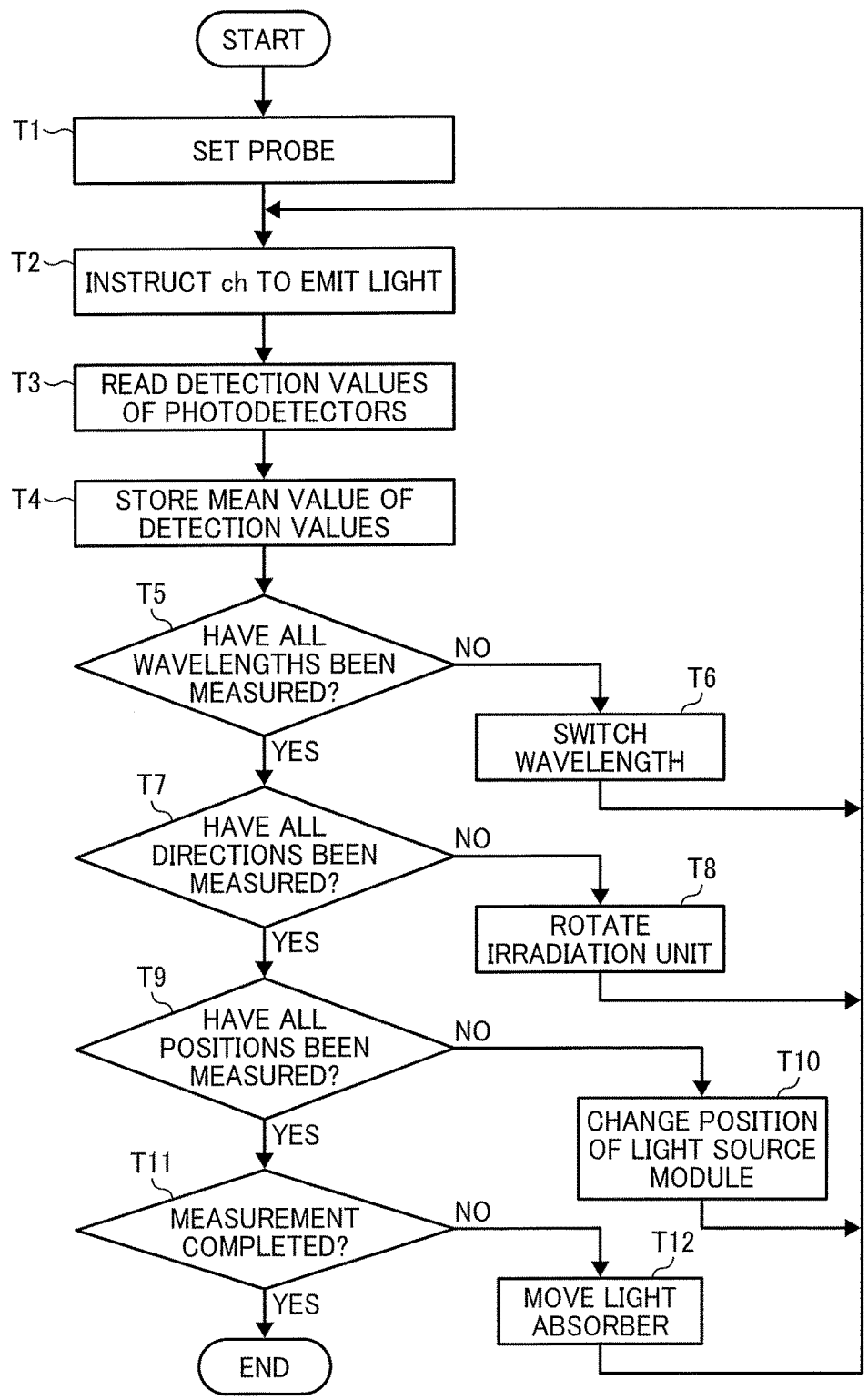
FIG. 8 is a flowchart of a method of measuring the internal information of the test object, according to the first embodiment of the present invention.
Figure 9:
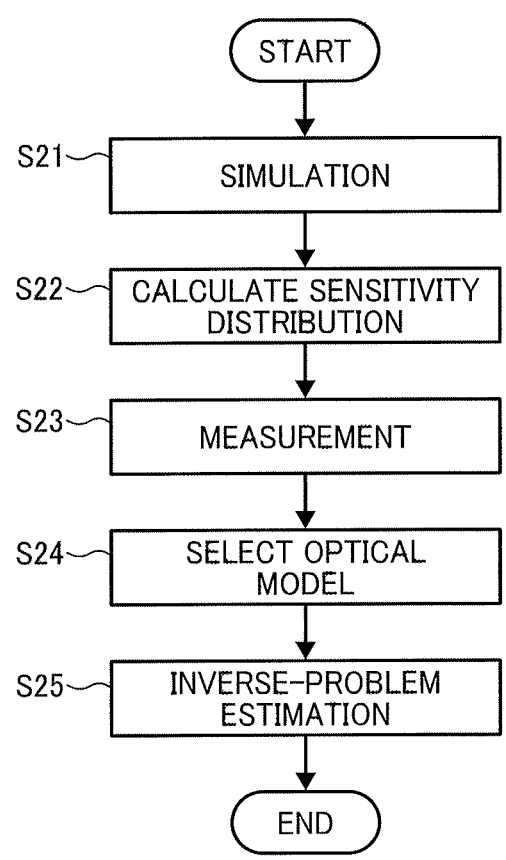
FIG. 9 is a flowchart of an inverse-problem estimation algorithm, according to the first embodiment of the present invention.

FIG. 8 is a flowchart of a method of measuring the internal information of the test object, according to the first embodiment of the present invention.

Firstly, a probe is set (step T1). As described above, the probe indicates the detection module DM and the light source module LM. Here, the probe to be set includes four detection modules DM and one light source module LM. The four detection modules DM are attached to each of the four 9 mm transparent windows A in diameter as illustrated in FIG. 3. The one light source module LM is attached to the transparent window B1 as illustrated in FIG. 3.

Next, the light source module LM is instructed to emit light (step T2). The light-emission intensity is determined such that the current value becomes about 1 mW.

The value of the light-emission intensity is measured by an external monitor. The current value of the light that is emitted from the photo-sensing element was measured, and was found to be about 6 microamperes (μA). Once the obtained current value is corrected using an external monitor, appropriate light quantity can continuously be achieved afterward by adjusting the current value to the corrected value again. By so doing, an accurate distribution of cerebral blood flow can be obtained.

The light emitting period is about 20 seconds (sec), and the detection values of the four photodiodes of the detection module DM are read during the light emitting period (step T3). The data (detection values) obtained at 1 millisecond (msec) intervals are averaged. Then, the averaged detection values, i.e., the mean value of detection values, is stored in the memory (step T4).

Next, the wavelength of the exiting light is switched, and the steps T2 to T4 are performed again (steps T5 and T6). In the present embodiment, one of the wavelengths 780 nm and 900 nm may be selected. More specifically, two types of light source modules LM with different oscillation wavelengths (780 nm band and 900 nm band) are prepared in advance, and the light source modules LM are replaced. By so doing, the wavelengths of the exiting light can be switched.

In the present example, the measurement is performed for the four directions including the +X direction, +Y direction, −X direction, and −Y direction (steps T7 and T8). More specifically, the steps T2 to T6 immediately after the step T1 are performed upon arranging the prism in the +X direction. Next, the prism is rotated to the +Y direction. In this state, the steps T2 to T6 are repeated. Next, the prism is rotated to the −X direction. In this state, the steps T2 to T6 are repeated. Next, the prism is rotated to the −Y direction. In this state, the steps T2 to T6 are repeated.

Next, the position where the light source module LM is attached is sequentially changed from the transparent window B1 to the transparent windows B2, B3, and B4, and the measurement is performed again for the four directions (steps T9 and T10). Then, the position of the light absorber is shifted, and the measurement is performed again for the four directions and the four positions where the light source module LM is attached (steps T11 and T12).

The stored data is labeled as r(s,i,n) (i=1, 2, 3, ... M; n=1, 2, 3, ... K) with the light absorber and r(0,i,n) (i=1, 2, 3, ..., M; n=1, 2, 3, ..., K) without the light absorber. "i" denotes the numbers assigned to the respective detection modules DM.

"n" denotes the numbers assigned to the respective groups. Next, the difference Δr(i,n) of the respective groups is calculated.

Next, a method of calculating the position of the light absorber (the optical properties of the pseudo live subject) according to the result of the measurement obtained by the measurement method as depicted in the flowchart of FIG. 8 is described. In this method, an inverse-problem estimation algorithm is adopted. In order to solve an inverse problem, firstly, measurement and simulation are performed and a sensitivity distribution is calculated using a forward problem. Then, the data obtained by the subsequent measurement is imported, and an inverse problem estimation is performed based on the value in the imported data (see steps S21 to S25 in FIG. 9).

Figure 43:
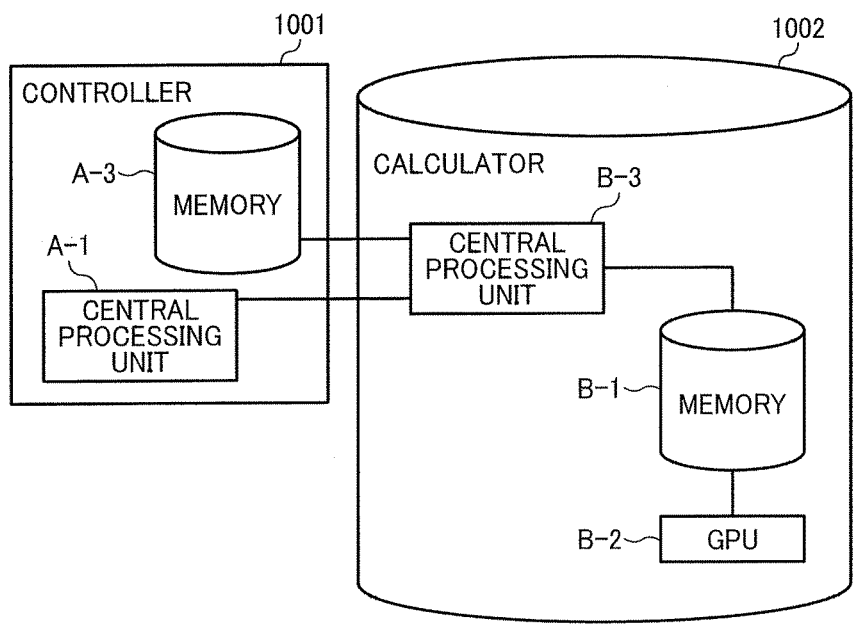
FIG. 43 is a block diagram illustrating a configuration of a calculator according to the embodiments of the present invention.

FIG. 43 is a block diagram of the calculator 1002 according to the present embodiment.

Data such as that of the position of the modules (probes) and the refractive index or shape of the live subject, which is used for the Monte Carlo simulation as will be described later, is stored in the memory B-1. The above-mentioned forward problem is performed based on the stored data as above. In the calculation of this forward problem, a graphics processing unit (GPU) (multigraphics processor) capable of parallel computation is used. The use of such a GPU dramatically speeds up the calculation compared with the conventional configuration. The sensitivity distribution obtained by this calculation is stored again in the memory B-1. This calculation result and the measurement result stored in the memory A-3 are input to the central processing unit B-3, and the central processing unit B-3 performs the inverse problem estimation. The estimation result is displayed on the display unit 1003 through the central processing unit A-1 (see FIG. 42).

Conventionally, in the forward problem calculation, it was believed that the light in a scatterer such as a live subject disperses in an almost isotropic manner. For this reason, a simulation using a diffusion equation with less computational complexity has been adopted. In recent years, however, it has been reported, for example, in academic conferences, that the light propagation in a minute area of a few millimeters is in fact anisotropic in a live subject. In order to perform a simulation in view of such anisotropy, a transport equation or the Monte Carlo simulation is performed.

In the present embodiment, the light emitted from the light source is deflected so as to enter the test object. For this reason, a diffusion equation known in the art is not sufficient to perform a simulation in view of the data of the incident angle. A method in which a transport equation is used has been suggested. However, it is known in the art that a method in which a transport equation is used takes an enormous length of time to complete.

In order to handle such a situation, the Monte Carlo simulation is adopted in the present embodiment. The Monte Carlo simulation is a method in which the condition for the photons to disperse in a scattering medium are stochastically expressed by a random variable and the macroscopic behavior of the photons is observed. More specifically, the behavior of the photons is modeled with the assumption that the photons move in a medium and collision occurs every time the photons travel a certain distance and that the directivity of the photons changes accordingly. The average distance traveled by the photon in the above model is the mean free path, and the mean free path is defined by a scattering coefficient. The changes in direction are defined by the anisotropy g. The repeated collisions and how the photon propagates in a specified area are recorded. By calculating a myriad of photons in the model as described above, the behavior of the light in the scattering medium can be simulated. By the Monte Carlo simulation, the path of the dispersion of one photon is recorded.

In the Monte Carlo simulation according to the present embodiment, a 120 mm×120 mm×60 mm three-dimensional area is calculated where the number of photons is $10^9$ and the voxel is a 1 mm cube. In the present embodiment, the scattering coefficient, absorption coefficient, anisotropy, and the refractive index of the scattering medium are 7.8 $mm^{-1}$, 0.019 $mm^-$, 0.89, and 1.37, respectively, and these values are almost equivalent to the scattering coefficient, absorption coefficient, anisotropy, and the refractive index of a scalp. The above-described phantom (intralipid aqueous solution) is prepared to satisfy these values, and a simulation is performed under the same situations as those of the phantom with all aspects such as the propagation angle and the positions of the light source module LM and the detection module DM to calculate a sensitivity distribution.

In this simulation and calculation, it is assumed that the number of photons that have passed through the position r of the voxel is $\phi_0(r)$. In particular, it is assumed that the number of photons that have passed through the position r of the voxel where the position of the light source module LM is "rs" is $\phi_0(rs,r)$. Next, the light source module LM is disposed where the detection module DM was disposed and the same number of photons is calculated again. When the detection module DM is disposed at "rd", it is assumed that the number of photons that have passed through the position of the voxel is $\theta_0(r,rd)$.

As the optical path is reversible, this product is proportional to the number of photons that pave passed through the position r of the voxel, emitted from the light source module LM, and have entered the detection module DM. The product is normalized by the number $\phi_0(rs,rd)$ of all the photons that enter the detection module DM. As a result, the following sensitivity distribution A(r) is obtained.

$$A(r) = \frac{\phi_0(rs, r)\phi_0(r, rd)}{\phi_0(rs, rd)} \quad \text{[Formula 1]}$$

The sensitivity distribution A(r) indicates the degree of influence on the amount of detection at the position r. The sensitivity distribution A(r) indicates how much the detection value changes due to the presence of a light absorber at the position r of the voxel.

Figure 10:
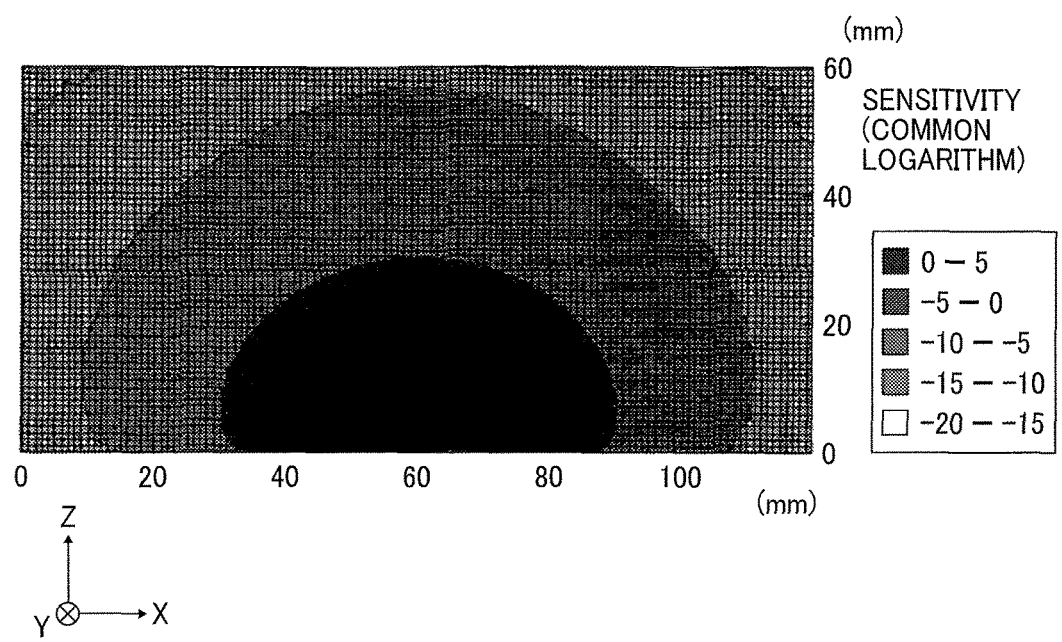
FIG. 10 is a first diagram illustrating the sensitivity distribution at a photodiode, according to the first embodiment of the present invention.

FIG. 10 is a first diagram illustrating an example of the sensitivity distribution calculated as above at a photodiode, according to the first embodiment of the present invention.

In FIG. 10, the light source module LM and the detection module DM are disposed at (X,Y,Z)=(45,60,0) and (X,Y,Z)=(75,60,0), respectively. As the voxel is a 1 mm cube, the measurement unit is equivalent to that of these values. The sensitivity of the voxel at each position is indicated by the base 10 logarithm (common logarithm) base.

Figure 11:
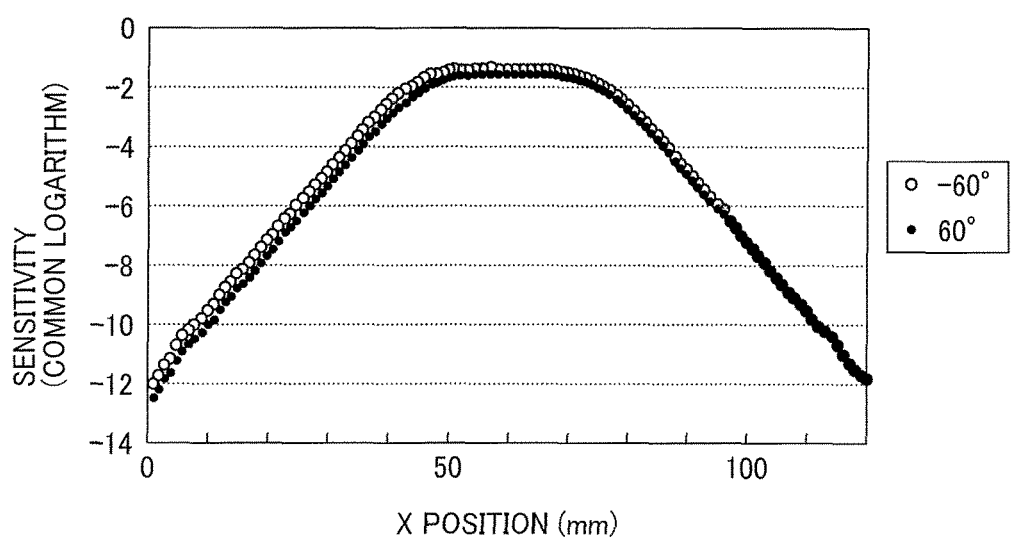
FIG. 11 a second diagram illustrating the sensitivity distribution at a photodiode, according to the first embodiment of the present invention.

FIG. 11 a second diagram illustrating the sensitivity distribution at a photodiode, according to the first embodiment of the present invention.

Next, the line with Y=60 and Z=10 of the voxel (x,y,z) is extracted from the sensitivity distribution illustrated in FIG. 10. Then, the extracted line is plotted where the vertical axis and the horizontal axis indicate the sensitivity and the x position, respectively. The results are depicted in FIG. 11.

Figure 12A:
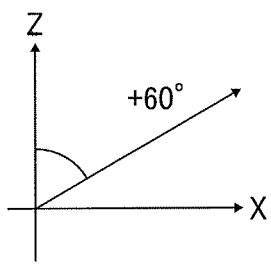
FIG. 12A and FIG. 12B illustrate the propagation angle inside the live subject according to the first embodiment of the present invention.
Figure 12B:
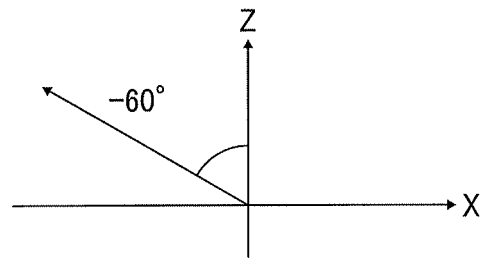

FIG. 12A and FIG. 12B illustrate the propagation angle inside the live subject according to the first embodiment of the present invention.

More specifically, FIG. 12A and FIG. 12B illustrate the propagation angles inside the live subject when the angle which the light forms with the X-axis on the plane where the Y-axis is the normal line is +60 degrees and −60 degrees, respectively.

As illustrated in FIG. 11, there are differences in the sensitivity distribution between the case of +60 degrees and the case of −60 degrees. Such differences serve as a guiding principle to determine whether the improvement in resolution becomes possible. In other words, the presence of a difference between these two sensitivity distributions indicate that the propagation paths of the light rays emitted from two light sources are different from each other. If the propagation paths are the same, the sensitivity distributions should be about the same as well even if the propagation angle varies. As the propagation paths from the two light sources are different from each other, the light rays from the two light sources collect different information.

This fact is significant for the inverse problem estimation as will be described later. As described above, the propagation of light is not simple isotropic scattering, but is slightly anisotropic of the order of several millimeters. It is considered that such a difference on the order of several millimeters becomes a factor in achieving inverse problem estimation with the resolution on the order of several millimeters. Such a sensitivity distribution is to be calculated for all the propagation angles and detection angles of all the light source modules LM and detection modules DM in the phantom.

Next, the sensitivity distribution is used to perform inverse problem estimation. Assuming that the change $\delta\mu_a(r)$ in absorption coefficient caused by a light absorber is sufficiently small, the following equation holds true due to the approximation of Retov.

$$\log\frac{\phi_0(rs, rd)}{\phi(rs, rd)} = \frac{v}{S}\frac{\int d\vec{r}\phi_0(rs, r)\delta\mu_a(r)\phi_0(r, rd)}{\phi_0(rs, rd)} \qquad \text{[Formula 2]}$$

v denotes the velocity of light in a medium, and S denotes the amount of light emitted from the light source module LM per unit time, rs denotes the position of the light source module LM, and rd denotes the position of the detection module DM. $\phi(rs,rd)$ indicates the amounts of the light that is received by the detection module DM after being emitted from the light source module LM, and $\phi_0$ indicates the light intensity on condition that a light absorber is absent. This formula indicates that when the light intensity $\phi_0$ is given in the absence of the light absorber, a linear correlation is established between the observed value log $\phi(rs,rd)$ and the change $\delta\mu_a(r)$ in the absorption coefficient caused by the light absorber.

This may be simplified in the equation as follows.

$$Y=A(r)X$$

In this equation, Y denotes the change in the observed value due to the presence or absence of the light absorber, and X denotes the change in the absorption coefficient at the position r of the voxel. Moreover, A(r) indicates the sensitivity distribution. The above equation indicates how the observed value Y changes due to the change in the position or amount of light absorber indicated by X.

In an inverse problem estimation, calculation the other way around is performed. In other words, the position X of the light absorber is estimated using the observed value Y. As described above with respect to the position measuring method, measurement is performed upon assuming that the change due to the presence or absence of the light absorber is the difference $\Delta r(i,n)$. This difference $\Delta r(i,n)$ is used as the observed value Y to calculate X.

As known in the art, an estimation method for a reverse problem called L2 norm regularization is used for the above calculation. In this method, X that minimizes the cost function C as given below is calculated.

$$C=|Y-AX|^2+\lambda|X^2| \qquad \text{[Formula 3]}$$

In the Formula 3, Y, A, and $\lambda$ indicate the observed value, the sensitivity distribution, and the regularized coefficient, respectively. In the inverse problem estimation, the above method is commonly adopted. However, in the present embodiment, the Bayes estimation that can also detect the depth direction is used to perform an inverse problem estimation. For the detail of the inverse problem estimation using a Bayes estimation, see "T. SHIMOKAWA, T. KOSAKA, O. YAMASHITA, N. HIROE, T. AMITA, Y. INOUE, AND M. SATO, "Hierarchical Bayesian estimation improves depth accuracy and spatial resolution of diffuse optical tomography," Opt. Express*20*, 20427-20446 (2012)". Moreover, the results given below are disclosed in JP-2015-092151-A.

Figure 13A:
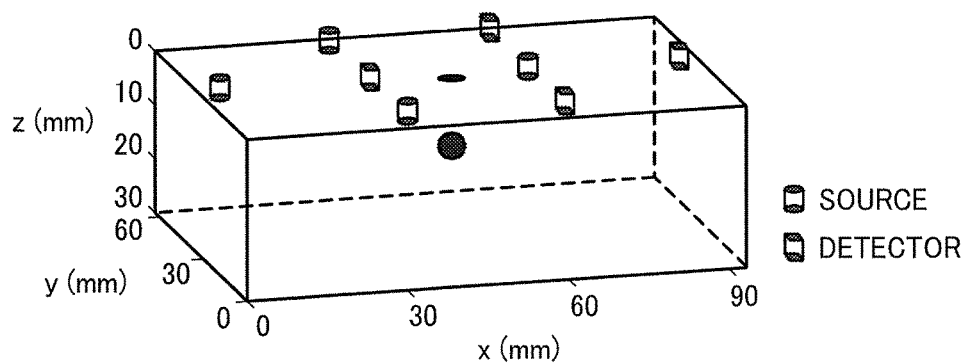
FIG. 13A illustrates the actual position of the light absorber, according to the first embodiment of the present invention.
Figure 13B:
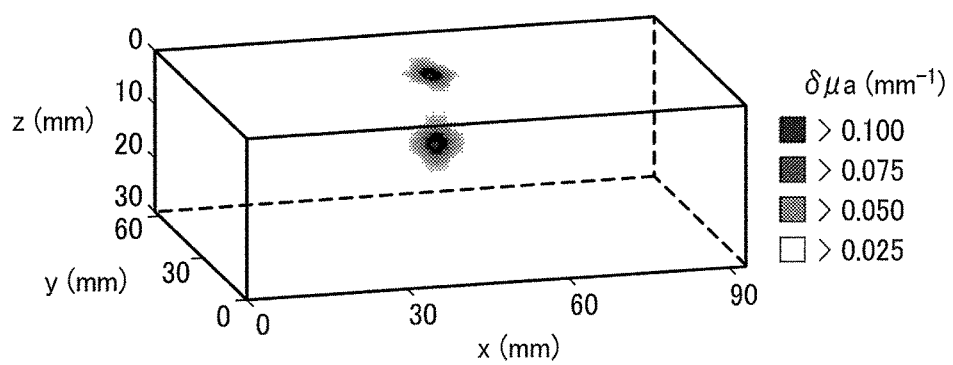
FIG. 13B illustrates a result of estimation of the position of the light absorber, according to the first embodiment of the present invention.

As a result, the result of estimation as illustrated in FIG. 13B can be obtained.

FIG. 13A illustrates the actual position of the light absorber, according to the present embodiment.

FIG. 13B illustrates a result of estimation of the position of the light absorber, according to the present embodiment.

The grid in FIG. 13B has 3 mm patterns, and the actual position can be obtained with 3 mm precision.

Figure 13C:
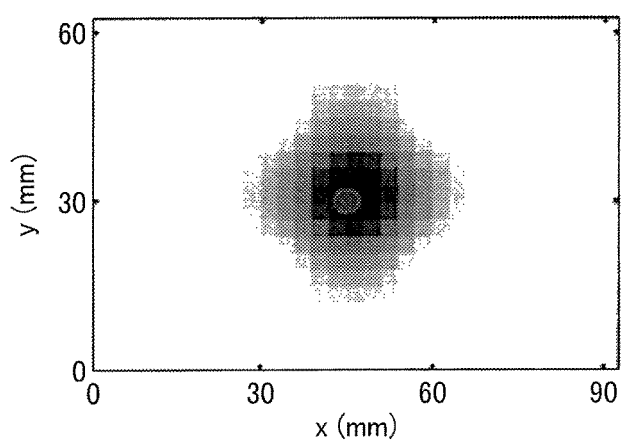
FIG. 13C illustrates a result of the detection of the position of the light absorber, according to a control sample.

FIG. 13C illustrates a result of the detection of the position of the light absorber, according to a control sample.

The result of detection where one of the four orientations is used is illustrated in FIG. 13C as a control sample. The configuration of this control sample is almost equivalent to that of the conventional NIRS DOT device. In the control sample, it is not possible to detect the depth direction, and the detection result becomes very much dispersed. By contrast, in the first variation of the present embodiment, the Bayes estimation is adopted as described above, and both the position and depth of the light absorber are detectable.

Figure 14A:
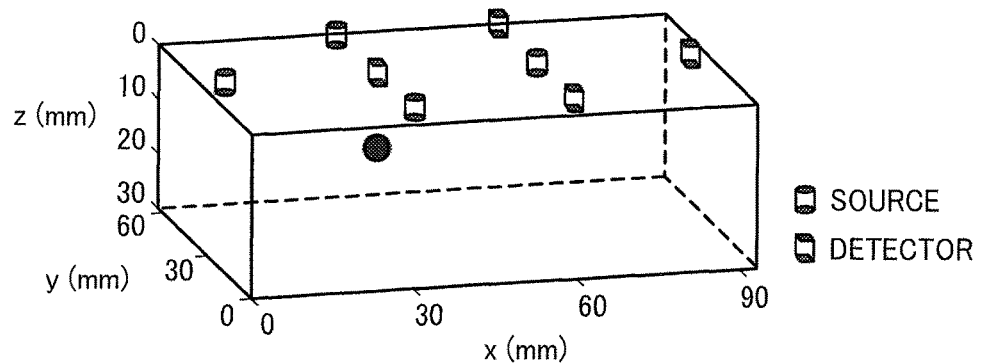
FIG. 14A illustrates the actual position of a light absorber after movement, according to the first embodiment of the present invention.

FIG. 14A illustrates the actual position of a light absorber after movement, according to the first embodiment of the present invention.

Figure 14B:
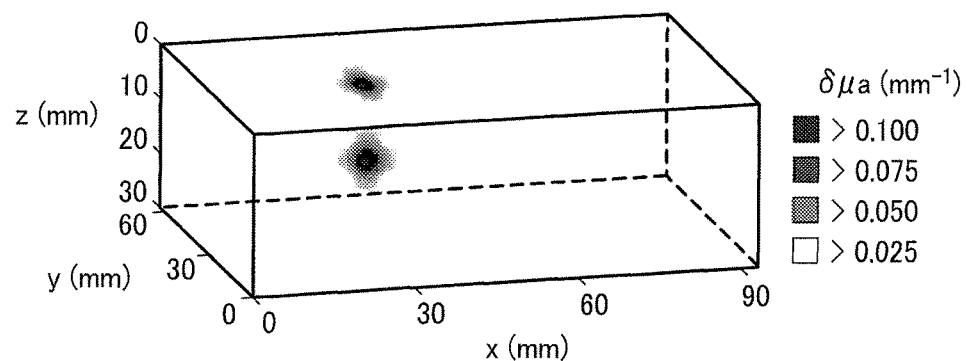
FIG. 14B illustrates a result of estimation of the position of a light absorber after movement, according to the first embodiment of the present invention.

FIG. 14B illustrates a result of estimation of the position of a light absorber after movement, according to the first embodiment of the present invention.

Figure 14C:
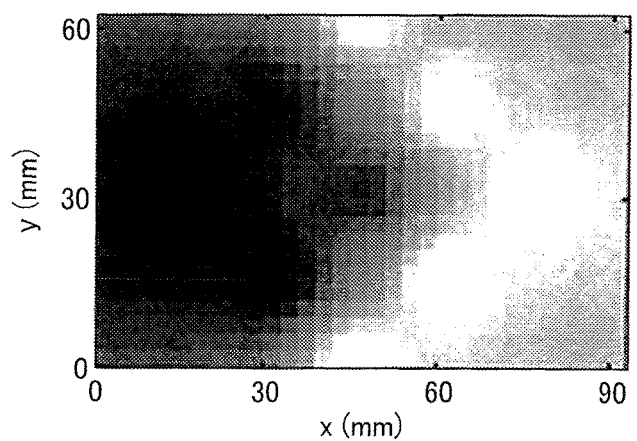
FIG. 14C illustrates a result of detection of the position of a light absorber, according to a control sample.

FIG. 14C illustrates a result of detection of the position of a light absorber, according to a control sample.

The position of the light absorber is changed as illustrated in FIG. 14A, and the estimation of the position is performed as illustrated in FIG. 14B. Even after the light absorber is moved, the actual position of the light absorber is precisely estimated. As the method in the first example is adopted, the position of the light absorber is detectable with high resolution. By contrast, in the control sample, the image of the light absorber is very much dispersed as illustrated in FIG. 14C, and it is not possible to detect the position of the light absorber with accuracy.

Next, a second variation of the present embodiment is described below. Note that the second variation will be described in relation to the first example where appropriate.

[Second Variation]

Firstly, black ink is dripped into the intralipid aqueous solution, which fills the acrylic transparent watertank, to the degree of about 200 ppm, where the intralipid aqueous solution is obtained by diluting 10 percent intralipid ten times. Accordingly, an absorption coefficient and scattering coefficient that are almost equivalent to those of a live subject can be achieved. Then, a black light absorber simulating bloodstream is sunk into the whitish intralipid aqueous solution. In the present example, the light absorber is, for example, black polyacetal, and has an approximately 5 mm spherical body in diameter. In order to control the position of such a spherical body, the spherical body is attached to a thin 1 mm metallic rod in diameter, and the rod is connected to an automatic positioning stage. A probe is precisely aligned to a side of the watertank, and is attached thereto. In the present example, the acrylic watertank has a rectangular-parallelepiped shape with the volume of, for example, 140 mm×140 mm×60 mm, where thickness of the wall is 1 mm.

The optical sensor 10 includes an irradiation system including a plurality of (for example, eight) light source modules LM, and a detection system including a plurality of (for example, eight) detection modules DM. Each of the light source modules LM and the detection modules DM is connected to the controller 1001 through the electrical wiring.

The controller 1001 controls the timing of light emission at the light sources of the light source modules LM or the timing of detection at the detection modules DM, and transfers the obtained detection results to the memory. Moreover, the controller 1001 reads the data stored in the memory and perform calculation using the values of the read data, and controls the display unit 1003 to display the calculation result thereon.

Figure 15:
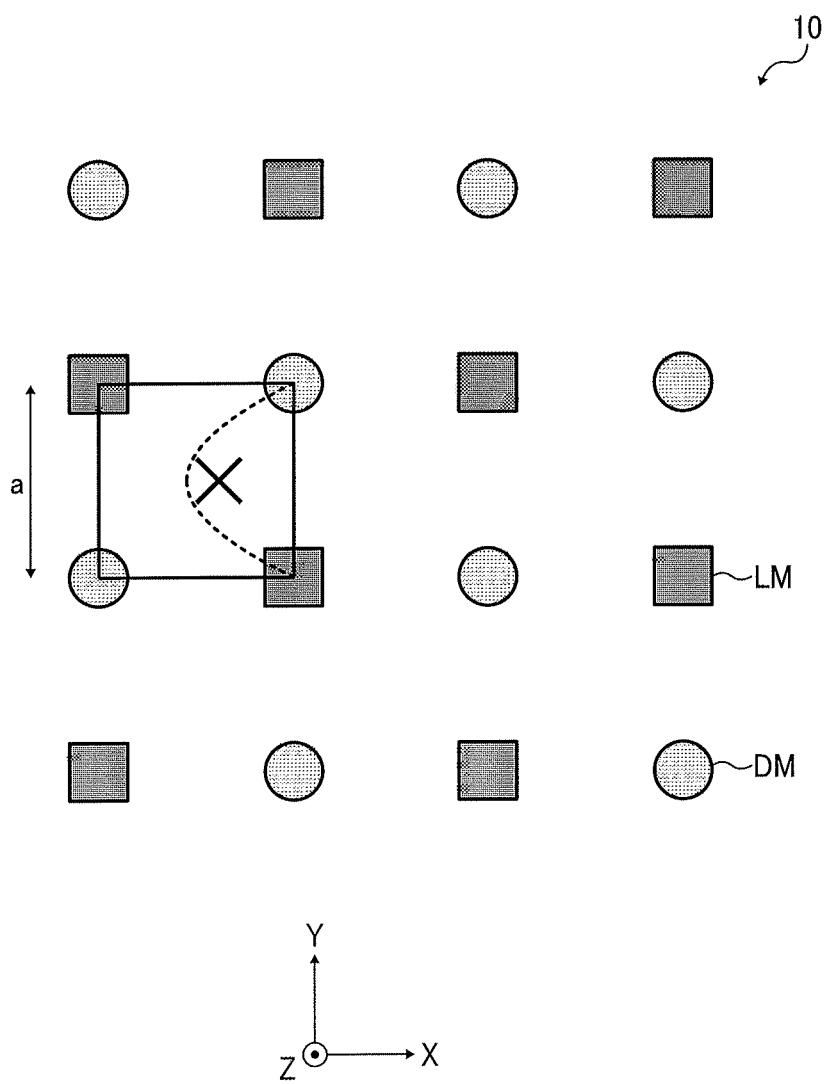
FIG. 15 is a diagram illustrating the arrangement of a plurality of light source modules and a plurality of detection modules in an optical sensor, according to a second variation of the first embodiment.

FIG. 15 is a diagram illustrating the arrangement of a plurality of light source modules and a plurality of detection modules in an optical sensor, according to a second variation of the first embodiment.

As illustrated in FIG. 15 for example, the eight light source modules LM and the eight detection modules DM are arranged for a pseudo live subject in a four-by-four matrix (two-dimensional grid pattern) in the X direction and the Y direction with equal pitches, such that the light source module M and the detection module DM are next to each other in both the X direction and the Y direction that are orthogonal to each other. In FIG. 15, the rectangular signs denote the light source modules LM, and the circular signs denote the detection modules DM.

Figure 16:
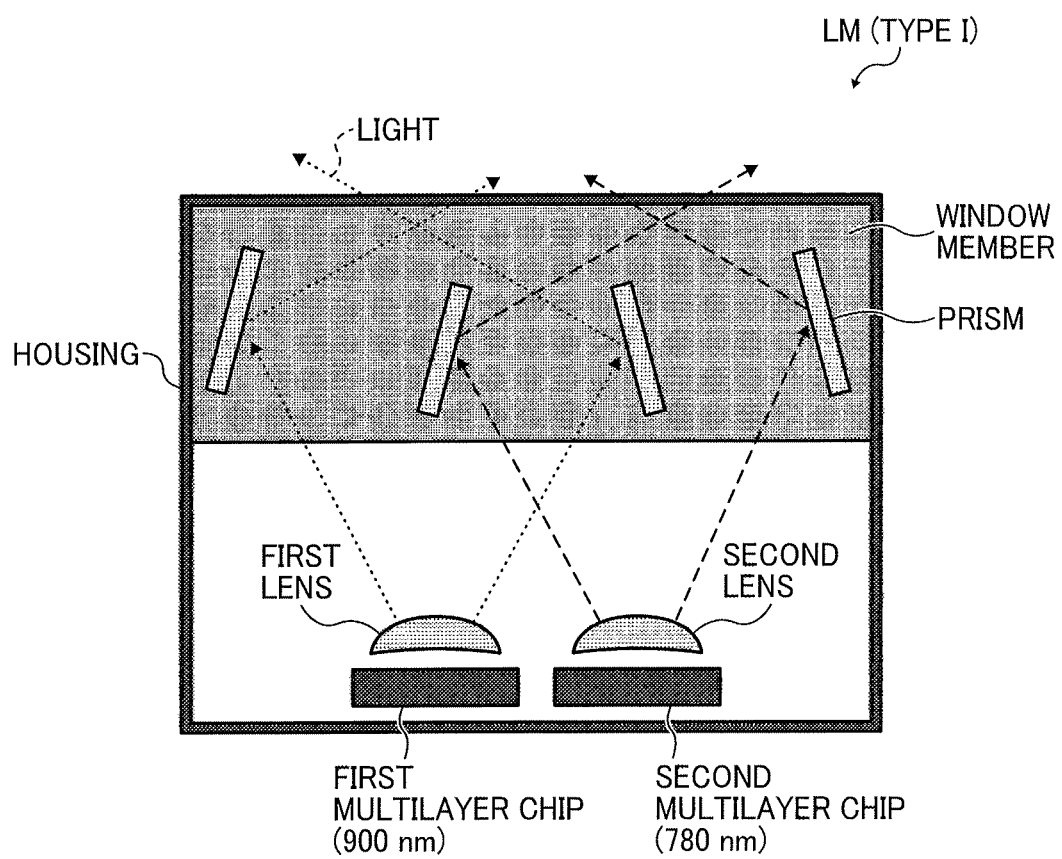
FIG. 16 is a diagram illustrating a light source module LM (type I) according to the second variation of the first embodiment.

FIG. 16 is a diagram illustrating a light source module LM (type I) according to the second variation of the first embodiment.

As illustrated in FIG. 16, the light source module LM (type I) according to the second variation includes, for example, a ceramic package for which a lens, an optical element such as a prism, and a plurality of (for example, two) multilayer chips (i.e., first and second multilayer chips in FIG. 16) similar to the multilayer chip according to the first example as above are provided, a flexible circuit board on which the ceramic package and an analog electronic circuit are mounted, a wiring connected to the flexible circuit board, a connector, a housing accommodating these elements, a window member consisting of transparent resin that contacts the test object.

The light rays that are emitted from the surface-emitting laser elements of the multilayer chips are refracted by the corresponding lenses, and deflected to a desired angle (reflected to a prescribed direction) by the prisms that are formed inside the window member and exited to the outside of the housing. In the present example, the prism serves as a reflection member.

Figure 17:
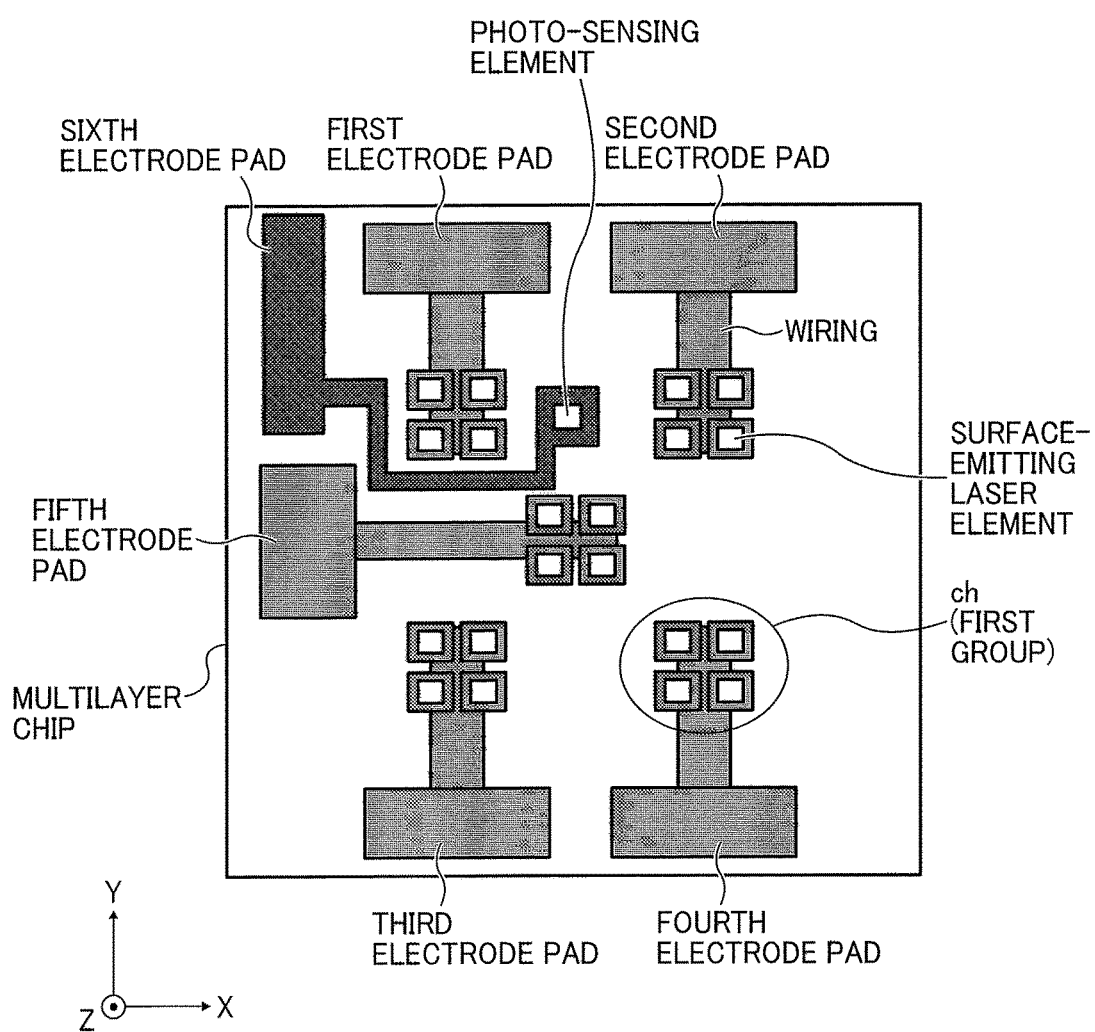
FIG. 17 is a diagram illustrating a surface-emitting laser array chip of the light source module LM (type I), according to the second variation of the first embodiment.

FIG. 17 is a diagram illustrating a surface-emitting laser array chip of the light source module LM (type I), according to the second variation of the first embodiment.

As illustrated in FIG. 17, the multilayer chip has a square shape with the sides of about 1 mm, and includes a plurality of (for example, twenty) two-dimensionally arranged surface-emitting laser elements and one photo-sensing element.

More specifically, each multilayer chip includes five groups of channels each of which includes four surface-emitting laser elements. Note that each group of channels may be referred to as "ch" in the following description. In the present example, the centers of the four groups among the five groups are disposed separately at the four vertices of the square, and the center of the remaining one group is disposed at the center of the square. Moreover, a photo-sensing element is disposed near the group that is disposed at the center of the square.

The four surface-emitting laser elements of each group are connected to the same electrode pad (i.e., one of the first electrode pad to the fifth electrode pad) through the bonding wire (wiring). The photo-sensing element is connected to the sixth electrode pad through the bonding wire (wiring). The sixth electrode pad is connected to the ammeter.

The ceramic package is implemented by being soldered onto the wiring pattern of the flexible circuit board. On the flexible circuit board, a semiconductor for switching or a semiconductor for stabilizing the current are attached. The semiconductor for switching controls which channel of the multilayer chip is to emit light. The semiconductor for switching controls the selected channel to emit light according to the externally given serial signal. One end of the signal line for the serial signal and one end of the power supply line are connected to the flexible circuit board, and the other end of the signal line and the other end of the power supply line are connected to the controller 1001.

The amount of light emission of each channel is calibrated constant at regular intervals. Under normal conditions, the five groups are controlled to emit light in sequence with short pulses. As the temperature rise due to heat liberation can be avoided, such pulse light emission is suitable for stabilizing the amount of light emission. The detection values obtained every time light is emitted with short pulses by the detection module are added up and then averaged. By so doing, the detection becomes resistant to the noise.

In so doing, light emission is performed for each group, and the light-emission intensity is measured by an external monitor. The value of the current that is flowing from the sixth electrode pad to the ammeter, i.e., the current value of the light that is emitted from the photo-sensing element, was measured, and was found to be about 6 microamperes ($\mu A$). Such a current value varies for each group, and the data of the current values and the values of the light-emission intensity measured by the external monitor are stored as a table. Once the obtained current value is corrected using an external monitor, appropriate light quantity (desired light quantity) of each group can continuously be achieved afterward by adjusting the current value to the corrected value again. By so doing, an accurate distribution of light absorbers (for example, distribution of cerebral blood flow) can be obtained.

The oscillation wavelength of the surface-emitting laser elements of each multilayer chip is, for example, 780 nanometer (nm) or 900 nm. By using a plurality of surface-emitting laser elements with different oscillation wavelengths, a plurality of exiting lights with different wavelengths can be obtained. Further, a plurality of light rays with different wavelengths are emitted to an approximately identical point of a test object (for example, a live subject). By so doing, for example, the state of hemoglobin (i.e., a deoxidized state or an oxidized state) can be recognized. These wavelengths are selected in view of the fact that the absorption coefficient varies widely according to the oxygen concentration in the blood.

Figure 18A:
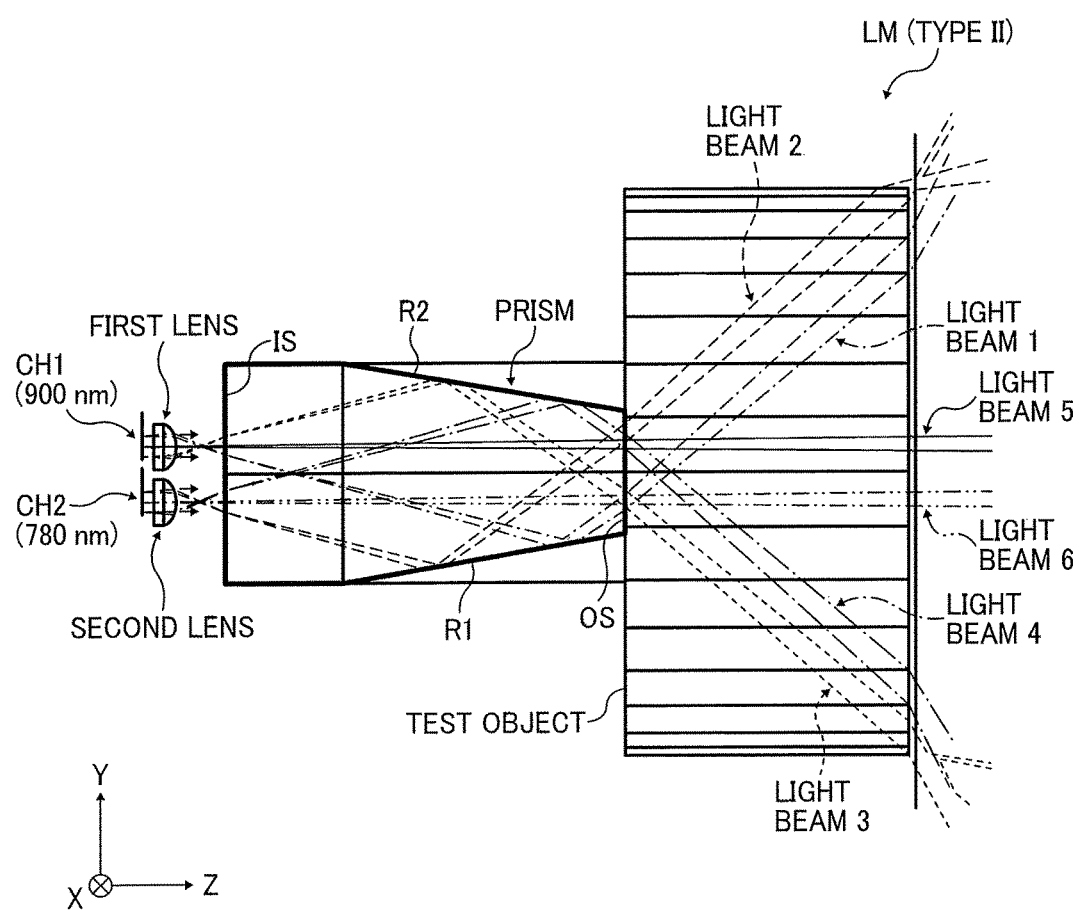
FIG. 18A and FIG. 18B are first and second diagrams each illustrating a light source module LM (type II) according to the second variation of the first embodiment.

FIG. 18A is a first diagram illustrating a light source module LM (type II) according to the second variation of the first embodiment.

In the light source module LM (type II) according to the second variation illustrated in FIG. 18A, a first surface-emitting laser array chip CH1 with the oscillation wavelength of 900 nm and a second surface-emitting laser array chip CH2 with the oscillation wavelength of 780 nm are arranged in parallel with each other. Moreover, a first lens (separate optical element) is disposed in the proximity of the exit end of the first surface-emitting laser array chip CH1, and a second lens (separate optical element) is disposed in the proximity of the exit end of the second surface-emitting laser array chip CH2. Further, a prism (common optical element) for common use is disposed in the optical paths of the two light rays with different wavelengths that have passed through the first and second lenses. The surface-emitting laser array chips CH1 and CH2 are aligned in the Y direction on the XY plane such that the exit directions are in the Z-axis direction, and the surface-emitting laser array chip CH1 and CH2 have substantially the same configuration (including the number of light-emitting units and their arrangement) just except that the oscillation wavelengths are different from each other. In other words, the first and second lenses are substantially the same lens. Each of the surface-emitting laser array chips is equivalent to the multilayer chip of FIG. 17 from which the photo-sensing element, the sixth electrode pad, and the wiring for connecting these elements with each other are removed.

In the following description, the first surface-emitting laser array chip and the second surface-emitting laser array chip may be referred to as CH1 and CH2, respectively, and may be collectively referred to simply as channel (CH) when it is not necessary to distinguish these two channels.

In the light source module LM (type II), the relative positions of the multiple light-emitting units and the optical axis of the corresponding one of the lenses are equivalent to each other between two channels. More specifically, the center of each of the channels (center of array) is disposed on the optical axis of the corresponding one of the lenses.

Figure 18B:
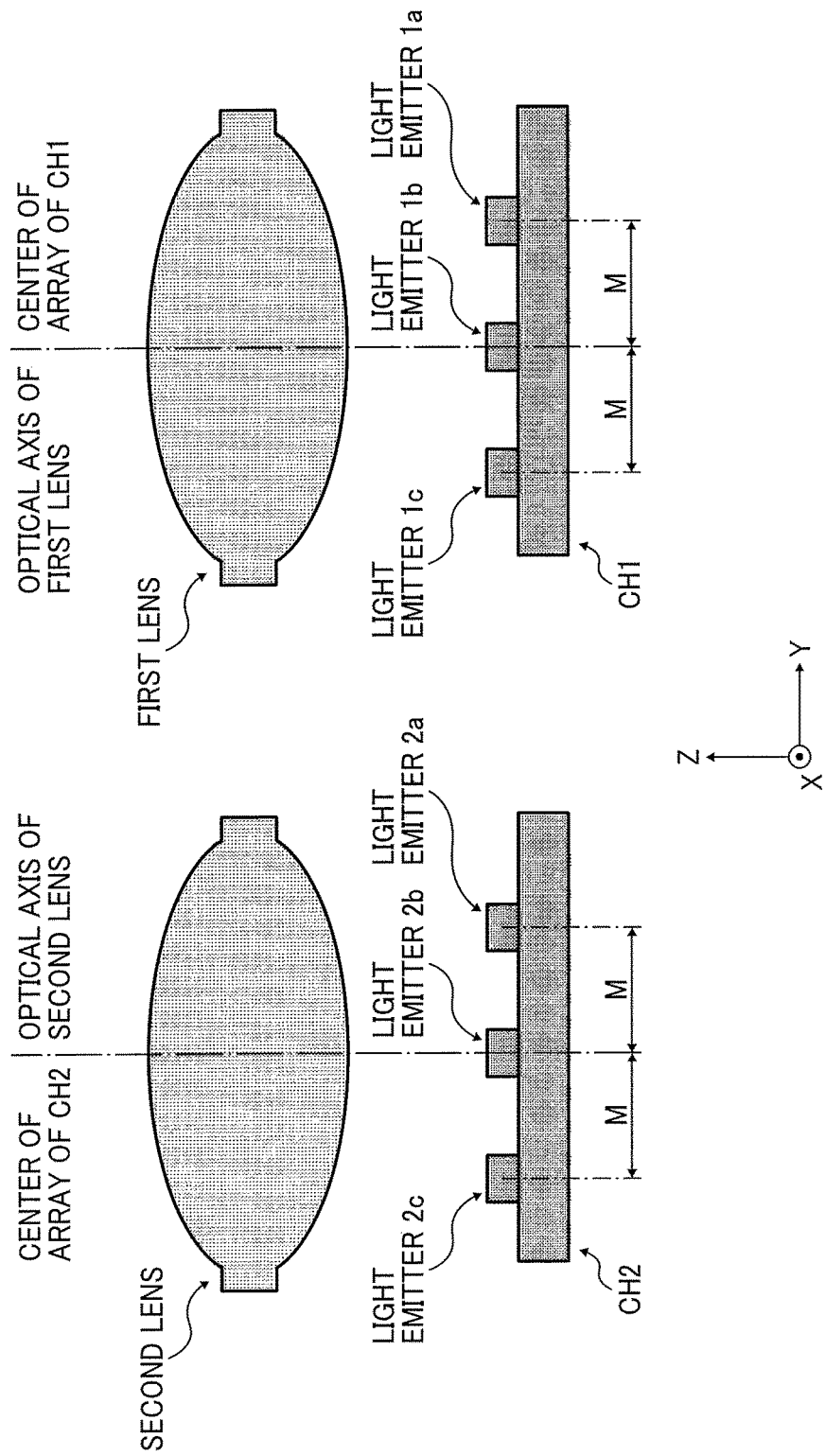

FIG. 18B is a second diagrams illustrating a light source module LM (type II) according to the second variation of the first embodiment.

Here, attention is focused on the three light-emitting units illustrated in FIG. 18B that are aligned at even intervals in the Y direction of each channel. These three light-emitting units that are aligned at even intervals M in the Y direction of CH1 are referred to as a light-emitting unit $1a$, light-emitting unit $1b$, and a light-emitting unit $1c$ in the order from +Y side to −Y side. In a similar manner, the three light-emitting units that are aligned at even intervals M in the Y direction of CH2 are referred to as a light-emitting unit $2a$, light-emitting unit $2b$, and a light-emitting unit $2c$ in the order from +Y side to −Y side. It is assumed that the light-emitting unit $1b$ and the light-emitting unit $2b$ are disposed on the optical axis of the corresponding one of the first and second lenses.

As illustrated in FIG. 18A, the prism has a symmetrical shape about the central axis (axisymmetric shape), and includes an incident plane IS that is orthogonal to the central axis, total reflection planes R1 and R2 that are oblique with reference to the central axis, and an exit plane OS that is orthogonal to the central axis.

The incident plane IS is disposed to involve the optical paths of the light rays that are emitted from the three light-emitting units $1a$, $1b$, and $1c$ of CH1 and to involve the optical paths of the light rays that are emitted from the three light-emitting units $2a$, $2b$, and $2c$ of CH2.

The total reflection plane R1 is disposed to involve the optical path of the light (light beam 1) that is emitted from the light-emitting unit $1a$ and has passed through the first lens and the incident plane IS, and the optical path of the light (light beam 2) that is emitted from the light-emitting unit $2a$ and has passed through the second lens and the incident plane IS. The incident angles of the light beams 1 and 2 on the total reflection plane R1 is equal to or greater than a critical angle.

The total reflection plane R2 is disposed to involve the optical path of the light (light beam 3) that is emitted from the light-emitting unit $1c$ and has passed through the first lens and the incident plane IS, and the optical path of the light (light beam 4) that is emitted from the light-emitting unit $2c$ of CH2 and has passed through the second lens and the incident plane IS. The incident angles of the light beams 3 and 4 on the total reflection plane R2 is equal to or greater than a critical angle.

The exit plane OS is disposed to involve the optical paths of the light rays (light beams 1 and 2) reflected on the total reflection plane R1, the light rays (light beams 3 and 4) reflected on the total reflection plane R2, the light (light beam 5) that is emitted from the light-emitting unit $1b$ of CH1 and has passed through the first lens and the incident plane IS (traveling in a straight line), and the light (light beam 6) that is emitted from the light-emitting unit $2b$ of CH2 and has passed through the second lens and the incident plane IS (traveling in a straight line), and the light beams 1 to 5 exit through (pass through) the exit plane OS. In the present embodiment, the exit plane OS serves as a contact surface that contacts the surface of a test object. For this reason, it is desired that transparent gel be provided between the exit plane OS and the surface of the test object.

In such a configuration, the two light rays with different wavelengths that are emitted from the two light-emitting units $1a$ and $2a$ in an approximately parallel state and have entered the first and second lenses are refracted by the first and second lenses, and enter the incident plane IS in an approximately parallel state. Then, these two light rays are refracted by the incident plane IS, and enter the total reflection plane R1 in an approximately parallel state. The two light rays with different wavelengths that are reflected by the total reflection plane R1 enter an approximately identical point of the test object in an approximately parallel state. In such a configuration, the positions at which the two light rays with different wavelengths enter the test object are apart from each other to some extent (by about the space between the light-emitting unit 1a and the light-emitting unit 2a).

In a similar manner, the two light rays with different wavelengths that are emitted from the two light-emitting units 1c and 2c in an approximately parallel state and have entered the first and second lenses are refracted by the first and second lenses, and enter the incident plane IS in an approximately parallel state. Then, these two light rays are refracted by the incident plane IS, and enter the total reflection plane R2 in an approximately parallel state. The two light rays with different wavelengths that are reflected by the total reflection plane R2 enter an approximately identical point of the test object in an approximately parallel state. In such a configuration, the positions at which the two light rays with different wavelengths enter the test object are apart from each other to some extent (by about the space between the light-emitting unit 1c and the light-emitting unit 2c).

In order to further improve the accuracy of the detection, it is desired that the positions at which the two light rays with different wavelengths enter the test object be identical (or made closer to each other as much as possible). In order to achieve this, it is considered to be effective to bring the optical paths of these two light rays with different wavelengths that are reflected by the total reflection plane of the prism to approximately match.

Accordingly, two reflection planes may separately be disposed on the optical paths of the two light rays from two channels with different wavelengths (see FIG. 16). However, it is difficult to bring the optical paths of these two light rays with different wavelengths to approximately match.

It may be possible to match the light exit directions of the two light rays with different wavelengths at the two lenses, but in particular, it is impossible to make the exit points of the two channels (i.e., the positions of the light-emitting units) same.

Note also that in the light source module LM (type II) as described above, the surface-emitting laser array chip may be replaced with a multilayer chip similar to the multilayer chip of the light source module LM according to the first variation of the first embodiment or the multilayer chip of the light source module LM (type I) according to the second variation of the first embodiment.

Figure 19:
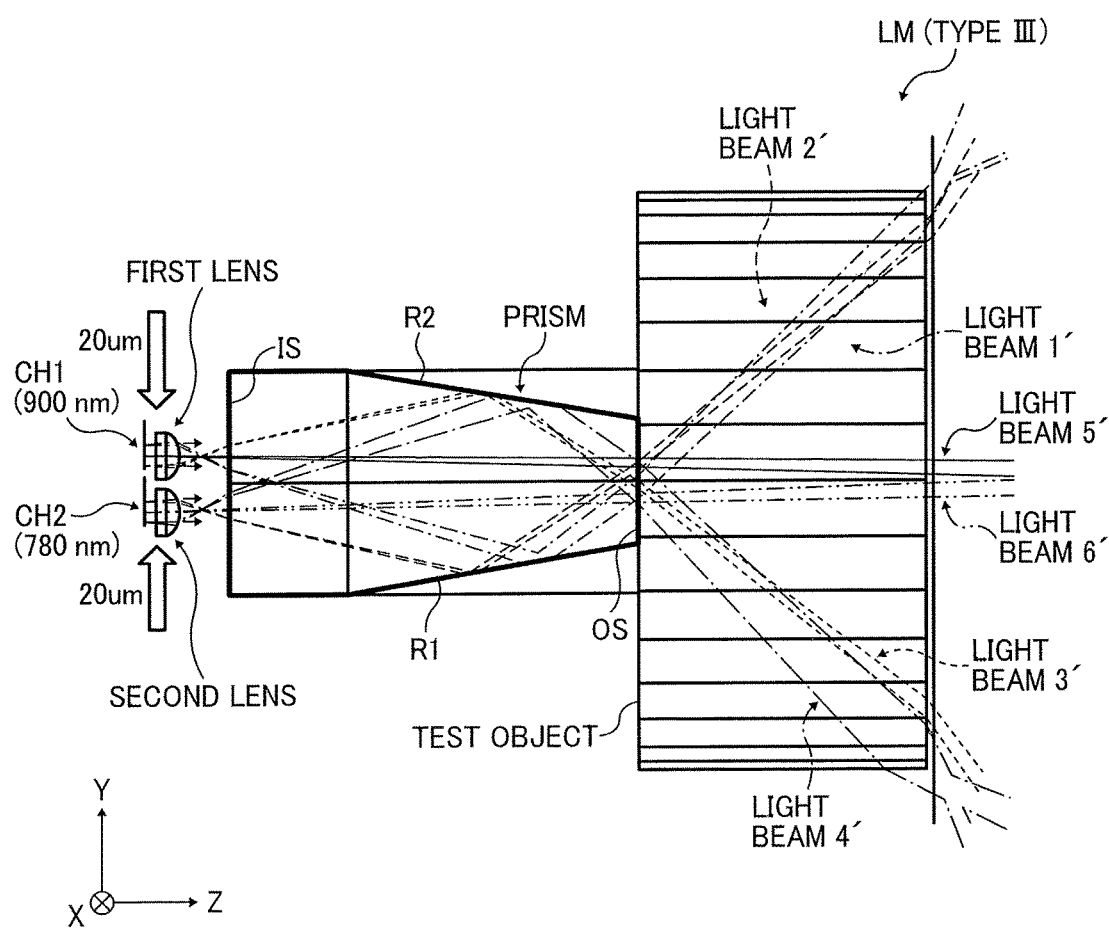
FIG. 19 is a diagram illustrating a light source module LM (type III) according to the second variation of the first embodiment.

FIG. 19 is a diagram illustrating a light source module LM (type III) according to the second variation of the first embodiment.

In the light source module LM (type III), the relative positions of the multiple light-emitting units and the optical axis of the corresponding one of the lenses are different from each other between two channels. The light source module LM (type III) is different from the light source module LM (type II) illustrated in FIG. 18A only in this respect, and the light source module LM (type III) is equivalent to the light source module LM (type II) in the other respects.

In the light source module LM (type III), the space between the centers of the two channels (the space between the centers of the arrays) is about 1.4 mm. These relative positions of the two channels are made close to each other as much as possible in view of a pad portion or the like that is used when wire bonding is performed.

Note that each of the channels have 1 mm sides, and two channels are in close proximity to each other with the space (gap) of about several hundred micrometers (μm). In the present embodiment, such a close placement is achieved by modifying, for example, the collet of a die bonder device.

The light-emitting units (surface emitting lasers) of the two channels are manufactured by performing semiconductor processes with an identical mask, and the positions of the light-emitting units can be controlled with the precision of equal to or smaller than 0.5 μm.

In a similar manner to the light source module LM (type II), the first surface-emitting laser array chip (900 nm) and the second surface-emitting laser array chip (780 nm) of the light source module LM (type III) are manufactured with the same level of precision and has the same layout.

The two light rays with different wavelengths that are emitted from the two channels whose centers are about 1.4 mm apart and have passed through the corresponding lens, as described above, are reflected by the same total reflection plane of the prism, and enters the test object (for example, a live subject).

In the configuration of the light source module LM (type II), the two light rays that are emitted from the associated CH1 and CH2 enter the test object (for example, a live subject) at approximately equal distances (about 1.4 mm) maintaining a state where these light rays are parallel to each other. Accordingly, the gap between the two positions at which the light rays enter the test object is kept at about 1.4 mm. If the gap between these incident positions is large as described above, the resolution in the functional near-infrared spectroscopy (fNIRS), in which the cerebral blood flow is detected by performing inverse problem estimation, decreases.

In order to avoid such a situation, a method of bringing the optical paths of these two light rays with different wavelengths to approximately match to match the incident positions, without an increase in the cost of installation, was studied. As a result, a technique in which the center of each channel (the center of each array) is shifted by several micrometers (μm) to several hundreds of micrometers (μm) (preferably, several tens of micrometers (μm)) with reference to the optical axis of the corresponding one of the lenses was proposed, and this technique was provided for the light source module LM (type III).

The details are described below with reference to FIG. 20.

Figure 20:
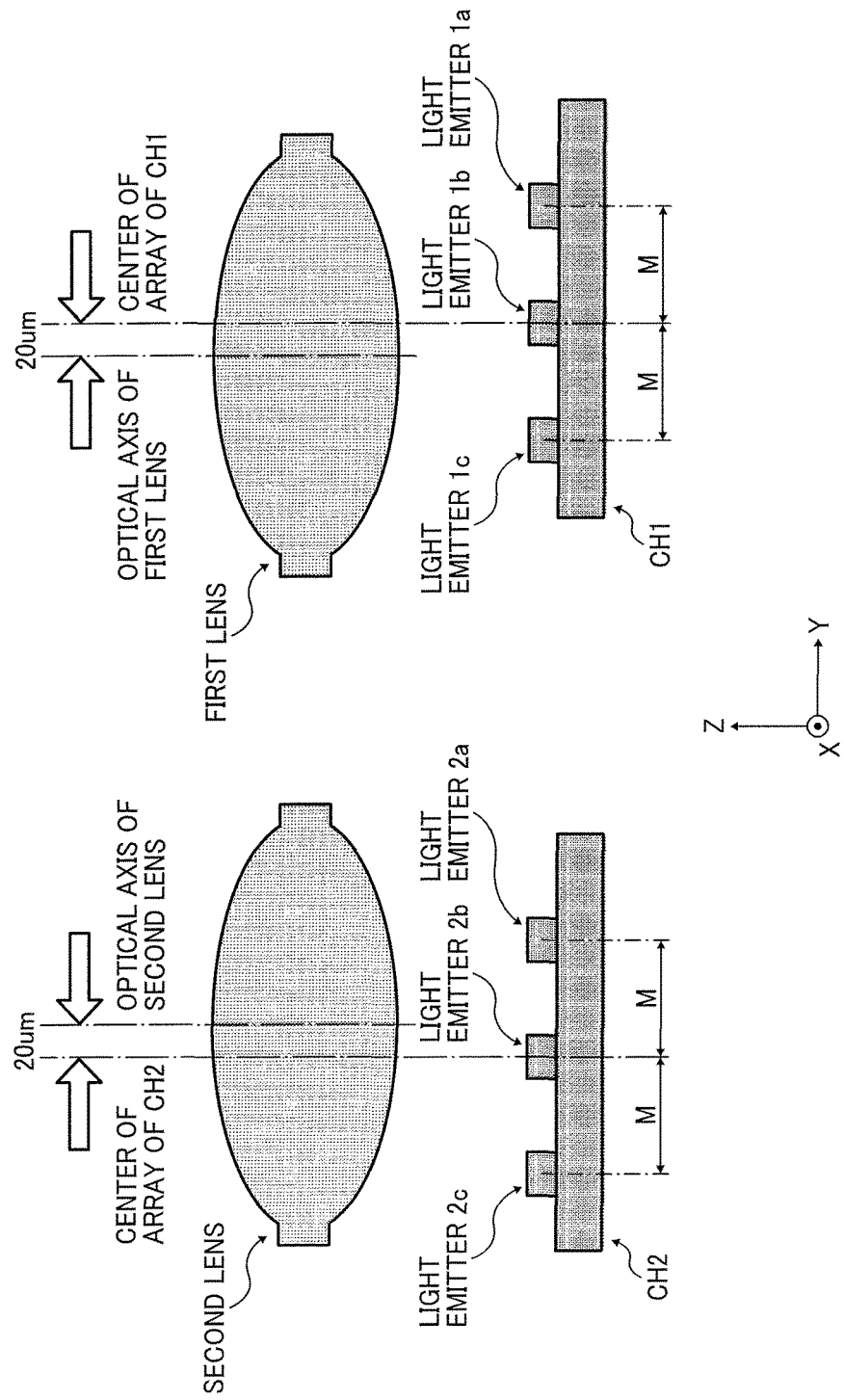
FIG. 20 is a diagram illustrating relative positions of a lens and a surface-emitting laser array chip in the light source module LM (type III), according to the second variation of the first embodiment.

FIG. 20 is a diagram illustrating relative positions of a lens and a surface-emitting laser array chip in the light source module LM (type III), according to the second variation of the first embodiment.

In the present embodiment, the center of each channel is displaced from the optical axis of the corresponding one of the lenses by about 20 μm. The degree of displacement is not limited to 20 μm, but may be varied where appropriate.

Figure 21:
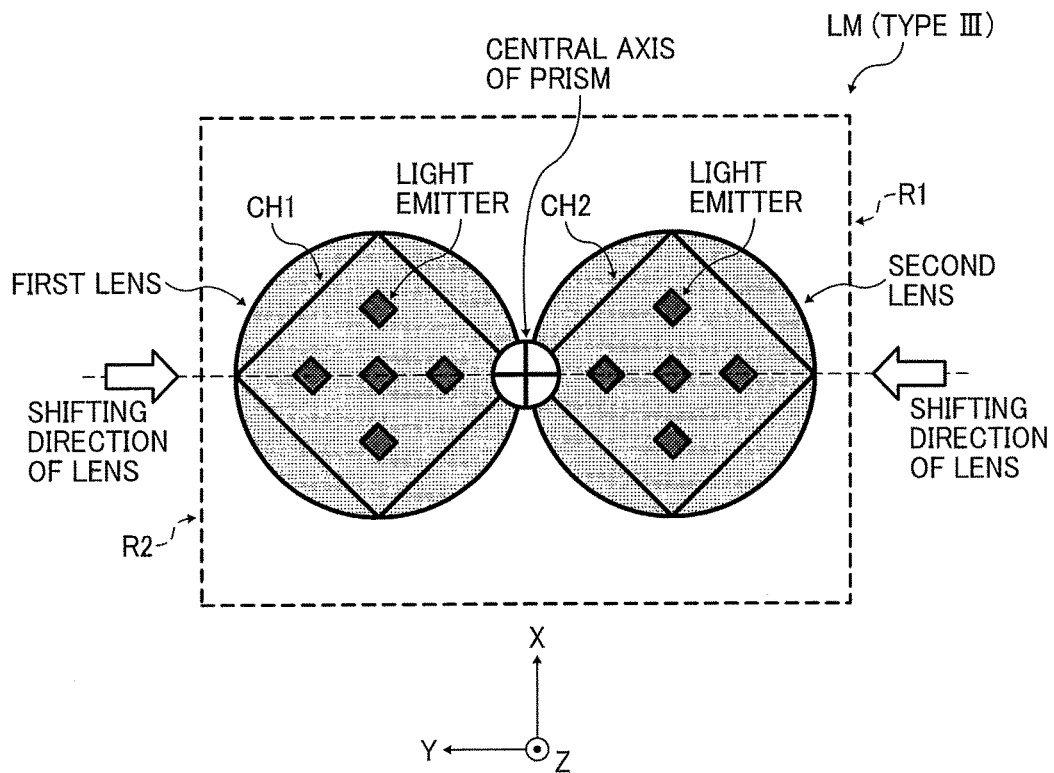
FIG. 21 is a diagram illustrating relative positions of a lens, a surface-emitting laser array chip, and a prism in the light source module LM (type III), according to the second variation of the first embodiment.

FIG. 21 is a diagram illustrating relative positions of a lens, a surface-emitting laser array chip, and a prism in the light source module LM (type III), according to the second variation of the first embodiment.

In the present embodiment, the space between the centers of two channels (relative positions of two channels) is not changed, but the lenses that correspond to the respective channels are displaced. It is desired that the directions in which the lenses are to be shifted with reference to the corresponding channels be determined so as to be axially symmetrical (rotational symmetry) about the central axis of the prism that is an optical element in common (see FIG. 21).

In other words, the arrangement of the two channels and the first and second lenses are not limited to the arrangement illustrated in FIG. 21 as long as these elements are disposed axially symmetrical about the central axis of the prism (optical element in common).

In the present example, by way of example, the two channels are disposed across the central axis of the prism in the Y direction, such that the centers of the two channels are axially symmetrical (point symmetry) about the central axis of the prism. Each of the channels includes five light-emitting units (vertical-cavity surface-emitting lasers (VC-SEL)), and these five light-emitting units are separately disposed at the center (center of the array) and the four vertices of the square in which one of the diagonal lines is parallel to the Y direction.

For example, the space between the centers of the two channels is 1.4 mm, and the pitch diameter of each lens is 0.8 mmφ. Moreover, the focal length f of each lens is, for example, 600 µm. In the present example, the directions in which the first and second lenses are shifted with reference to the two channels CH1 and CH2 are in the directions where the first and second lenses move closer to one another as illustrated in FIG. 21. In the present example, the first lens is displaced by about 20 µm in the −Y direction from a state in which the optical axis of the first lens passes through the center of CH1, and the second lens is displaced by about 20 µm in the +Y direction from a state in which the optical axis of the second lens passes through the center of CH2. As a result, the center of CH1 is displaced from the optical axis of the first lens by about 20 µm, and the center of CH2 is displaced from the optical axis of the second lens by about 20 m.

In this configuration, the optical path of the light (light beam 1') that is emitted from the light-emitting unit 1a of CH1 and enters the total reflection plane R1 after passing through the first lens and the incident plane IS is not parallel to the optical path of the light (light beam 2') that is emitted from the light-emitting unit 2a of CH2 and enters the total reflection plane R1 after passing through the second lens and the incident plane IS, and these two optical paths get close to each other as they get close to the total reflection plane R1 (see FIG. 19). Assuming that the incident angles at which the two light rays enter the corresponding lenses are equal to each other, the angles of refraction of these light rays increase as the positions at which the light rays enter the lenses are distant from the optical axes.

In a similar manner, the optical path of the light (light beam 3') that is emitted from the light-emitting unit 1c of CH1 and enters the total reflection plane R2 after passing through the first lens and the incident plane IS is not parallel to the optical path of the light (light beam 4') that is emitted from the light-emitting unit 2c of CH2 and enters the total reflection plane R2 after passing through the second lens and the incident plane IS, and these two optical paths get close to each other as they get close to the total reflection plane R2 (see FIG. 19).

Moreover, the optical path of the light (light beam 5') that is emitted from the light-emitting unit 1b of CH1 and enters the exit plane OS after passing through the first lens and the incident plane IS gets close to the optical path of the light (light beam 6') that is emitted from the light-emitting unit 2b of CH2 and enters the exit plane OS after passing through the second lens and the incident plane IS, as these two optical paths get close to the exit plane OS (see FIG. 19).

The optical paths of the two light rays (light beams 1' and 2') with different wavelengths that are reflected by the total reflection plane R1 and not parallel to each other intersect near the exit plane OS that is a contact surface with a test object. Moreover, the optical paths of the two light rays (light beams 3' and 4') with different wavelengths that are reflected by the total reflection plane R2 and not parallel to each other intersect near the exit plane OS that is a contact surface with a test object (see FIG. 19).

Accordingly, as illustrated in FIG. 19, the optical paths of the two light rays (light beams 1' and 2') with different wavelengths that are reflected by the total reflection plane R1 approximately overlap one another, and the positions at which the two light rays enter the test object become the same. Moreover, the optical paths of the two light rays (light beams 3' and 4') with different wavelengths that are reflected by the total reflection plane R2 approximately overlap one another, and the positions at which the two light rays enter the test object become the same. Further, the position at which the two light rays (light beams 5' and 6') with different wavelengths, which heads for the exit plane OS without being reflected on either one of the total reflection planes, enters the test object are approximately the same.

The laser-beam bundle including the light beams 1' and 2', the laser-beam bundle including the light beams 3' and 4', and the laser-beam bundle including the light beams 5' and 6' are not parallel to each other, and each of the laser-beam bundles enters an approximately identical point of the test object.

The light rays that are emitted from the two light-emitting units of CH1 other than the light-emitting units 1a, 1b, and 1c, as illustrated in FIG. 21, and the light rays that are emitted from the two light-emitting units of CH2 other than the light-emitting units 2a, 2b, and 2c pass through the incident plane IS, and are directly exited through the exit plane OS. As a result, these light rays enter an approximately identical point of the test object in a similar manner to the laser-beam bundles as described above.

In the light source module LM (type III) described above, lenses are simply shifted (displaced) with reference to the corresponding channels to bring the optical paths of two light rays with different wavelengths to approximately match to match the incident position of these light rays. By matching the incident positions of the two light rays with different wavelengths, the position of the cerebral blood flow can be measured with high precision in a near-infrared spectroscopy (NIRS) device that performs an inverse problem estimation.

Alternatively, if a member such as a half mirror is used to achieve an advantageous effect as in the light source module LM (type III) instead of shifting lenses, it ends up with an increase in implementation cost as the number of optical components that require high-precision alignment increases.

In the light source module LM (type III), the optical axes of the first and second lenses are displaced (shifted) from the center points of the corresponding CH1 and CH2. However, no limitation is intended therein.

For example, only one of the optical axes of the first and second lenses may be displaced (shifted) from the center point of the corresponding channel, or the other optical axis may be disposed to pass through the center point of the corresponding channel.

Alternatively, a channel may be shifted with reference to the corresponding lens instead of or in addition to shifting a lens with reference to the corresponding channel.

Moreover, the directions in which the first and second lenses are shifted with reference to the corresponding CH1 and CH2 may be varied. For example, the first and second lenses may be shifted in the same direction, or the first and second lenses may be shifted in the opposite direction (i.e., the direction in which the first and second lenses get close to each other or away from each other).

The amounts of shifting (amount of displacement) of the first and second lenses with reference to the corresponding CH1 and CH2 may be equal to each other or different from each other.

In short, the relative positions of multiple light-emitting units and the optical axis of the corresponding one of the lenses are to be varied from each other between two channels, such that the optical paths of two light rays with different wavelengths that are emitted from CH1 and CH2 approximately overlap one another.

More specifically, it is desired that the relative positions of multiple light-emitting units and the optical axis of the corresponding one of the lenses are to be varied from each other between two channels such that the optical paths of two light rays with different wavelengths that are emitted from CH1 and CH2 and have passed through the first and second lenses gradually get close to each other and optical paths of these light rays intersect near the contact surface of the test object in the light source module LM (type III) (near the exit end in the light source module LM (type III)).

Note also that in the light source module LM (type III) as described above, the surface-emitting laser array chip may be replaced with a multilayer chip similar to the multilayer chip of the light source module LM according to the first variation of the first embodiment or the multilayer chip of the light source module LM (type I) according to the second variation of the first embodiment.

Next, the reason why a surface-emitting laser array is adopted as the light source of the optical sensor 10 is described. In the surface-emitting laser array, the multiple channels can two-dimensionally be arranged in close proximity to each other, and the light emission of the channels can be controlled in an in an independent manner. Further, the path of the exit light can be changed by disposing a small lens in the proximity of the channels.

For optical sensors provided for DOT, precise control of the incident angle to the test object is desired. As commonly-used light-emitting diodes (LED) have a wide angle of departure, a lens needs to have an aspherical surface in order to achieve collimated beam with high accuracy. Moreover, a commonly-used laser diode (LD) (end-surface emitting laser) has an asymmetrical angle of departure. For this reason, in order to achieve collimated beam with high accuracy, two lenses such as lenses with varying curvatures in length and breadth or cylindrical lenses need to be combined. Such a configuration is complicated, and advanced implementation is required.

By contrast, a surface emitting laser has an almost perfectly circular far field pattern, and only one spherical lens needs to be disposed to form a collimated beam. When the coherent light emitted from the LD is used, speckles occur in the test object (scatterer) and the scattered lights interfere with each other. Such a speckle pattern affects the measurement as a noise.

When the bloodstream inside the brain is observed, for example, by DOT, a very large number of scatterings occur. For this reason, when the bloodstream inside the brain is observed, the measurement is not very much affected by a speckle pattern. However, the measurement is still affected by a return light where the light reflected by the surface of the skin directly returns to the light source. Such a return light may make the oscillation state inside the LD unstable, and in such a case, the stable operation is disabled. When coherent light is to be used in a stable manner, for example, in an optical disk, a wave plate or the like is used such that a specular reflection light does not become a return light. However, it is difficult to remove a return light of the reflection light from the scatterer.

In the case of a surface-emitting laser array chip, a plurality of light rays can simultaneously be emitted to a minute area, and the interference of the return light can be reduced (see, for example, JP-2012-127937-A).

Figure 22:
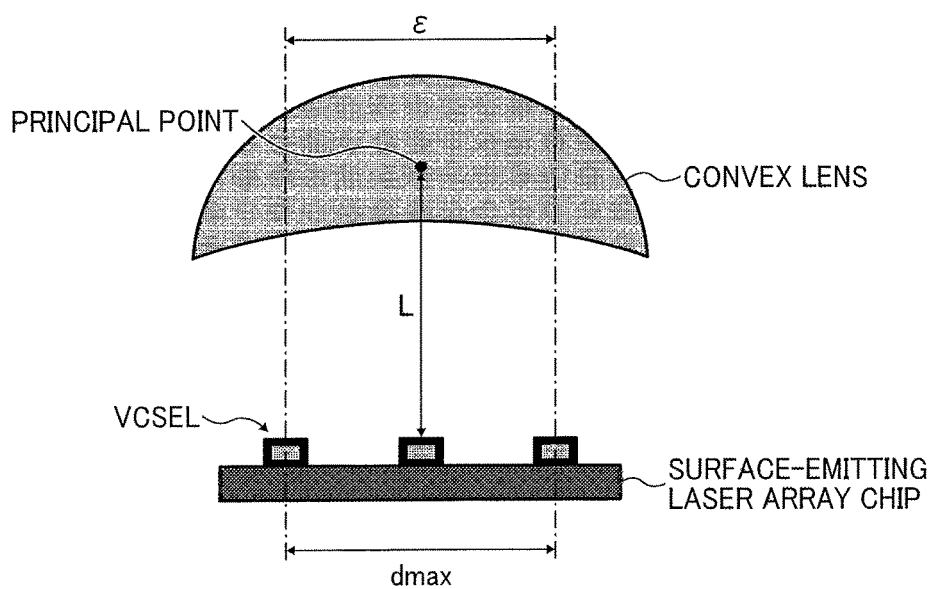
FIG. 22 is a first diagram illustrating a first additional configuration of the light source module according to the first and second variations of the first embodiment.

FIG. 22 is a first diagram illustrating a first additional configuration of the light source module according to the first and second variations of the first embodiment.

In the light source module LM (type II) or the light source module LM (type III) according to the second variation of the present embodiment, a convex lens is arranged on the optical path of the light emitted from the surface-emitting laser array chip (see FIG. 22). This convex lens may be referred to simply as a lens in the following description.

This convex lens has the 1 mm diameter, and has the 600 micrometer (μm) effective diameter. Moreover, the focal length f of the convex lens is 600 μm. The surface-emitting laser array chip is a chip with 1 mm angles, and the distance dmax between the centers of the two most distant channels in the surface-emitting laser array chip is 600 μm. As described above, by matching the dmax and the effective diameter E, the diameter of the convex lens can be minimized.

In the present embodiment, the convex lens and the surface-emitting laser array chip are registered such that the distance L between the principal point (optical center) of the convex lens and the light-emitting surface (exit plane) of the surface-emitting laser array chip in the optical-axis direction of the convex lens becomes, for example, 300 μm. That is, $f \neq L$.

In this configuration, a phenomenon (return light phenomenon) can be avoided in which the light emitted from the surface-emitting laser array chip and passed through the convex lens is reflected by a prism or the like by specular reflection and then is concentrated onto the surface-emitting laser array chip. As described above, a return light does not occur. Accordingly, the amount of light emission of each channel of the surface-emitting laser array chip can be stabilized.

When it is not necessary to consider the effect of a return light (i.e., when a higher resolution is not requited for the NIRS), it is satisfactory even if f=L.

Figure 23:
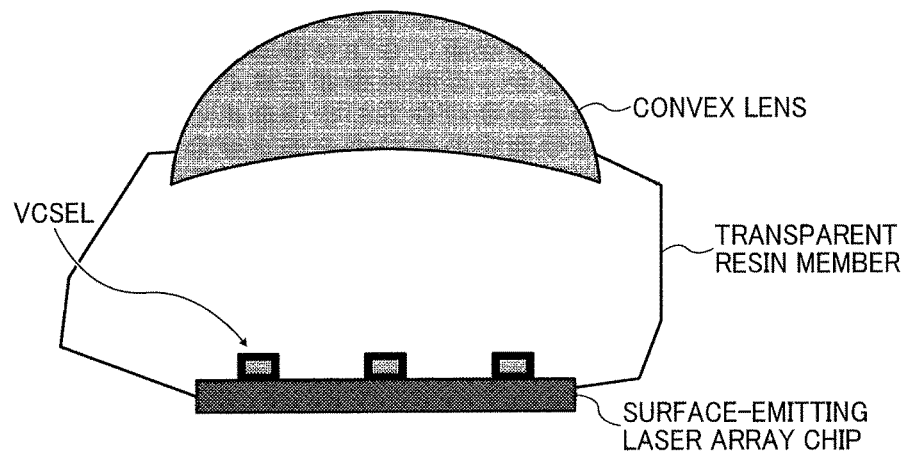
FIG. 23 is a second diagram illustrating a second additional configuration of the light source module according to the first and second variations of the first embodiment.

FIG. 23 is a second diagram illustrating a second additional configuration of the light source module according to the first and second variations of the first embodiment.

As illustrated in FIG. 23, the space between the convex lens and the surface-emitting laser array chip is filled with a transparent resin so as not to include any airspace. In the present embodiment, the transparent resin is a resin having the refractive index equivalent to that of the convex lens (for example, a thermosetting epoxy resin). Accordingly, the refractive index does not change at the boundary of the interface between the convex lens and the surface-emitting laser array chip. The transparent resin may be formed by a metal mold before the convex lens is attached, or may be implanted after the convex lens is attached.

As the space between the convex lens and the surface-emitting laser array chip is filled with the transparent resin as described above, the reflection of the light emitted from the surface-emitting laser array chip on the surface of convex lens on the surface-emitting laser array chip side, i.e., the occurrence of the return light, can be prevented. As the occurrence of the return light is prevented, the amount of light emission of the channels can be stabilized.

As the amount of light of the channels is stabilized, the signal-to-noise ratio (S/N) of the measurement system improves, and the high-precision NIRS measurement and high resolution can be achieved.

Figure 24:
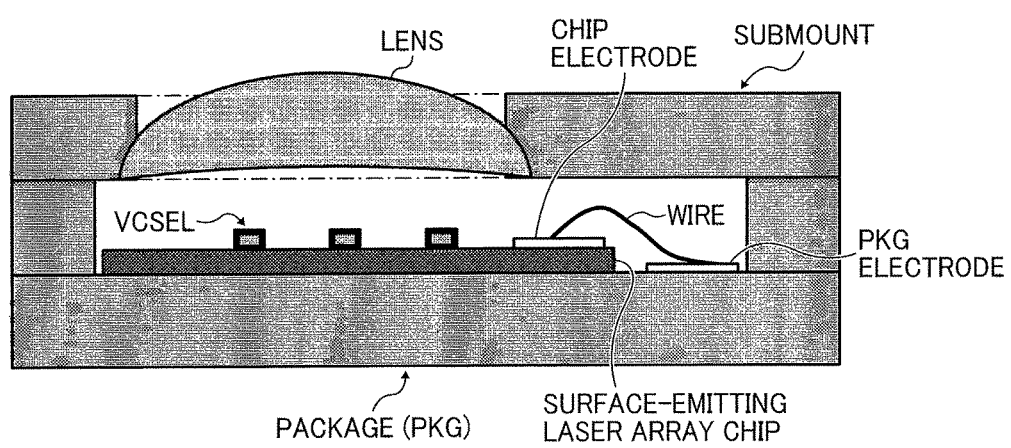
FIG. 24 is a third diagram illustrating a third additional configuration of the light source module according to the first and second variations of the first embodiment.

FIG. 24 is a third diagram illustrating a third additional configuration of the light source module according to the first and second variations of the first embodiment.

As illustrated in FIG. 24, the surface-emitting laser array chip is mounted on the package, and the convex lens is attached to the package via the submount. In the surface-emitting laser array chip, the electrodes (chip electrodes) on the chip are electrically connected to the package (PKG) electrode on the package through a wire. The wire has a height of several tens of micrometers, and is designed so as not to interfere with the submount. The attached position L of the convex lens (i.e., the distance between the light-emitting surface of the surface-emitting laser array chip and the principal point of the convex lens) is subject to constraints of the height of the wire. More specifically, when a wire is used in the above configuration, the wire may need to avoid the submount in the structure, or the height of the wire may need to be equal to or less than 100 μm. In other words, it is desired that −100 μm<f−L<0. Note that the illustration of the transparent resin illustrated in FIG. 23 is omitted in FIG. 24.

Note also that in the configurations illustrated in FIG. 22 to FIG. 24, the surface-emitting laser array chip may be replaced with a multilayer chip similar to the multilayer chip according to the first variation of the first embodiment or the multilayer chip of the light source module LM (type I) according to the second variation of the first embodiment.

The light emitted from the exit plane of the surface emitting laser is approximately circular, and the divergence angle is about 5 degrees in half value width. As the laser beams of the LD known in the art is elliptic, the installation error in the rotation direction needs to be taken into consideration. However, in the surface emitting laser, such an installation error does not need to be taken into consideration. Moreover, as the light emitted from the exit plane of the surface emitting laser is approximately circular, it is easier to perform approximation or the like utilizing the symmetry of the circular shape when an optical simulation is performed to solve a reverse problem.

The laser beam emitted from the surface emitting laser is refracted by the convex lens disposed nearby. The refraction angle is determined by the relative positions of the surface emitting laser and the center of the lens (i.e., the optical axis of the lens). Accordingly, a desired refraction angle can be obtained by appropriately arranging the position of the lens and the position of the multilayer chip or the surface-emitting laser array chip of each group.

In the second variation, the relative positions of the channel and the optical axis of the convex lens are determined such that the refraction angle becomes about 20 degrees. In the multilayer chip or the surface-emitting laser array chip, the light emission of the channels can be controlled in an in an independent manner. Accordingly, the direction of the light that is emitted from the light source modules LM can be changed by selecting the channel that is to emit the light.

Figure 25:
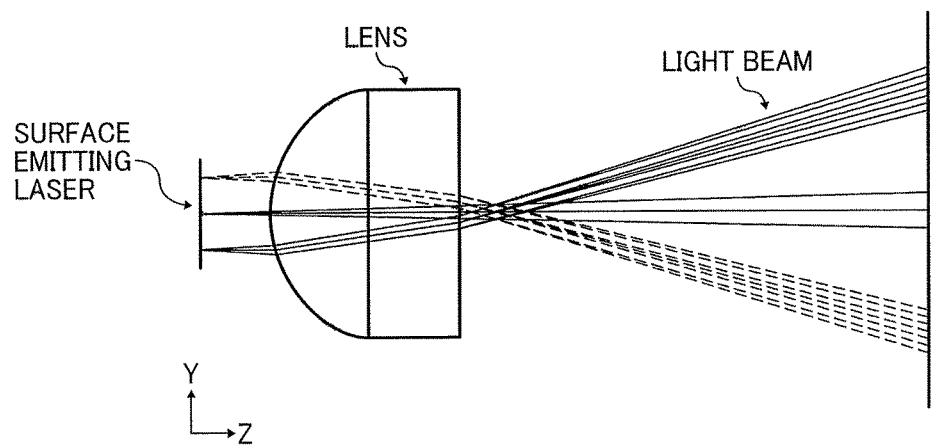
FIG. 25 illustrates an example of the light beams that are optically designed by an optical simulator, according to the first embodiment of the present invention.

FIG. 25 illustrates an example of the light beams that are optically designed by an optical simulator, according to the present embodiment.

In FIG. 25, three channels that simulate a surface emitting laser are provided, and a 1 mm lens in diameter with f=600 micrometer (μm) is disposed in the proximity of these three channels. One of the three channels is disposed on the optical axis of the lens, and the other two channels are separately disposed on two sides of the optical axis of the lens. The light rays emitted from the other two channels that are not on the optical axis are refracted by the lens, and the propagation direction (path) is bent. More specifically, the light rays emitted from the other two channels that are not on the optical axis are exited with the angle of about 20 degrees with reference to the optical axis of the lens, and the these two light rays are exited in opposite directions with reference to the optical axis.

In the present embodiment, the light source module LM is designed such that the incident angle at which the light enters the test object becomes about 55 degrees. More specifically, as illustrated in FIG. 16, in the light source module LM, the multiple light rays exiting from the convex lens in the direction with the oblique angle of about 20 degrees with reference to the optical axis are separately deflected by multiple prisms. Accordingly, the angles of the multiple light rays with reference to the optical axes of the corresponding lenses are changed from about 20 degrees to about 55 degrees, and the incident angle at which the light rays enter the surface of the test object becomes about 55 degrees.

Note that the prism may be made of any material as long as it can reflect light. For example, the prism may be made of a glass substrate on which a metal film is formed. Alternatively, for example, a prism in which total internal reflection caused by a difference in refractive index is utilized may be adopted.

Figure 26:
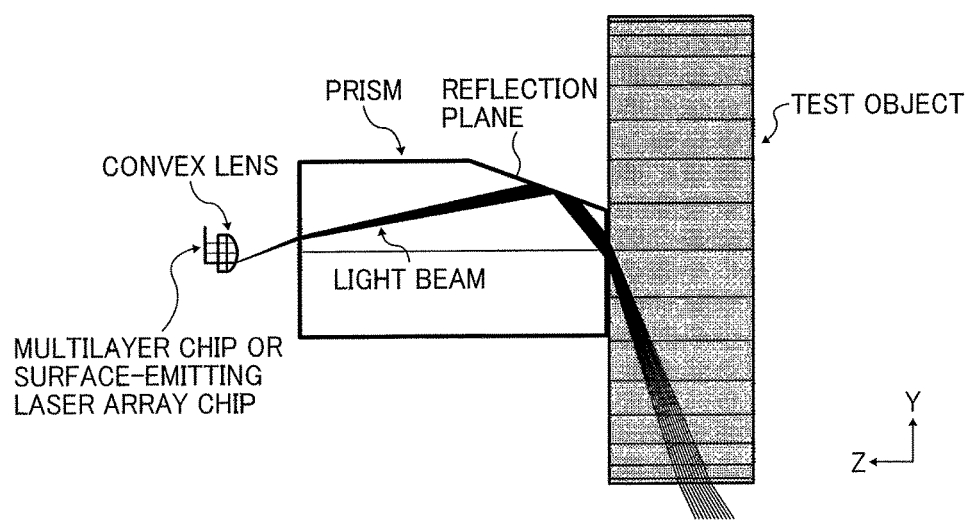
FIG. 26 illustrates an example of the result of the optical simulation according to the first embodiment of the present invention.

FIG. 26 illustrates an example of the result of the optical simulation according to the first embodiment of the present invention.

The light beam emitted from the surface-emitting laser element is refracted by the convex lens, and then enters the prism.

In the present embodiment, the material of the prism is BK7. However, the prism may be made of any known optical material. The light that has entered the prism is reflected by the side (reflection plane) of the prism by total internal reflection, and enters the test object at an incident angle of about 55 degrees. In other words, the light that has passed through the convex lens is deflected by the prism in such a manner that the incident angle at which the light enters the test object becomes about 55 degrees. In this configuration, a transparent gel intervenes between the prism and the test object so as to prevent the dispersion of the light on the interface between the prism and the test object. The light rays emitted from the multilayer chip or the surface-emitting laser array chips becomes a plurality of light rays that are not parallel to each other after passing through the convex lens, and these light rays are reflected by the prisms and enter the test object. As a result, a plurality of approximately collimating light rays that are not parallel to each other enters the identical point of the test object (see FIG. 26).

By the Snell law (the law of reflection), the propagation angle of the light beam in the test object changes from about 55 degrees to about 60 degrees due to the difference in refractive index between the prism and the test object.

In the optical system for which the convex lens and the prism are provided, the positions of the channels of the multilayer chip or the surface-emitting laser array chip are different from each other. Accordingly, the propagation angles of the light rays in the test object are adjustable. In the present embodiment, the centers of the channels are displaced from the optical axis of the convex lens by about 200 μm. Accordingly, the propagation angles of the light rays emitted from the channels in the test object can be adjusted to about 60 degrees. As a result, the multiple light rays emitted from the multiple channels exit from a plurality of different positions on the exit plane of the convex lens as a plurality of approximately collimating light rays that are not parallel to each other.

Figure 27:
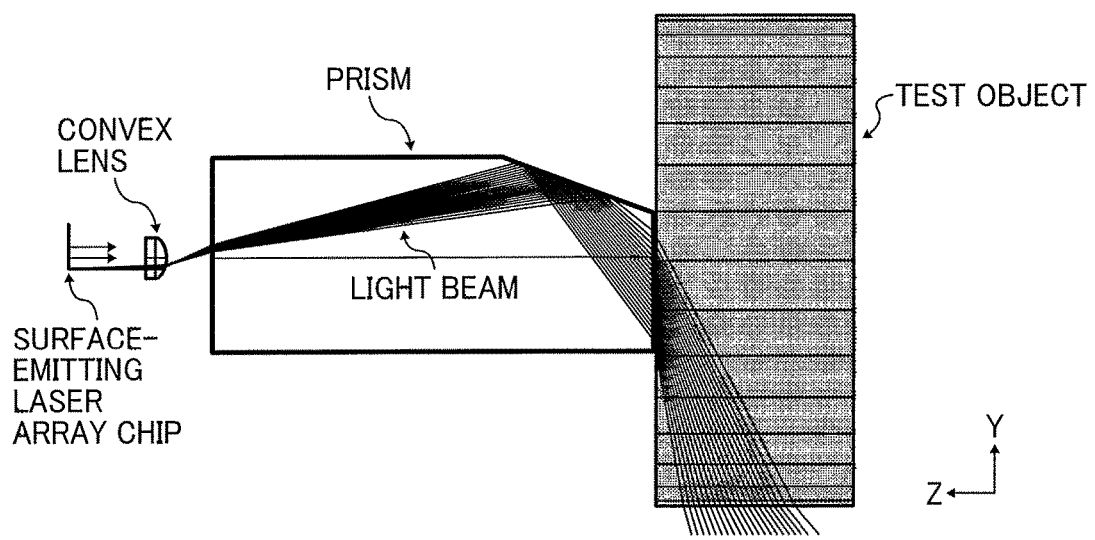
FIG. 27 illustrates an example of the result of the optical simulation according to a control sample.

FIG. 27 illustrates, as a control sample, an example of the result of the optical simulation where the lens is configured such that the focal length f=600 m and the attached position L=1.6 mm.

When the difference between L and f becomes equal to or greater than 1 mm, as illustrated in FIG. 27, the laser beam diverges too widely. In such cases where the laser beam diverges in an excessive manner as described above, the incident plane of the test object needs to be broadened. However, the practical size of the incident plane of the test object in the NIRS is actually about φ2 mm at the maximum. This restriction is present because the space among the roots of the hairs of a human is about 2 mm and the hairs optically disturb the NIRS when the dimension is wider than the above. With such disturbance, the NIRS with high resolution cannot be achieved. In short, it is desired that the difference between L and f be shorter than 1 mm.

The first and second lenses illustrated in FIG. 16 are directly attached to a ceramic package on which the first multilayer chip and the second multilayer chip mounted, such that these lenses are disposed at designed positions in a precise and stable manner.

In FIG. 25, the convex surface of the lens is directed to the surface emitting laser side. However, the direction of the convex lens may be the other way around. When the lens is arranged such that the convex surface of the lens is directed to the surface emitting laser side and the planar portion of the lens is directed to the test object as illustrated in FIG. 25, the distance between the lens and the multilayer chip or the surface-emitting laser array chip can be lengthened. In the chip implementation processes, it is desired that the allowed distance be long to a certain extent. When the allowed distance is sufficiently long, the interference of parts or an arm that picks up the parts in the implementation processes can be prevented.

The lens may be any optics as long as it can refract the light. For example, a gradient index (GRIN) lens that utilizes the refractive distribution of an optical fiber may be used for the lens. When such a GRIN lens is adopted, as known in the art, a low-cost lens with a small spherical aberration and a small f number can be selected compared with when a spherical lens is adopted.

In the second variation, the light enters the edge of the lens rather than the center of the lens. For this reason, it is desired that the spherical aberration be smaller.

Figure 64:
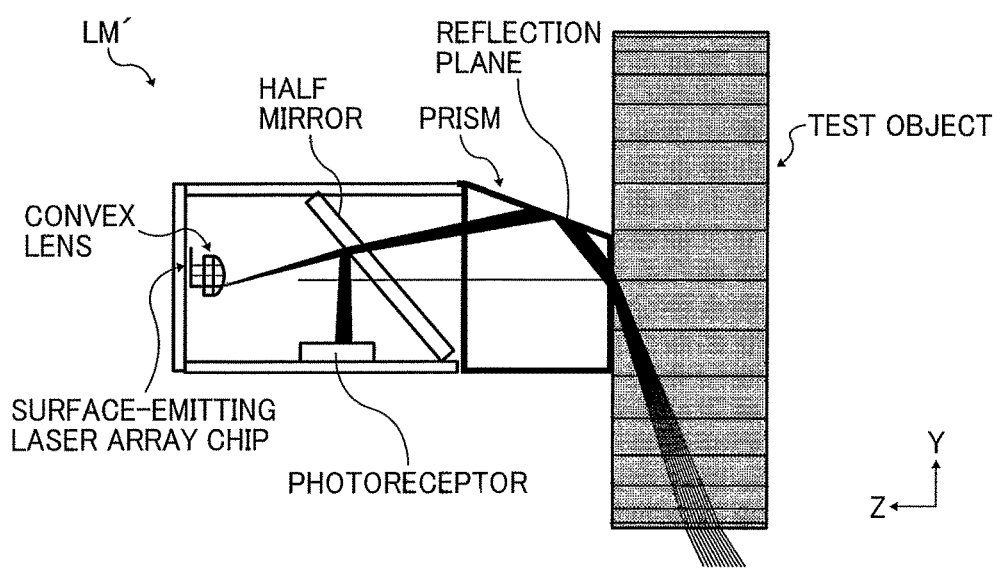
FIG. 64 is a diagram illustrating a monitoring method according to a sixth related art device.

FIG. 64 is a diagram illustrating a light source modules LM' capable of monitoring the quantity of exiting light, according to a sixth related art device.

In the light source module LM' of FIG. 64, the light that is emitted from the surface-emitting laser array chip is branched into transmission light and reflection light by a half mirror, and the reflection light is received by a photoreceptor. Accordingly, the quantity of light emission of the surface-emitting laser array chip can be continuously monitored. When the light quantity decreases due to, for example, degrading of the surface emitting laser, the amount of electric current is consistently adjusted to achieve accurate light quantity of light emission. However, the light source module LM' requires the installation of a half mirror inside the module, and the half mirror needs to be stably fixed so as not to be displaced. For the reasons as described above, accurate monitoring of light quantity leads to increases in cost.

By contrast, as illustrated in FIG. 17, in the light source module LM according to the first variation of the first embodiment or the light source module LM (type I) according to the second variation of the first embodiment, the surface-emitting laser element and the photo-sensing element that monitors the quantity of light from the surface-emitting laser element are disposed inside the multilayer chip. In this configuration, a half mirror is unnecessary and the light quantity can be monitored in a stable manner. Accordingly, increases in cost are prevented, and the quantity of light from the surface-emitting laser element can be controlled with a high degree of precision. Further, the distribution of light absorbers (for example, the distribution of cerebral blood flow) can be measured with a high degree of precision.

As described above, each of the light source modules LM (type I, type II, and type III) according to the second variation of the first embodiment emits a plurality of bundles of light rays that are not parallel to each other (see FIG. 16, FIG. 18A, FIG. 18B, and FIG. 19). From the light source modules LM (type I and type II), two light rays with different wavelengths, where the optical paths are approximately parallel to each other and are close to each other, are emitted (see FIG. 16, FIG. 18A, and FIG. 18B). From the light source module LM (type III) according to the second variation, two light rays with different wavelengths, where the optical paths are not parallel to each other and approximately overlap one another, are emitted (see FIG. 19).

Then, these bundles of light rays that are not parallel to each other emitted from the light source modules LM (type I, type II, and type III) enter an approximately identical point of the test object (see FIG. 16, FIG. 18A, FIG. 18B, and FIG. 19). The two light rays emitted from the light source module LM (type III), where the wavelengths are different from each other and the optical paths approximately overlap one another, enter the identical point of the test object (see FIG. 19).

For example, when the light source modules LM are disposed at about 60 mm intervals, the term "approximately identical point" described above indicates an approximately identical point with reference to such 60 mm. More specifically, a plurality of positions that are separated from each other by about several millimeters are considered to be approximately identical points.

The term "identical point" described above indicates a higher similarity than the term "approximately identical point", but does not always mean exactly the identical point. More specifically, a plurality of positions that are separated from each other by the degree equal to or shorter than 1 millimeter are considered to be the identical points.

The expression "optical paths approximately overlap one another" as described above indicates that the angle that the two angles that are not parallel to each other form is equal to or smaller than 10 degrees. Note that in order to increase the degree of conformity of the optical paths as much as possible, it is desired that the angle that the two angles that are not parallel to each other form be equal to or smaller than 1 degree.

In an algorithm for solving a reverse problem, an optical simulation where the position of the light source module LM is set is performed. In such an optical simulation, if the shifting of the position at which the light enters the test object is precisely set, no error occurs in the estimation of the reverse problem.

However, if it is desired that the probes be disposed with high density and with the space thereamong being equal to or wider than 10 mm as in, for example, JP-2014-083069-A, the multiple light source modules LM need to be disposed independently. Note that such an operation of disposing a plurality of light source modules LM is very much a complicated operation where the hairs need to be moved away on a one-hair-by-one-hair basis, and such complicated operation increases as the number of light source modules LM increases.

In the present embodiment, as will be described later in detail, the installation of only one light source module LM enables the acquisition of the amount of information that is equivalent to that obtained by the installation of a plurality of light source modules LM. Accordingly, high-resolution detection can be achieved as in the high-density probes of JP-2014-083069-A, without increasing complicated operation.

Figure 28A:
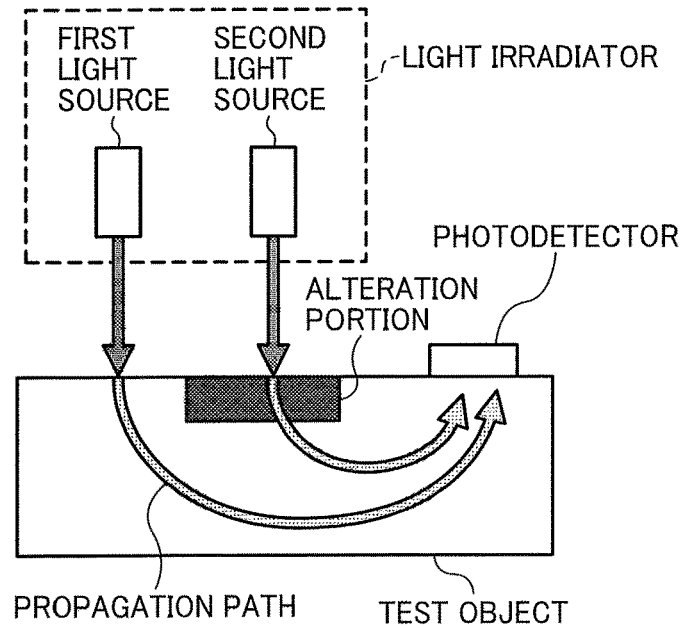
FIG. 28A is a diagram illustrating the operation of an optical sensor according to a control sample.

FIG. 28A is a diagram illustrating the operation of an optical sensor according to a control sample.

In the light source module according to a control sample as illustrated in FIG. 28A where a plurality of light rays that are parallel to each other enter a live subject, an error occurs in the detection when an alteration portion is present near the surface of the live subject. The term "alteration portion" indicates a portion with special optical properties, and includes, for example, roots of a hair and a colored skin. When such an alteration portion is present in the present control sample, the light rays emitted from the first light source and the second light source, respectively, enter different positions of the test object. For this reason, there may be some cases in which, for example, only the light emitted from the second light source passes through the alteration portion. When the difference between the first light source and the second light source is calculated, such an alteration portion may cause a noise.

Figure 28B:
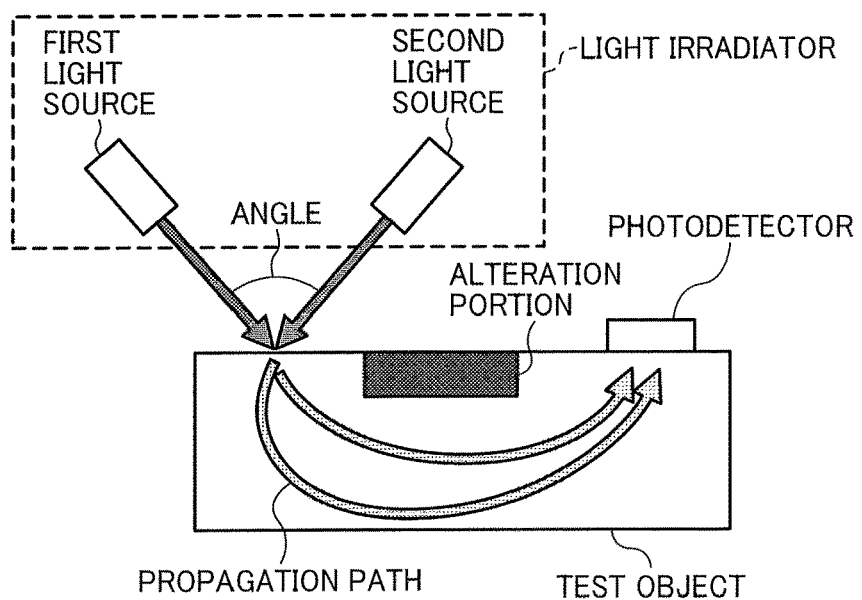
FIG. 28B is a diagram illustrating the operation of an optical sensor according to the first embodiment of the present invention.

FIG. 28B is a diagram illustrating the operation of an optical sensor according to the first embodiment of the present invention.

By contrast, in the present embodiment, as illustrated in FIG. 28B, the light rays emitted from the first light source and the second light source, respectively, pass through an "approximately identical point" of the surface of the skin. Accordingly, when one of the light rays emitted from the first light source and the second light source, respectively, pass through the alteration portion, the other one of the light rays also passes through the alteration portion. In a similar manner, when one of the light rays emitted from the first light source and the second light source, respectively, does not pass through the alteration portion, the other one of the light rays also does not pass through the alteration portion. More specifically, the light rays emitted from the first light source and the second light source, respectively, pass through the same optical path near the surface of the skin, and pass through different optical paths in a deeper portion. In other words, the configuration is insensitive to a difference near the surface of the skin, but is sensitive to a difference near the brain tissue. The resolution improves by reducing the noise near the surface of the skin. As described above, the term "approximately identical point" allows a displacement of about several millimeters.

In the second variation, a transparent gel is dripped onto the window member provided for the housing such that the transparent gel intervenes between the window member and the surface of the test object and the air is removed.

In the conventional light source module, the light that is once radiated in the air enters the surface of the skin and propagates inside the body. In such a configuration, a difference in refractive index arises between the refractive index 1.0 of the air and the refractive index 1.37 of a live subject. As such a difference in refractive index arises, reflection and scattering occur. Moreover, the refractive index inside the live subject in which the light propagates is smaller than that of the air outside the live subject. For this reason, the propagation angle inside the live subject becomes smaller than the incident angle. The refraction of light on the interface can be understood from the Snell laws of reflection. The Snell law (the law of reflection) can be described by refractive indexes only.

Figure 29:
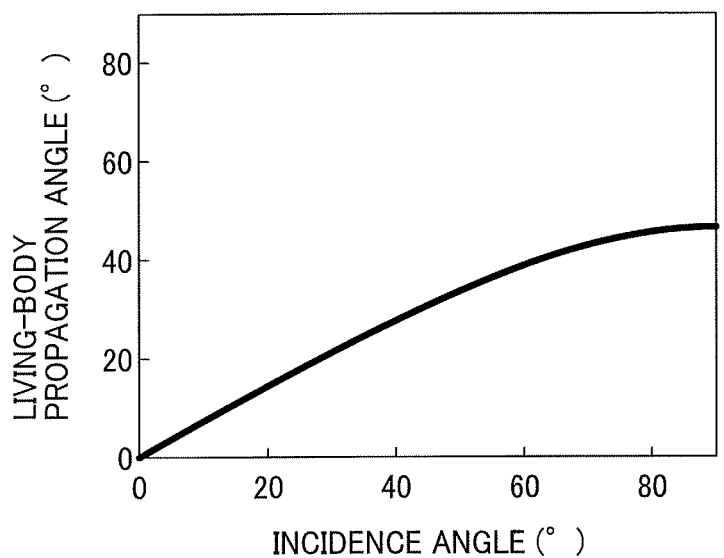
FIG. 29 is a graph illustrating the relation between the propagation angle inside the live subject and the incident angle that a light forms with the surface of a live subject when the light in the air enters the live subject.

FIG. 29 is a graph illustrating the relation between the propagation angle inside the live subject and the incident angle that a light forms with the surface of a live subject when the light in the air enters the live subject.

More specifically, the relation (refraction of light) between the propagation angle inside the live subject and the incident angle on the interface between the air on the on the light entering side (refractive index 1.0) and the live subject on the propagation side (refractive index 1.37) is depicted by the graph in FIG. 29. As understood from FIG. 29, even when the incident angle of the light that enters the live subject is 60 degrees, the propagation angle of the light that has entered the live subject is reduced to 40 degrees. Accordingly, even if a desired propagation angle of the light that has entered the live subject is equal to or greater than 60 degrees, such a propagation angle cannot be achieved by the incident light from the air. In other words, it is difficult to form a propagation angle of large degree inside the live subject from the light that has once released into the air.

Figure 30:
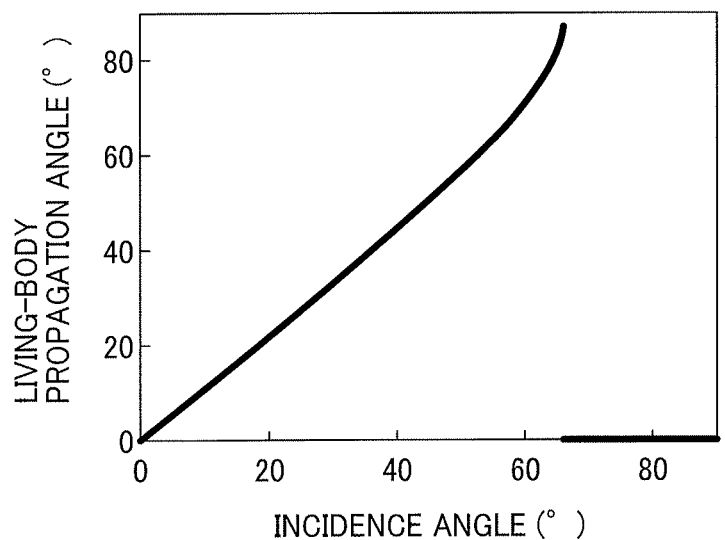
FIG. 30 is a graph illustrating the relation between the propagation angle inside the live subject and the incident angle, which a light forms with the surface of a live subject when the light in the resin enters the live subject, according to the second variation of the first embodiment.

FIG. 30 is a graph illustrating the relation between the propagation angle inside the live subject and the incident angle, which a light forms with the surface of a live subject when the light in the resin enters the live subject, according to the second variation of the first embodiment.

In order to handle such a situation, in the second variation, the refractive index of the transparent resin that makes up the window member of the light source module LM is designed to be greater than the refractive index 1.37 of the live subject (for example, equal to or greater than 1.5) (see FIG. 30). In this configuration, when the light is emitted from the light source module LM with the incident angle of 60 degrees, the propagation angle of the light that directly enters the live subject exceeds 70 degrees inside the live subject. When the angle is smaller in the design, the light source module LM can be downsized.

In the light source module LM (type I) according to the second variation, as illustrated in FIG. 16, the light that is emitted from the surface-emitting laser element in the direction parallel to the optical axis of the lens is refracted by the lens, and travels in a direction inclined by about 20 degrees with reference to the optical axis of the lens and enters the window member. The window member is designed to have the refractive index of about 1.5. The light that has passed through the lens is refracted when it enters the window member. However, such refraction is not large as the incident angle is not acute. The light that has entered the window member is deflected by the reflection plane of the prism, and travels in a direction inclined by about 55 degrees with reference to the optical axis of the lens. This angle of 55 degrees is the angle inside the window member of the refractive index 1.5, and as illustrated in FIG. 30, the propagation angle inside the live subject (of the refractive index 1.37) is about 60 degrees.

In order for the light emitted from the light source module LM to propagate inside a pseudo live subject in a direct manner, it is necessary to remove the airspace that exists in the interface between the pseudo live subject and the light source module LM. In the present embodiment, transparent gel is used to remove such airspace. The transparent gel used here is an aqueous glycerin solution that goes well with a pseudo live subject. The volatility of the transparent gel is controlled so as not to evaporate during the inspection while the light source module LM is closed by a lid, and the volatility of the transparent gel is controlled so as to evaporate or soak into the pseudo live subject at an appropriate timing after the inspection is done. The optical properties of the transparent gel are controlled to become transparent near a wavelength of 780 nm, and the refractive index is adjusted to be close to that of the surface of pseudo live subject. In the present example, the refractive index is adjusted to be about 1.37. Due to this adjustment, the difference in refractive index on the bumps and dips of the surface of the pseudo live subject can be attenuated, and a state of no reflection can be achieved. Accordingly, the reflection on the surface of the pseudo live subject can be almost eliminated.

There are physical bumps and dips on interface with the pseudo live subject, but there are no optical bumps and dips. Accordingly, no scattering occurs. As a result, the light emitted from the light source module LM can precisely be propagated inside the pseudo live subject in an appropriate propagation direction according to the exit angle. As known in the art, the propagation inside the pseudo live subject causes scattering strongly. However, the scattering on the surface of the skin is not small. According to the configuration as described above, the anisotropy of the light can be secured to a large degree. As the anisotropy can be secured to a large degree, the incident angles of the multiple light rays emitted from the light source module LM on the pseudo live subject can be varied widely, and as will be described later, the incident angles at which the multiple light rays enter the detection module DM can be varied widely.

Figure 31:
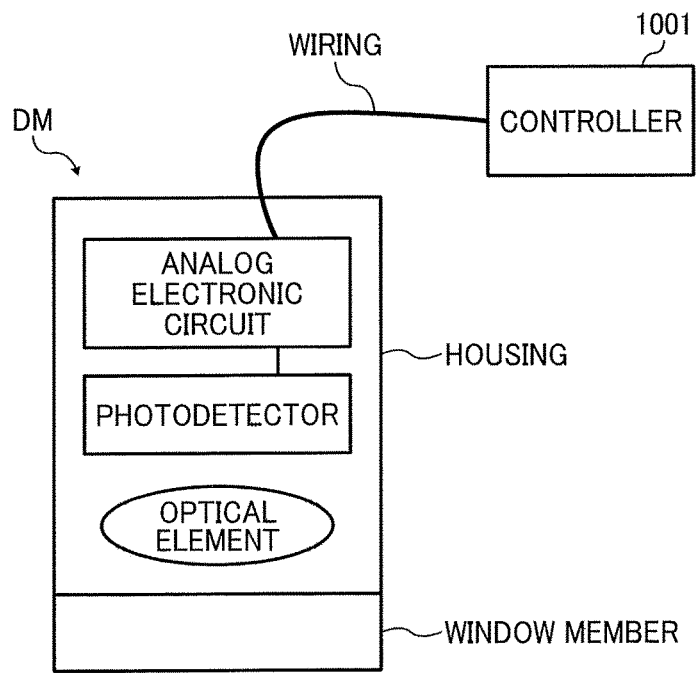
FIG. 31 is a first diagram illustrating a general configuration of a detection module according to the second variation of the first embodiment.

FIG. 31 is a first diagram illustrating a general configuration of the detection module DM according to the second variation of the first embodiment.

As illustrated in FIG. 31, the detection module DM includes the housing, an optical element, a flexible circuit board on which a photoreceptor and an analog electronic circuit are mounted, a wiring connected to the flexible circuit board, and a connector.

Figure 32:
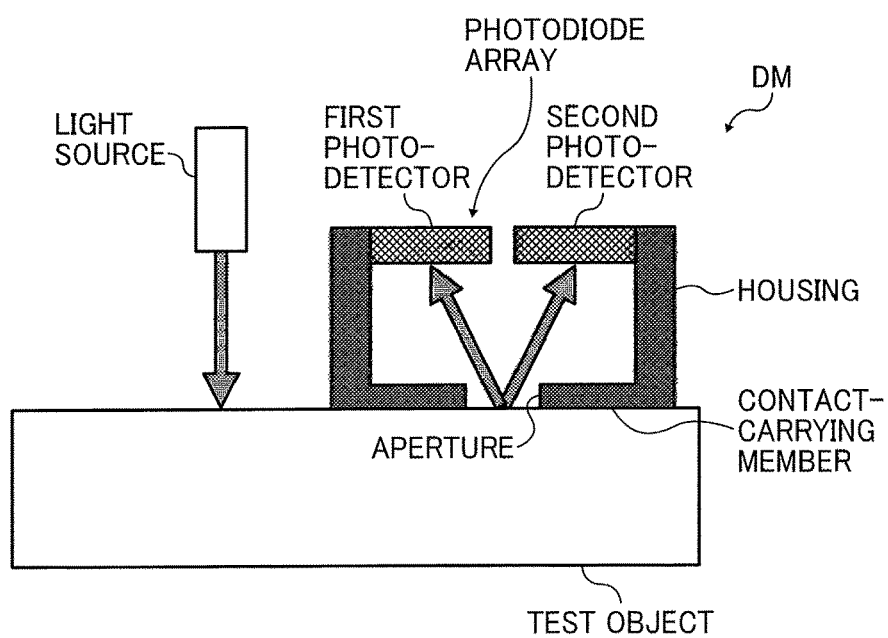
FIG. 32 is a second diagram illustrating a general configuration of a detection module according to the second variation of the first embodiment.

FIG. 32 is a second diagram illustrating a general configuration of the detection module DM according to the second variation of the first embodiment.

As illustrated in FIG. 32, in the detection module DM, the light that is emitted from the light source to the test object propagates inside the test object, and the light is split into a plurality of light rays and are guided to a plurality of photoreceptors.

In the related art (see, for example, JP-2011-179903-A), in DOT making use of fluorescence, a photoreceptor is arranged in accordance with a plurality of light rays emitted from a test object with varying angles. However, in this arrangement of a photoreceptor, the light of all the exit angles from the test object enters the photoreceptor.

By contrast, the detection module DM according to the present embodiment separately detects the split light rays that have entered the test object at an "approximately identical point". As described above in regard to the light source module LM, the detection module DM can be designed when an optical simulation is performed. For this reason, a difference in position in the order of millimeter is no object in the precision of the "approximately identical point".

Figure 33:
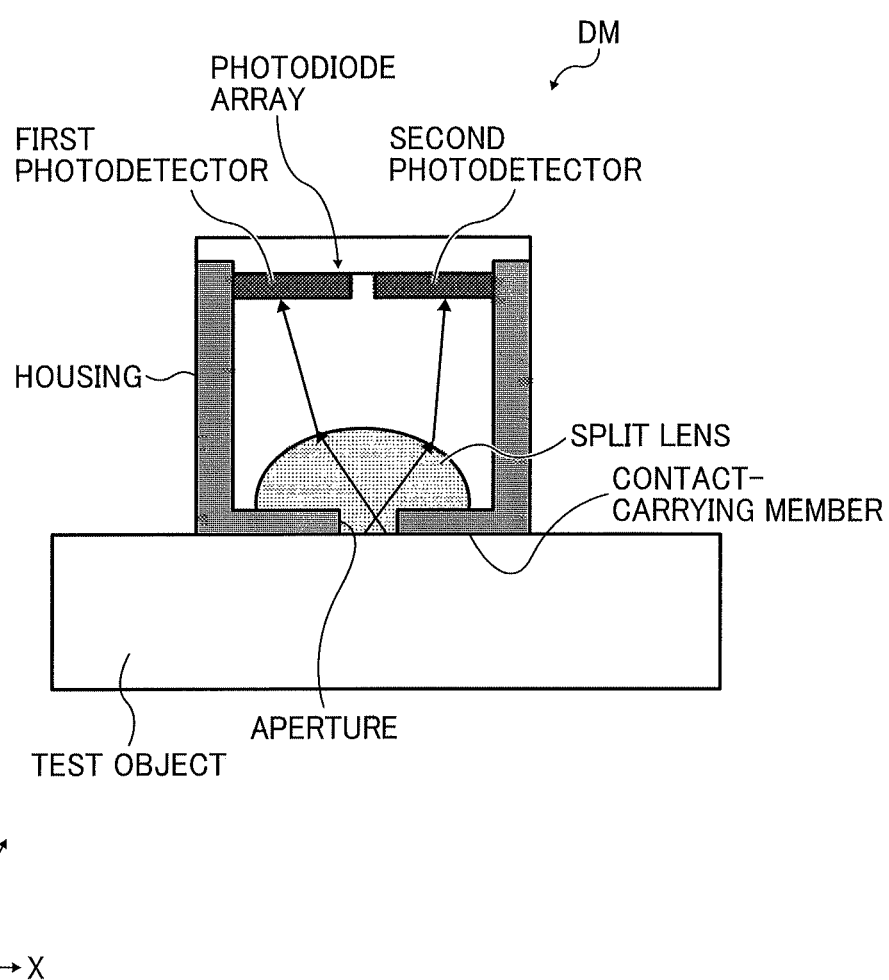
FIG. 33 is a third diagram illustrating a general configuration of a detection module according to the second variation of the first embodiment.

Next, the detection module DM is described in detail. As illustrated in FIG. 33, the detection module DM includes a black-resin housing, a contact-carrying member consisting of an elastic body attached to a front end of the housing, a transparent split lens accommodated in the housing, and four photoreceptors. The housing has apertures at the front end of the housing and at the other end of the housing in contact with the contact-carrying member.

In the present embodiment, black rubber is used for the contact-carrying member in order to enhance the imperviousness to light. From the aperture of the contact-carrying member, a center portion (about $\varphi 1$ mm) of the split lens stick out by about several hundreds of micrometers to the outside of the housing. As this portion contacts the surface of the live subject, no air optically exists therein. Accordingly, refraction of Fresnel or scattering is prevented.

The stability of the detection module DM also further improves when the above-described transparent gel is used. Accordingly, the transparent gel is used for the detection module DM. The split lens is composed of a transparent resin, and its refractive index is about 1.8. The split lens is attached to the housing.

The aperture is a circular hole with the size of about 1 mm that penetrates the leading end and the contact-carrying member of the housing, and serves to limit the position of the light that propagates inside the test object and exits from the test object. The light rays that exit from the aperture are oriented to a plurality of different directions. The incident positions are determined by the aperture, and then the incident light is split into a plurality of light rays by the split lens. Accordingly, these multiple light rays can separately be detected.

Note that this aperture enables the light rays exiting from the test object as above to enter the photoreceptor from an "approximately identical point".

The light rays that have passed through the aperture are refracted into different directions by the split lens according to the propagation directions of these light rays. Accordingly, the positions at which the light rays enter the photoreceptor are different from each other.

The split lens is a spherical lens, and has an about 3 mm diameter and an about 3 mm focal length f.

In the second variation, the number of the partitions of the light by the split lens is four, and a photodiode array having four two-dimensionally arranged photoreceptors (photodiodes) is used. Note that in FIG. 33, only two of the four photoreceptors (photodiodes), i.e., the first photoreceptor and the second photoreceptor, are illustrated.

In the present example, the photodiode array has a square shape where the sides have about 3 mm length, and each of the photodiodes has a square shape where the sides have 1.4 mm length. As illustrated in FIG. 33, an angle $\theta 2$ is defined, and the distance between the photodiode array and the aperture is about 5 mm.

One side of the lens is planar, and the other side of the lens is spherical. The planar side contacts the pseudo live subject. As the position of the aperture is displaced from the focal point of the lens, the lens cannot form parallel light rays. The lens is used to limit the light that enters the photodiode array.

A simplified optical simulation is performed on this optical system, and the following result is obtained. The light with approximately $-10°<\theta 2<50°$ enters the second photoreceptor, and the light with approximately $-50°<\theta 2<10°$ enters the first photoreceptor. In other words, the light that has propagated inside the pseudo live subject and exited from the aperture is split into a plurality of light rays according to the exit angles, and each of these multiple light rays enters one of the four photoreceptors.

In the second variation of the first embodiment, a spherical lens is used for the split lens. However, an aspherical lens may be used for the split lens to widen the angle of detection. The split accuracy and the number of partitions correlates with the estimation accuracy of an inverse problem as will be described later. For this reason, an optical system is determined by a desired level of estimation accuracy. In the present embodiment, a spherical lens is adopted and the number of partitions is four.

The photodiodes are electrically wired, and are connected to an operational amplifier. A semiconductor operational amplifier is used for the operational amplifier, and the operational amplifier supplies source voltage of 5 volts. As the detectable amount of light is very small, the amplification factor of the operational amplifier is high, and two-stage amplification is adopted. The amplification factor of about five digits is applied in the first stage, and the amplification factor of about three digits is applied in the second stage.

Figure 34:
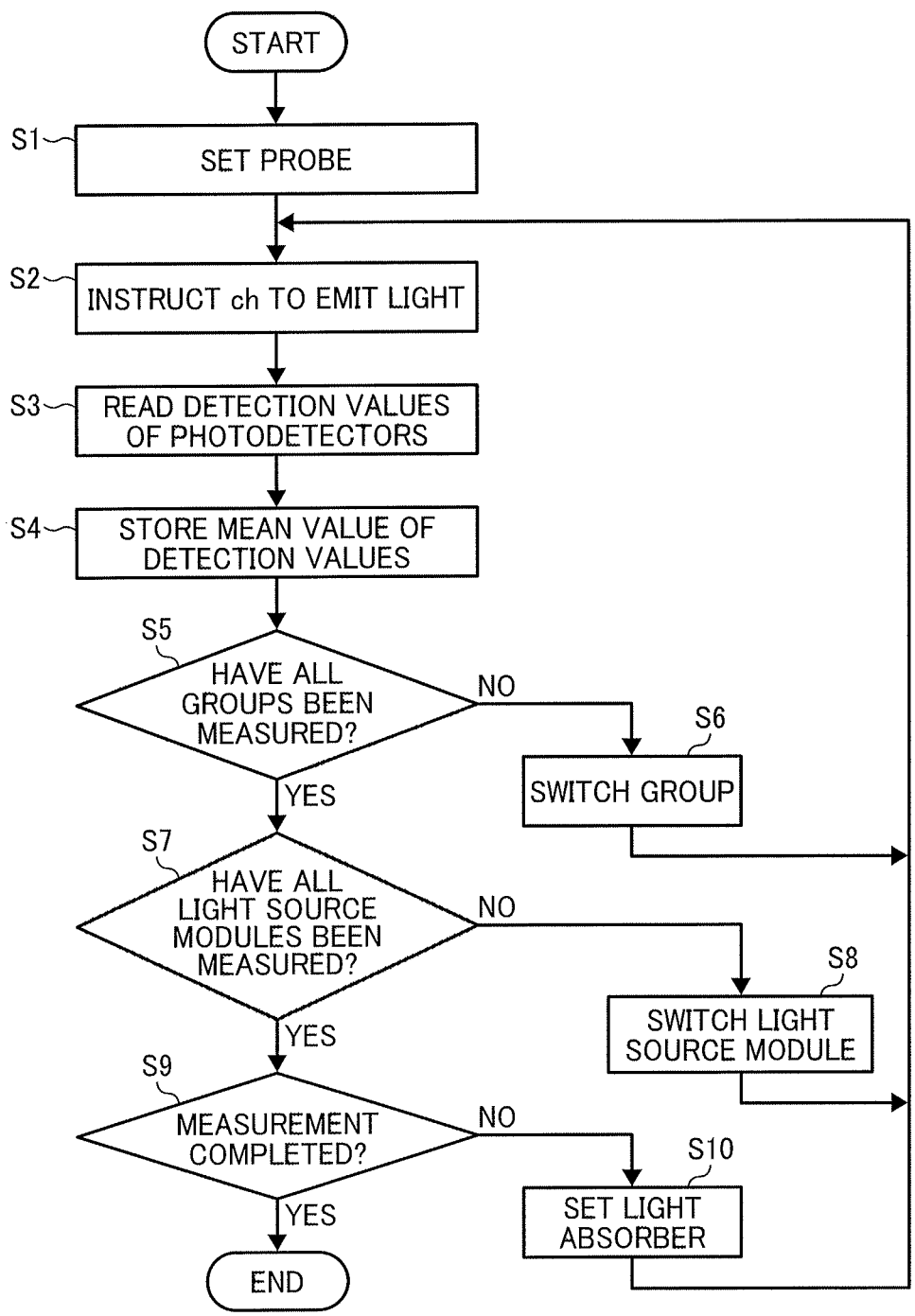
FIG. 34 is a flowchart of a method of detecting optical properties (position measuring method) according to the second variation of the first embodiment.

FIG. 34 is a flowchart of a method of measuring the position of the light absorber in the pseudo live subject (method of detecting optical properties of the test object) according to the second variation of the first embodiment.

Firstly, the probes (i.e., the light source modules LM and the detection modules DM) are set (inserted) into the pseudo live subject (step S1). In so doing, a transparent gel is applied to between the acrylic watertank and each of the probes, and each of the probes is carefully set to a position determined by a fixation member so as not to mix bubbles into the transparent gel.

The number of the probes is sixteen including eight light source modules LM and eight detection modules DM, and the light source modules LM and the detection modules DM are alternately arranged in a grid pattern with equal pitches (see FIG. 15). The pitch in the grid pattern (space among points of the grid pattern) is 30 mm, and the space between each of the light source modules LM and detection modules DM is 30 mm.

In this state, a desired one of the channels of the light source module LM is instructed to emit light (step S2). The light source module LM is instructed to emit light on a group-by-group (four channels) basis, and the light-emission intensity is determined such that the current value becomes about 4 mW. The light emitting period is about 10 msec, and the detection values of all the photodiodes are read during the light emitting period, and the data (detection values) obtained at 1 msec intervals are averaged (step S3). Then, the averaged detection values is stored in the memory (step S4). In a similar manner, the 10 msec light emission, the measurement, and the data storage are repeated for the next group (steps S5, S6, and S2 to S4). Note that in each one of the light source modules LM, in a similar manner, the light emission of the four channels of the surface-emitting laser array chip of the oscillation wavelength of 780 nm and the light emission of the four channels of the surface-emitting laser array chip of the oscillation wavelength of 900 nm are performed in sequence.

However, in the data processing described below, the two wavelengths are treated in almost the same way. Accordingly, in the present embodiment, the measurement performed with two varying wavelengths is equivalent to the repeated measurement at the same position. When the changes in the real bloodstream are detected, the difference between the two wavelengths is used for the detection of oxyhemoglobin and reduced hemoglobin in a separate manner. However, in the present embodiment, measurement is performed one time using two surface-emitting laser array chips with varying oscillation wavelengths. Accordingly, the noise due to the variations in chips can be reduced.

After the light emission and measurement of all the groups of one of the light source modules LM are completed, the light emission of the next light source module LM is performed (steps S7, S8, and S2 to S6). In a similar manner to the above, the light source module LM is instructed to emit light sequentially on a group-by-group (4ch) basis. After the light emitting and measurement of all the light source modules LM are completed, a light absorber is set (steps S9 and S10). In order to set the light absorber at a desired position precisely with high reproducibility, an optical stage is used. After the light absorber is set as described above, the steps from the light emission of the channels to the storage of the detection values of the photodiodes are performed again (steps S2 to S9).

The stored data is labeled as $r(s,i,n)$ ($i=1, 2, 3, \ldots M; n=1, 2, 3, \ldots K$) with the light absorber and $r(0,i,n)$ ($i=1, 2, 3, \ldots, M; n=1, 2, 3, \ldots, K$) without the light absorber. "i" denotes the numbers assigned to the respective detection modules DM. "n" denotes the numbers assigned to the respective groups. Next, the difference $\Delta r(i,n)$ of the respective groups is calculated.

The method of calculating the position of the light absorber (the optical properties of the pseudo live subject) according to the result of the measurement obtained by the measurement method as described above is similar to the method of calculating the position of the light absorber (the optical properties of the pseudo live subject) according to the result of the measurement obtained by the measurement method as described above with reference to the flowchart of FIG. 8, and thus its description is omitted.

Figures 35, 36:
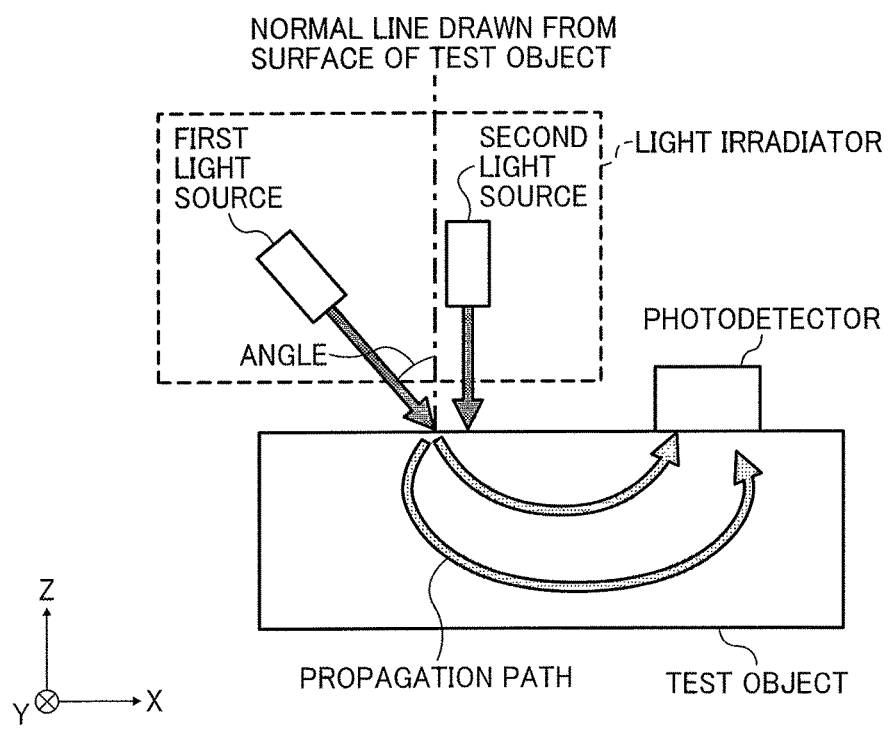
FIG. 35 is a diagram depicting the result of an inverse problem estimation according to the second variation of the first embodiment.
FIG. 36 is a diagram illustrating the operation of an optical sensor according to the first embodiment of the present invention.

As a result, the result of estimation as illustrated in FIG. 35 can be derived. FIG. 35 also depicts, as a control sample, the results of the detection in which only the center one of the five groups of the surface-emitting laser array chip (see FIG. 17) is controlled to emit light and the detection value of only one of the four photodiodes of the photodiode array is used. In the other respects, the numeric values are all processed in the same way as the present embodiment. The configuration of this control sample is almost equivalent to that of the conventional NIRS DOT device.

By contrast, in the present embodiment, the Bayes estimation is adopted as described above, and both the position and depth of the light absorber are detectable. In the results depicted in FIG. 35, a circular sign is given for a case where the position of the light absorber is successfully detected. In the present embodiment, as the distance in the depth direction of the light absorber (i.e., the Z-axis direction in FIG. 10) becomes longer, the distance to the light source module LM becomes longer, and the amount of light that can propagate decreases. For this reason, as the depth of the position of the light absorber becomes deeper, it becomes more difficult to perform detection successfully. In the present embodiment, detection was successful up to the depth of about 6 mm. In the control sample, a known NIRS DOT device is used, and the detection in the depth direction was not successfully performed even with the application of the Bayes estimation. In order for DOT to detect the three-dimensional position including the depth of the light absorber with high accuracy, the layout of probes with high density is required as known in the art. However, in the present embodiment, with the layout of probes with low density, the three-dimensional position of the light absorber was successfully detected with high accuracy.

As described above, the optical, sensor 10 according to the present embodiment (the first and second variations) includes an irradiation system including a plurality of light source modules LM (light irradiators) to irradiate a test object (pseudo live subject) with light, and a detection system that detects the light that is emitted from the irradiation system and propagated inside the test object. Then, each of the multiple light source modules LM emits multiple laser-beam bundles that are not parallel to each other to an approximately identical point of the test object.

In the above configuration, as illustrated in FIG. 36, the multiple laser-beam bundles that are not parallel to each other, which are emitted to an approximately identical point of the test object (scatterer), have different incident angles with reference to the test object, and take varying propagation paths.

Accordingly, the amount of information obtained for the inside of the test object increases; and higher resolution can be achieved. Moreover, as the resolution is improved, the density of the probes (i.e., the number of probes for each unit of dimension) can be reduced for the same desired resolution. Accordingly, attachability improves.

Accordingly, the optical sensor 10 can achieve higher resolution without degrading the attachability to the test object.

Note that the multiple laser-beam bundles that are not parallel to each other but enter an approximately identical point of the test object indicates that the multiple bundles of light rays form angles with each other. In other words, as there exist angles formed by the multiple bundles of light rays, the propagation paths of the multiple bundles of light rays in the test object can be varied. By contrast, if the multiple laser-beam bundles that enter an approximately identical point of the test object are parallel to each other (for example, if the multiple laser-beam bundles are parallel to the normal line to the surface of the test object), the propagation paths of the multiple laser-beam bundles in the test object become the same.

The light source module LM according to the present embodiment includes a surface emitting laser array having a plurality of surface emitting lasers (light-emitting units), and a convex lens disposed in the optical path of a plurality of light rays emitted from the surface emitting lasers to form a plurality of light rays that are not parallel to each other. The distance between the surface emitting laser array and the principal point of the convex lens does not match the focal length of the convex lens.

Accordingly, the return light can be prevented from concentrating on the surface emitting laser, and the fluctuations in the output of the surface emitting laser can be prevented. As a result, the amount of light emission of the surface emitting laser can be stabilized, and the accuracy of detection of the optical sensor 10 improves. Further, the resolution of the NIRS can be improved.

By contrast, if the surface emitting laser array is at the focal point of the convex lens, the light reflected from an external reflection plane is concentrated onto the surface emitting laser by the convex lens, and the laser oscillation becomes unstable. This phenomenon is called, for example, return light or self-mixing. If this phenomenon occurs when a surface emitting laser array is used as the light source of an optical sensor, the amount of light emission becomes unstable. See JP-2011-114228-A and JP-2012-132740-A for the detail.

The space between the convex lens and the surface emitting laser array is filled with a transparent resin whose refractive index is equivalent to that of the convex lens.

As a result, the refractive index does not change at the boundary of the interface between the convex lens and the surface emitting laser array, and the return light can be prevented. As a result, the amount of light emission of the surface emitting laser array can be stabilized, and further, the resolution of the NIRS can be improved.

The detection system includes a plurality of detection modules DM each of which includes a plurality of photoreceptors (photodiodes) configured to receive the multiple light rays separately that are emitted from the light source module LM to the test object and have propagated inside the test object.

In this configuration, the two items of data of two different propagation paths inside the test object can separately be obtained.

The detection module DM has the housing and the contact-carrying member disposed between the test object and a plurality of photoreceptors (photodiodes), and an aperture is formed on the contact-carrying member. Moreover, some of each of the multiple light rays that have propagated through the test object passes through the aperture.

In this configuration, the light can be taken into the housing from an approximately identical point of the test object. More specifically, only light rays with limited incident angles enter the housing. Accordingly, each of a plurality of photoreceptors can receive light easily.

Moreover, the detection module DM includes the split lens (light-receptive lens) that separately guides some of the multiple light rays passed through the aperture to the multiple photoreceptors.

In this configuration, some of each of the multiple light rays passed through the aperture can separately enter the multiple photoreceptors with a stable amount of light.

The light source module LM includes a window member that contacts the test object and is composed of a material (transparent resin) whose refractive index is greater than that of the test object. Accordingly, the propagation angle (refraction angle) of the light inside the test object can be increased with reference to the incident angle on the test object. As a result, compared with cases in which, for example, the light in the air enters the test object, the propagation angle can be increased even with the same degree of incident angle. Accordingly, the difference in propagation angle between the two light rays inside the test object increases than the difference in incident angle between the two light rays that enter an approximately identical point of the test object with varying incident angles, and the propagation paths of the multiple light rays in the test object can be varied significantly. As a result, an even higher resolution can be achieved.

The light source module LM includes a plurality of two-dimensionally disposed surface emitting lasers and an irradiation lens (lens) disposed in the optical path of a plurality of light rays emitted from the multiple surface emitting lasers.

In this configuration, the directions of travel of the light rays emitted from the multiple surface emitting lasers can be changed to desired directions (i.e., the directions towards the positions at which the corresponding prisms are disposed).

Moreover, the light source module LM includes a prism (reflection member) disposed in the optical path of the light that has passed through the irradiation lens, and the prism reflect the light towards a prescribed direction.

In this configuration, the direction of travel of the light emitted through the irradiation lens can further be changed to a desired direction. In other words, the incident angle on the test object can be designed to a desired angle.

As described above, the optical sensor 10 is an optical sensor with a relatively simple configuration that effectively utilizes the anisotropy of the propagation of light to achieve high resolution. For example, such an optical sensor may be applied to various kinds of fields such as the field of DOT.

The optical examination device 100 includes the optical sensor 10, and a controller (optical property calculator) 1001 that calculates the optical properties of the test object based on the detection results of the optical sensor 10.

In this configuration, the accuracy of the detection at the optical sensor 10 is high, and thus the optical property of the test object can be calculated with high accuracy.

The optical sensor 10 according to the present embodiment (the first and second variations) includes an irradiation system including a plurality of light source modules LM (light irradiators) to irradiate a test object (for example, a live subject) with light, and a detection system that detects the light that is emitted from the irradiation system and propagated inside the test object. Each of the multiple light source modules LM can emit multiple light rays with different wavelengths to an approximately identical point of the test object.

In this configuration, the internal information of the test object can precisely be obtained.

More specifically, the position of the cerebral blood flow can be measured with high precision in a near-infrared spectroscopy (NIRS) device that performs an inverse problem estimation.

The light source module LM (type III) includes two channels (whose wavelengths in exiting light are different from each other) that separately emit two light rays with different wavelengths, the first and second lenses that are separately disposed in the optical paths of the two light rays with different wavelengths that are emitted from the two channels described above, and a prism for common use that is disposed in the optical paths of the two light rays with different wavelengths that have passed through the two lenses described above. Then, the optical paths of the two light rays with different wavelengths that are reflected on the prism approximately overlap one another. Note that the expression "optical paths approximately overlap one another" indicates that the angle which the optical paths of a desired pair of light rays forms is equal to or less than 10 degrees, where such a desired pair of light rays are chosen from a plurality of light rays with different wavelengths that are reflected on a prism.

As described above, with a relatively simple configuration, two light rays with different wavelengths can irradiate an identical point of the test object.

In the light source module LM (type III), a prism includes reflection planes (total reflection planes R1 and R2) that reflect two light rays with different wavelengths that have passed through the first and second lenses, and the optical paths of the two light rays with different wavelengths from the first and second lenses to the reflection planes are not parallel to each other.

As described above, the configuration can be simplified and the cost can be reduced compared with cases in which two light rays with different wavelengths are separately reflected on two reflection planes.

In the light source module LM (type III), the number of optical components and the cost of installation can be reduced compared with cases in which a plurality of optical elements are used instead of the prism.

In the light source module LM (type III), the optical paths of the two light rays with different wavelengths from the first and second lenses to the reflection planes of the prism get close to each other as the light rays get close to the reflection planes of the prism. For this reason, these two light rays can be reflected on the reflection planes towards a test object in a state where the optical paths of these light rays are made close to each other.

In the light source module LM (type III), the two light rays with different wavelengths that are reflected on the reflection planes of the prism intersect near the exit end of the light source module LM (type III). Accordingly, these two light rays can enter an identical point of the test object with reliability.

In the light source module LM (type III), each of the two channels includes a plurality of light-emitting units that are arranged in an array, and the relative positions of these multiple light-emitting units and the optical axis of the corresponding one of the lenses differ among a plurality of light sources. Accordingly, the two light rays with different wavelengths that are emitted from two light-emitting units that correspond to each other between two channels can be emitted from the first and second lenses in a state where the two light rays are not parallel to each other.

In the light source module LM (type III), the center of each of the channels (center of array) is shifted from the optical axis of the corresponding one of the lenses. Accordingly, when it is assumed that two light-emitting units that correspond to each other between two channels is a pair, the relative positions of all the pairs of light-emitting units and the optical axes of the lenses can be varied.

The space between the first and second lenses and the corresponding two channels may be filled with a transparent resin whose refractive index is equivalent to that of the first and second lenses (see FIG. 23).

The first and second lenses may have a convex shape on the sides of the corresponding channels (see FIG. 25).

The optical element in common between the light source module LM (type II) and the light source module LM (type III) is not limited to a prism, but may be any member as long as it includes at least one reflection plane that can reflect a plurality of light rays with different wavelengths.

The optical sensor 10 according to the present embodiment (the first and second variations) includes an irradiation system including at least one light irradiator (light source module LM) to irradiate a test object with light, and a detection system that detects the light that is emitted from the irradiation system to the test object and propagated through the test object. The light irradiator includes a surface-emitting laser element that is a part of multilayered structure (multilayer chip) having an active layer, and a photo-sensing element that is another part of the multilayered structure and is optically connected to the surface-emitting laser element.

In this configuration, the light that escapes from the surface-emitting laser element can efficiently be propagated to the photo-sensing element, and the quantity of escaping light can be measured with a high degree of precision. Further, the output from the surface-emitting laser element can be controlled to a have a desired value.

As a result, the internal information of the test object can precisely be obtained.

The surface-emitting laser element and the photo-sensing element independently have mesa structure that includes an active layer. In other words, the two active layers are separate from each other. Due to this configuration, the quantity of light that escapes from the surface-emitting laser element can be measured with a high degree of precision with little loss in the output from the surface-emitting laser element.

The multilayered structure includes a lower spacer layer that integrally covers the bottoms of the mesa structure of the surface-emitting laser element and the photo-sensing element. Note that the bottoms of the mesa structure are adjacent to the active layer of the mesa structure of the surface-emitting laser element and the photo-sensing element.

In this configuration, the surface-emitting laser element and the photo-sensing element may optically be connected to each other at least via the lower spacer layer.

The multilayered structure may further include a transparent insulator film disposed above the lower spacer layer. In this configuration, the surface-emitting laser element and the photo-sensing element may optically be connected to each other at least via the transparent insulator film.

It is desired that the transparent insulator film have a refractive index smaller than that of the lower spacer layer. In this configuration, the light that escapes from the surface-emitting laser element can be propagated to the photo-sensing element through an inner path of the multilayered structure. Accordingly, the escaping light can be well prevented from dispersing.

It is desired that the surface roughness of the transparent insulator film be equal to or less than one-tenths of the oscillation wavelength λ of the surface-emitting laser element. It is more desirable if the surface roughness of the transparent insulator film be equal to or less than one-fiftieth of the oscillation wavelength λ of the surface-emitting laser element, and it is even more desirable if the surface roughness of the transparent insulator film be equal to or less than one-hundredth of the oscillation wavelength λ of the surface-emitting laser element. Due to such a configuration, the light can be prevented from escaping from the surface of the transparent insulator film.

It is desired that the transparent insulator film be composed of silicon oxide or silicon nitride. Alternatively, the transparent insulator film may be composed of other oxide films or nitride films. The insulator film that is formed on the lower spacer layer is satisfactory as long as the insulator film is translucent. For example, the insulator film may be a transparent film.

It is desired that the optical thickness of a portion that optically connects between the surface-emitting laser element and the photo-sensing element be equivalent to the oscillation wavelength λ of the surface-emitting laser element. In this configuration, the light that escapes from the surface-emitting laser element can efficiently be propagated to the photo-sensing element.

It is desired that the mesa structure of the photo-sensing element have a slot thereon that is surrounded by an electrode. In this configuration, light from above (for example, reflection light from an optical element or scattered light from a test object) is taken in the photo-sensing element, and the quantity of light can be measured.

The mesa structure of the photo-sensing element may include a reflector on the other side of the spacer layers with respect to the active layer. In such a configuration, it is desired that θ1<θ2 where θ1 denotes the tilt angle of the side of the active layer and the spacer layer of the mesa structure of the photo-sensing element and θ2 denotes the tilt angle of the reflector. Due to this configuration, a larger amount of light from obliquely upward can be taken in the photo-sensing element.

It is desired that the light irradiator have a plurality of surface-emitting laser elements and that an identical point of the test object be irradiated with a plurality of light rays that are not parallel to each other.

Accordingly, the amount of information obtained for the inside of the test object increases as above, and higher resolution can be achieved. Moreover, as the resolution is improved, the density of the probes (i.e., the number of probes for each unit of dimension) can be reduced for the same desired resolution. Accordingly, attachability improves. Accordingly, the optical sensor 10 can achieve higher resolution without degrading the attachability to the test object.

It is desired that the light irradiator further include an optical system that is disposed between the multilayered structure and a test object. In this configuration, the light that is emitted from the surface-emitting laser element can be guided to the test object by such an optical system, and the return light from the optical system can be detected by the photo-sensing element. In other words, one optical system enables both irradiation of a test object and detection of a condition of contact between the test object and the light irradiator.

It is desired that the detection system include at least one photodetector incorporating a plurality of photoreceptors to detect a plurality of light rays emitted from the light irradiator and propagated through the test object.

It is desired that the photodetector have a contact-carrying member disposed between the test object and the multiple photoreceptors and that a transmissive portion (aperture) be formed on the contact carrying member. Note that in this configuration some of each of the multiple light rays that have propagated through the test object passes through the transmissive portion.

Due to the optical examination device including the optical sensor 10 and the controller 1001 that calculates the optical properties of the test, object based on the detection results of the optical sensor 10, the optical properties of the test object (for example, the relative positions of light absorbers) can be measured with a high degree of precision.

An optical property detection method includes a step of obtaining a detection light quantity distribution for each of the optical model that simulate a test object, by performing optical simulation where the optical sensor 10 is used, and a step of performing inverse problem estimation using a result of the optical simulation. Due to such an optical property detection method, the optical properties of the test object can be measured with a high degree of precision.

In the multilayer chip as described above according to the first embodiment, both the surface-emitting laser element and the photo-sensing element have mesa structure. However, at least one of the surface-emitting laser element and the photo-sensing element may have no mesa structure. Even in such a configuration, it is desired that the active layers of the surface-emitting laser element and the photo-sensing element be insulated.

In the multilayer chip as described above according to the first embodiment, a part of the side of an upper reflecting mirror may be selectively oxidized to form an oxidized narrow layer.

Note also that, for example, the layer structure, the number of surface-emitting laser elements or photo-sensing elements, and the arrangement in the multilayer chip according to the first embodiment as described above may be changed where appropriate.

<Second Embodiment>

Next, a second embodiment of the present invention is described. In the present embodiment, a method of adapting the probes described above in the first embodiment to an actual human body is described. In the present embodiment, the test object is changed from the phantom (the watertank filled with whitish water) to the human head, and the light absorber is changed to the bloodstream in the brain.

In the present embodiment, the distribution of the bloodstream inside the brain is to be estimated with high accuracy. As known in the art, in the present embodiment, a test subject (test object) is measured and the shape is modeled based on the obtained data, and then the Monte Carlo simulation is performed. Moreover, the magnetic resonance imaging (MRI) is used to measure the shape of the head of the test subject. More specifically, the shapes of the four sites of the head including the scalp, the skull, the cerebrospinal fluid, and the cerebral cortex are measured from the images.

Such three-dimensional data is required for high-precision detection. However, such three-dimensional data may be substituted, for example, by preparing a plurality of model brains (optical models) of standard shape and selecting one of these model brains appropriately. For each of the sites, a normal scattering coefficient, anisotropy, and absorption coefficient are known, and thus these known values are used. The probes are precisely attached to the head by fixtures, and the attached positions are also precisely measured. An optical simulation is performed using the accurate shapes and the layout of the elements and the values of the sites.

Also in the present embodiment, the Monte Carlo simulation is performed. Several sets of four light source modules LM and four detection modules DM are fixed on the forehead of a head via folders. It is assumed that each of the light source modules LM has five directions and each of the detection modules DM has four directions. The conditions of angles or the like are assumed to be the same as those of the first embodiment as described above. The optical simulation is to be calculated for all the propagation angles and detection angles of all the pairs of the light source modules LM and detection modules DM.

Figure 37:
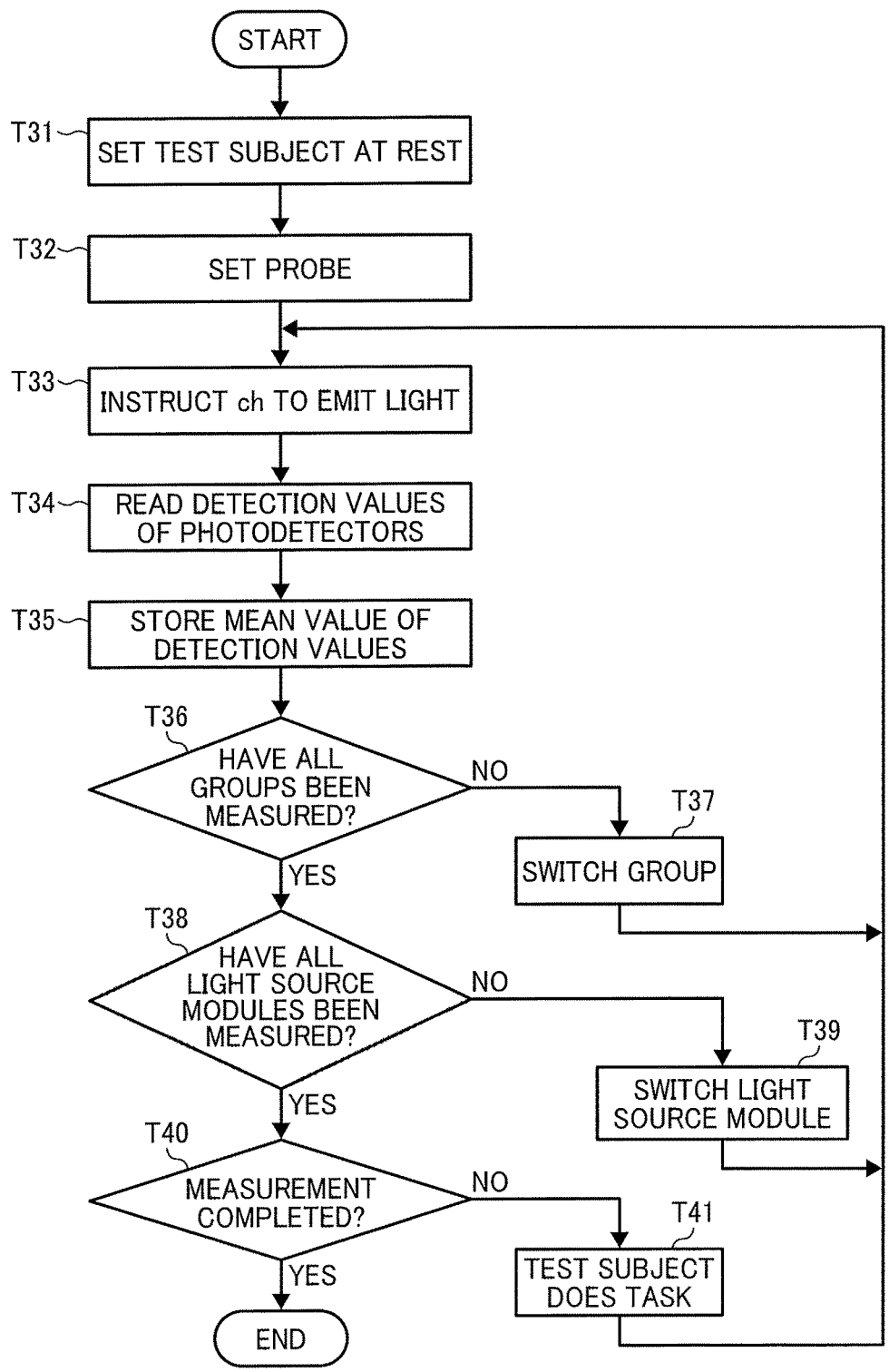
FIG. 37 is a flowchart of a method of detecting optical properties (position measuring method) according to a second embodiment of the present invention.

In the following description, a method of measuring the bloodstream inside the brain is described below with reference to the flowchart illustrated in FIG. 37. Firstly, the test subject is set at rest (step S31), and the probes (the detection module DM and the light source module LM) are set to the head (step S32). In so doing, each of the probes is carefully set (disposed) to a prescribed position using a fixation member so as not to clamp a hair or the like between the probe and the scalp. In this state, the channels of the light source module LM are instructed to emit light (step S33). The light source module LM is instructed to emit light (emit pulses of light) on a group-by-group basis, and the light-emission intensity is determined such that the current value becomes about 4 mW. The light emitting period is about several milliseconds, and the detection values of all the photodiodes are read and averaged during the light emitting period (step S34). Then, the averaged detection value is stored in the recording medium (step S35).

In a similar manner, the light emission of several milliseconds, the measurement, and the data storage are repeated for the next group (steps S36, S37, and S33 to S35). After the light emitting and measurement of all the light source modules LM are completed, the test subject is asked to do a task (steps S38 to S41). In the present embodiment, a commonly-used language fluency task is used. For a detailed description of such a language fluency task, see JP-2012-080975-A.

<Third Embodiment>

Next, a third embodiment of the present invention is described. In the third embodiment, the light source modules LM and detection modules DM that are equivalent to those of the first embodiment as described above are used for probes, and the layout of the probes is different from different from the other embodiments. Other than the layout of the probes, the configuration of the third embodiment is equivalent to that of the first embodiment as described above, and thus redundant description is omitted here.

In the second variation of the first embodiment as described above, as illustrated in FIG. 15, two detection modules DM and two light source modules LM are disposed such that each of them is at the vertices of a roughly-drawn square. However, in the above layout, the optical path between each of the light source modules LM and detection modules DM becomes long at a point indicated by "X" in FIG. 15. For this reason, there is some concern that the amount of light received by the detection module DM is insufficient and the accuracy of detection may deteriorate due to the increased noise at that point.

Figure 38:
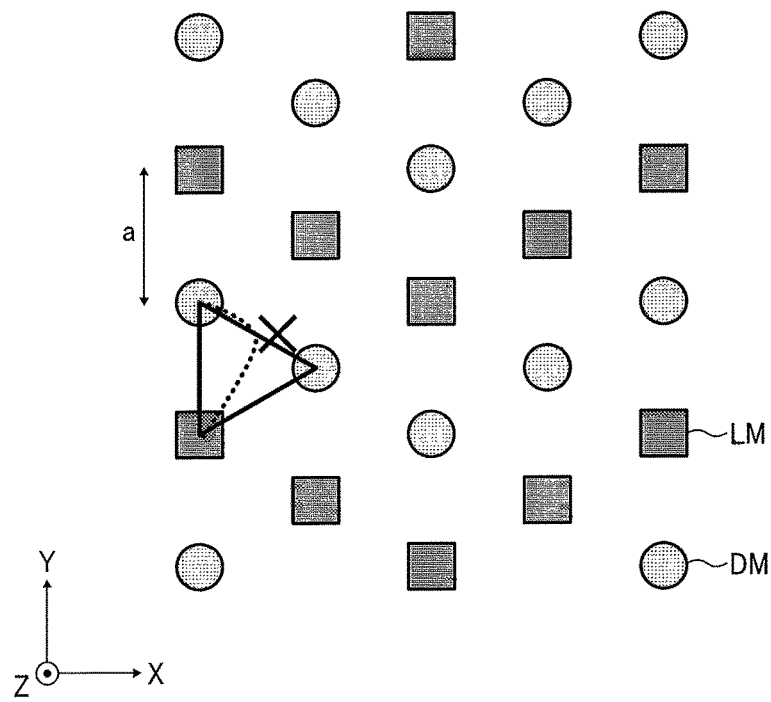
FIG. 38 is a diagram illustrating the arrangement of a plurality of light source modules and a plurality of detection modules in an optical sensor, according to a third embodiment of the present invention.

In order to handle such a situation, the layout of probes has been diligently studied, and it is found that the layout as illustrated in FIG. 38 is optimal. In FIG. 38, the multiple light source modules LM and detection modules DM are disposed for a test object such that two of either one of the light source modules LM and the detection modules DM are at two vertices of a regular triangle separately and one of the other one of the light source modules LM and the detection modules DM is at the remaining vertex of the regular triangle.

Here, for the purpose of simplification, the distances between the light source modules LM and the detection modules DM are compared with each other to find the longest distance. Note that it is assumed that the space (pitch) between each of the light source modules LM and detection modules DM is "a". At the position of "X" in FIG. 15, the distance indicated by the broken lines is $\sqrt{2}a$ (about 1.414a). By contrast, the position of "X" in FIG. 38, the distance indicated by the broken lines is $(1+\sqrt{3})/2$ (about 1.366a). In short, when the longest distances between the light source module LM and the detection module DM are compared with each other between the two layouts of the probes in FIG. 15 and FIG. 38, the layout of the probes illustrated in FIG. 38 is shorter and thus is more desirable.

An inverse problem estimation was performed in the layout of the probes of FIG. 38 in a similar manner to the first embodiment, and as a result, it was found that the detectable area is widened in the layout of the probes according to the present embodiment.

<Fourth Embodiment>

Next, a fourth embodiment of the present invention is described. In the fourth embodiment, the layout of the multiple light source modules LM and multiple detection modules DM equivalent to that of the first embodiment as described above is adopted, and the layout of the channels of the light source module LM and the layout of the photodiodes of the detection module DM are different from those of the other embodiments. Other than the layout of the channels and the photodiodes, the configuration of the third embodiment is equivalent to that of the first embodiment as described above, and thus redundant description is omitted here.

In the second variation of the first embodiment, as illustrated in FIG. 15, the multiple light source modules LM and detection modules DM are arranged for the test object so as to be next to each other in both the X direction and the Y direction that are orthogonal to each other.

However, as described above, in the above layout, the optical path between each of the light source modules LM and detection modules DM becomes long at the point indicated by "X". For this reason, there is some concern that the amount of light received by the detection module DM is insufficient and the accuracy of detection may deteriorate due to the increased noise at that point.

Figure 39:
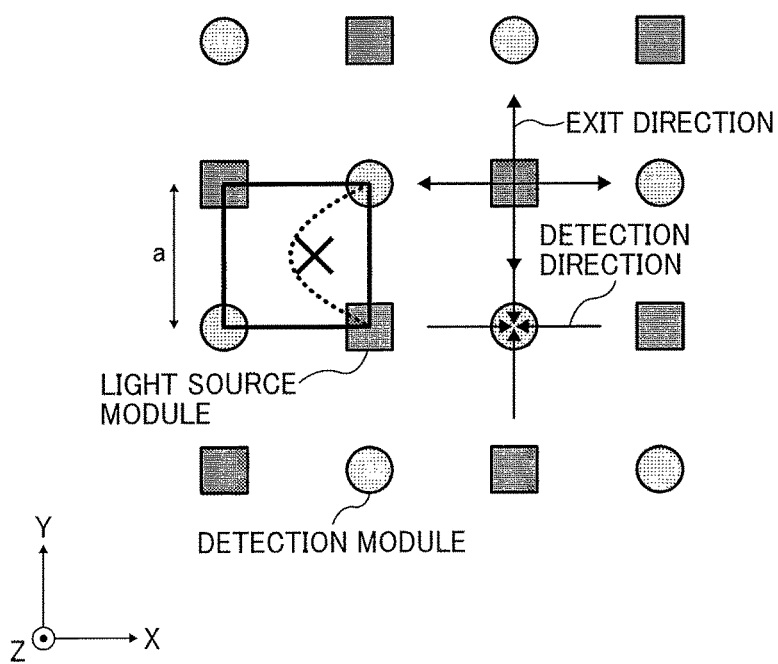
FIG. 39 is a diagram illustrating the exit directions of a plurality of light source modules and the detection directions of a plurality of detection modules in an optical sensor, according to a control sample.

In the control sample illustrated in FIG. 39, the multiple light source module and the multiple detection module are arranged for the test object so as to be next to each other in both the X direction and the Y direction that are orthogonal to each other, and both the exit directions and the detection directions (i.e., the direction at which the light enters the photoreceptor) are parallel to the X direction and the Y direction. The lens that is disposed near the surface emitting laser has optical properties of point symmetry. Accordingly, the exit directions depend on the position of the surface emitting laser and the position of the group. As the lens that has optical properties of point symmetry, the detection directions depend on the division layout of the photodiode array.

Figure 40B:
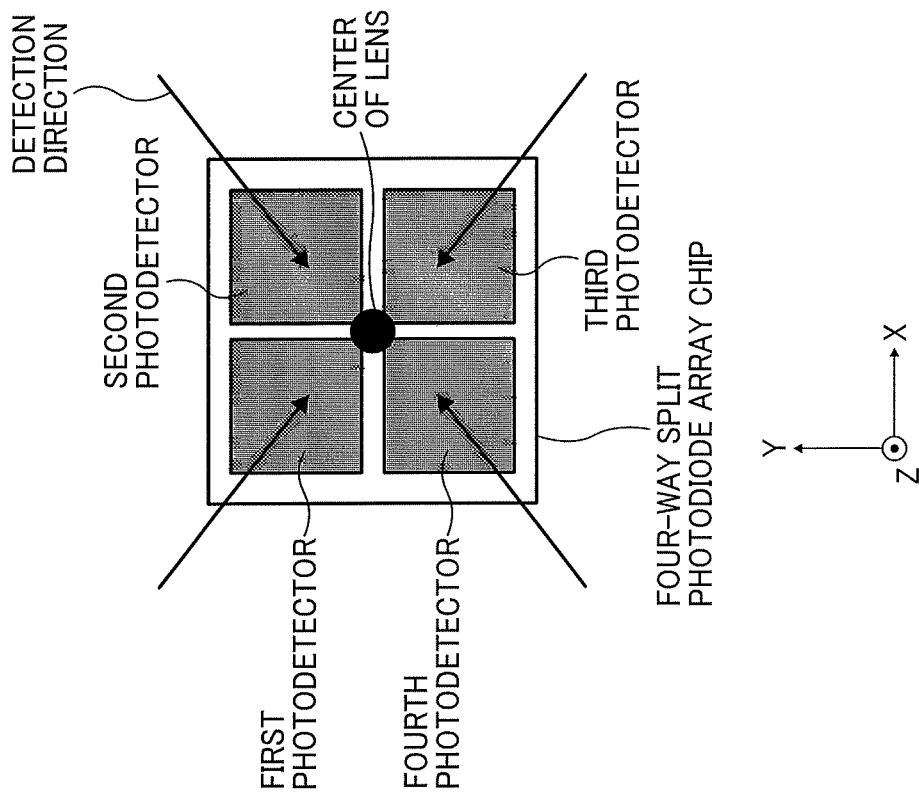
FIG. 40B is a diagram illustrating the detection directions of the four photodiodes of the photodiode array, according to the fourth embodiment of the present disclosure.
Figure 40A:
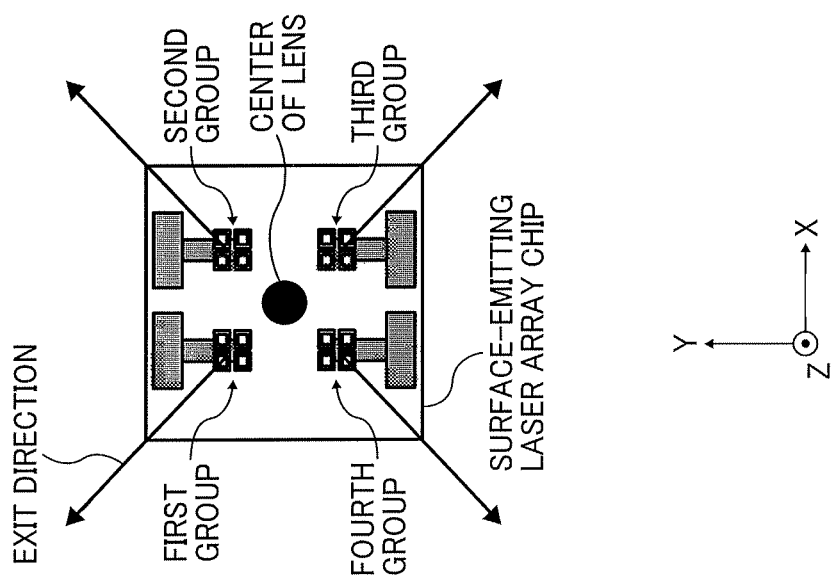
FIG. 40A is a diagram illustrating the exit directions of the four groups of the surface-emitting laser array chip, according to a fourth embodiment of the present disclosure.
Figure 41:
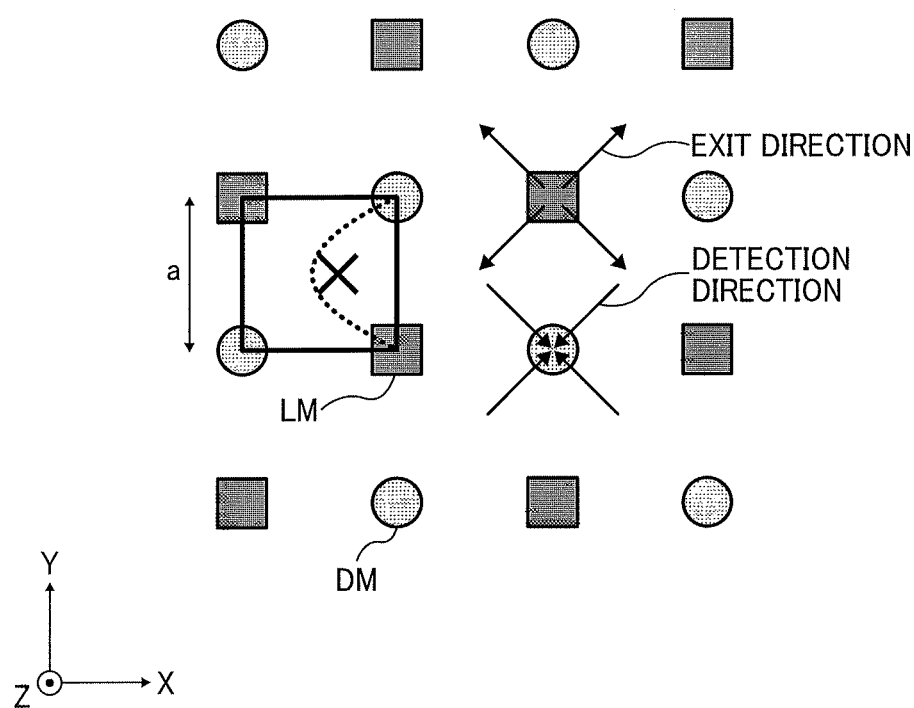
FIG. 41 is a diagram illustrating the exit directions of a plurality of light source modules and the detection directions of a plurality of detection modules in an optical sensor, according to the fourth embodiment of the present invention.

In view of the above circumstances, the surface-emitting laser array chip is designed as illustrated in FIG. 40A, such that the exit directions are inclined with reference to the X direction and the Y direction in a planar view (when viewed from the +X direction). This happens because the center points of the groups are inclined with reference to the center of the lens. In a similar manner to the above, the center of the lens may be disposed at the center of the four-way split photodiode array chip (photodiode array chip) of the detection module DM, such that the detection directions (the incident directions at which the light enters the photoreceptors) become as illustrated in FIG. 40B. The detection directions and the exit directions of the above configuration are illustrated in FIG. 41 with the layout of the probes. The exit directions and the detection directions are inclined with reference to the X direction and the Y direction in a planar view (when viewed from the +X direction).

In such cases, as in the sensitivity distribution described above, the light is anisotropic. Accordingly, in the above configuration according to the fourth embodiment, a higher sensitivity is expected at the point X in FIG. 41.

An inverse problem estimation was performed in the layout of the probes of FIG. 40A and FIG. 40B in a similar manner to the first embodiment, and as a result, it was found that the detectable area is widened in the layout of the probes according to the present embodiment.

Note that in the embodiments described above, the number of the light source modules LM of the irradiation system and the number of the detection modules DM of the detection system may be varied as desired. It is satisfactory as long as the irradiation system includes at least one light source module LM. In a similar manner, it is satisfactory as long as the detection system includes at least one detection module DM.

In the embodiments described above, the configuration of the light source module LM (light irradiator) may be changed as desired. For example, the layout or the number of surface-emitting laser array chips in the light irradiator may be changed as desired. Moreover, for example, the types, shapes, sizes, and the number of the lenses may be changed as desired.

In the embodiments described above, a surface emitting laser is used for the light source of a light irradiator. However, for example, an end-surface emitting laser (laser diode (LD)), a light-emitting diode (LED), organic electroluminescence (EL) element, and a laser other than semiconductor lasers may be used.

In the embodiments described above, a prism is used for the reflection member of a light irradiator. However, other elements such as a mirror may be used instead of the prism.

The number of groups or layout in the surface-emitting laser array chip according to the second variation, or the number of channels or the layout in each of the groups may be changed as desired.

The configuration of the detection module DM (photodetector) may be changed as desired. For example, the aperture may be omitted, or the split lens may be omitted.

As a matter of course, the shape, size, material, number, dimension, or numerical value of the elements or parts described above are given by way of example, and may be changed as desired.

As a matter of course, at least some of the configuration of the optical sensor according to the embodiments of the present invention may be diverted among the embodiments, among the embodiments or the examples.

Numerous additional modifications and variations are possible in light of the above teachings. It is therefore to be understood that within the scope of the appended claims, the disclosure of the present invention may be practiced otherwise than as specifically described herein. For example, elements and/or features of different illustrative embodiments may be combined with each other and/or substituted for each other within the scope of this disclosure and appended claims.

What is claimed is:

1. An optical sensor comprising:
an irradiation system including at least one light irradiator to irradiate a test object with light;
a detection system to detect the light that is emitted from the irradiation system to the test object and has propagated through the test object;
a multilayered structure including an active layer; and
at least one surface-emitting laser element and a photo-sensing element optically connected to the at least one surface-emitting laser element, wherein
the light irradiator is formed in or on the multilayered structure, and
each of the at least one surface-emitting laser element and the photo-sensing element is formed in or on the multilayered structure, and
the at least one surface-emitting laser element and the photo-sensing element independently have respective mesa structures each including the active layer, and
the multilayered structure includes a spacer layer integral to the multilayered structure and covering bottoms of the respective mesa structures of the at least one surface-emitting laser element and the photo-sensing element, respectively, and
each of the bottoms of the respective mesa structures of the surface-emitting laser element and the photo-sensing element, respectively, is adjacent to the active layer of the corresponding mesa structure.

2. The optical sensor according to claim 1, wherein the mesa structure of the photo-sensing element has a slot thereon that is surrounded by an electrode.

3. The optical sensor according to claim 1, wherein
the mesa structure of the photo-sensing element has a reflector on an opposite side of the spacer layer with respect to the active layer, and
$\theta 1 < \theta 2$
where $\theta 1$ denotes a tilt angle of a side of the active layer and the spacer layer of the mesa structure of the photo-sensing element and $\theta 2$ denotes a tilt angle of a side of the reflector.

4. The optical sensor according to claim 1, wherein the at least one surface-emitting laser element and the photo-sensing element are optically attached to each other at least via the spacer layer.

5. The optical sensor according to claim 4, wherein the at least one surface-emitting laser element and the photo-sensing element have a portion that optically connects the surface-emitting laser element and the photo-sensing element,
the portion having an optical thickness equivalent to an oscillation wavelength λ, of the surface-emitting laser element.

6. The optical sensor according to claim 1, wherein
the multilayered structure further includes an insulator film disposed above the spacer layer, and
the at least one surface-emitting laser element and the photo-sensing element are optically attached to each other at least via the insulator film.

7. The optical sensor according to claim 6, wherein
the insulator film has a refractive index smaller than a refractive index of the spacer layer.

8. The optical sensor according to claim 6, wherein
the insulator film has a surface roughness equal to or less than one-tenths of oscillation wavelength λ of the at least one surface-emitting laser element.

9. The optical sensor according to claim 6, wherein
the insulator film is composed of silicon oxide or silicon nitride.

10. The optical sensor according to claim 1, wherein
the at least one surface-emitting laser element comprises a plurality of surface-emitting laser elements to irradiate an identical point of the test object with a plurality of light rays that are not parallel to each other.

11. The optical sensor according to claim 1, wherein
the light irradiator further comprises an optical system disposed between the multilayered structure and the test object.

12. The optical sensor according to claim 11, wherein
the detection system includes at least one photodetector having a plurality of photoreceptors to detect a plurality of light rays that are emitted from the irradiation system to the test object and have propagated through the test object.

13. The optical sensor according to claim 12, wherein
the photodetector has a member disposed between the test object and the plurality of photoreceptors and the member has a transmissive portion thereon, and
some of each of the plurality of light rays that have propagated through the test object passes through the transmissive portion.

14. An optical examination device comprising:
an optical sensor including
    an irradiation system including at least one light irradiator to irradiate a test object with light,
    a detection system to detect the light that is emitted from the irradiation system to the test object and has propagated through the test object,
    a multilayered structure including an active layer, and
    at least one surface-emitting laser element and a photo-sensing element optically connected to the at least one surface-emitting laser element; and
a controller to calculate optical properties of the test object based on a detection result of the optical sensor, wherein
the light irradiator is formed in or on the multilayered structure,
the multilayered structure including
each of the at least one surface-emitting laser element and the photo-sensing element is formed in or on the multilayered structure, and
the at least one surface-emitting laser element and the photo-sensing element independently have respective mesa structures each including the active layer, and
the multilayered structure includes a spacer layer integral to the multilayered structure and covering bottoms of the respective mesa structures of the at least one surface-emitting laser element and the photo-sensing element, respectively, and
each of the bottoms of the respective mesa structures of the surface-emitting laser element and the photo-sensing element, respectively, is adjacent to the active layer of the corresponding mesa structure.

15. The optical sensor according to claim 1, wherein a surface-emitting laser element amongst the at least one surface-emitting laser element is the irradiator that irradiates the test object with light.

* * * * *